US009346749B2

(12) United States Patent
Jung et al.

(10) Patent No.: US 9,346,749 B2
(45) Date of Patent: May 24, 2016

(54) 1,3-DI-OXO-INDENE DERIVATIVE, PHARMACEUTICALLY ACCEPTABLE SALT OR OPTICAL ISOMER THEREOF, PREPARATION METHOD THEREOF, AND PHARMACEUTICAL COMPOSITION CONTAINING SAME AS AN ANTIVIRAL, ACTIVE INGREDIENT

(75) Inventors: Young Sik Jung, Daejeon (KR); Chong Kgo Lee, Daejeon (KR); Ihl Young Choi, Daejeon (KR); Hae Soo Kim, Daejeon (KR); Pil Ho Kim, Daejeon (KR); Soo Bong Han, Daejeon (KR); Johan Neyts, Belgium (BE); Hendrik Jan Thibaut, Belgium (BE)

(73) Assignees: Korea Research Institute of Chemical Technology, Daejeon-Si (KR); Katholieke Universiteit Leuven K.U., Belgium (BE)

( * ) Notice: Subject to any disclaimer, the term of this patent is extended or adjusted under 35 U.S.C. 154(b) by 207 days.

(21) Appl. No.: 14/126,479

(22) PCT Filed: Jun. 18, 2012

(86) PCT No.: PCT/KR2012/004804
§ 371 (c)(1),
(2), (4) Date: Dec. 16, 2013

(87) PCT Pub. No.: WO2012/173447
PCT Pub. Date: Dec. 20, 2012

(65) Prior Publication Data
US 2014/0121187 A1    May 1, 2014

(30) Foreign Application Priority Data

Jun. 16, 2011 (KR) .................. 10-2011-0058704
Jun. 18, 2012 (KR) .................. 10-2012-0065023

(51) Int. Cl.
*A61K 31/122* (2006.01)
*A61K 31/435* (2006.01)
*C07D 221/04* (2006.01)
*C07C 49/747* (2006.01)
*C07C 269/00* (2006.01)
*C07C 271/24* (2006.01)
*C07C 271/44* (2006.01)
*C07C 271/64* (2006.01)
(Continued)

(52) U.S. Cl.
CPC ............. *C07C 269/00* (2013.01); *C07C 45/00* (2013.01); *C07C 49/747* (2013.01); *C07C 49/753* (2013.01); *C07C 67/00* (2013.01); *C07C 69/12* (2013.01); *C07C 69/16* (2013.01); *C07C 69/18* (2013.01); *C07C 69/22* (2013.01); *C07C 69/28* (2013.01); *C07C 69/54* (2013.01); *C07C 69/618* (2013.01); *C07C 69/63* (2013.01); *C07C 69/736* (2013.01); *C07C 69/738* (2013.01); *C07C 69/78* (2013.01); *C07C 205/45* (2013.01); *C07C 225/20* (2013.01); *C07C 225/22* (2013.01); *C07C 233/32* (2013.01); *C07C 233/33* (2013.01); *C07C 233/41* (2013.01); *C07C 233/43* (2013.01); *C07C 233/61* (2013.01); *C07C 233/76* (2013.01); *C07C 247/14* (2013.01); *C07C 271/24* (2013.01); *C07C 271/44* (2013.01); *C07C 271/64* (2013.01); *C07C 275/26* (2013.01); *C07C 275/64* (2013.01); *C07C 323/22* (2013.01); *C07D 213/65* (2013.01); *C07D 215/20* (2013.01); *C07C 2101/02* (2013.01); *C07C 2102/08* (2013.01)

(58) Field of Classification Search
CPC .. C07C 49/747; C07D 221/04; A61K 31/122; A61K 31/435
USPC ............ 560/145; 546/112; 514/298, 569, 681
See application file for complete search history.

(56) References Cited

U.S. PATENT DOCUMENTS 4,569,945 A *  2/1986  Campbell .............. A61K 31/12
                                                      514/569
2002/0091261 A1    7/2002  Bold et al.

FOREIGN PATENT DOCUMENTS

EP    1081138 A1    3/2001
EP    2324820       6/2011
(Continued)

OTHER PUBLICATIONS

Solomek et al, JOCS, (2010), pp. 1-5.*
Guy D. Diana; "Inhibitors of Picornavirus Replication", Current Medicinal Chemistry-Anti-Infective Agents, vol. 2, No. 1, Mar. 2003, pp. 1-12.
James M. Groarke, et al; "Attenuated Virulence of Pleconaril-Resistant Coxsackievirus B3 Variants", The Journal of Infectious Diseases, Jun. 1999, vol. 179(6); pp. 1538-1541.
(Continued)

*Primary Examiner* — Kamal Saeed
*Assistant Examiner* — Janet L Coppins
(74) *Attorney, Agent, or Firm* — Brinks Gilson & Lione

(57) ABSTRACT

Disclosed are 1,3-Dioxoindene derivatives, pharmaceutically acceptable salts thereof or enantiomers, a preparation method thereof, and a pharmaceutical composition for the prevention or treatment of viral diseases, comprising the same as an active ingredient. The 1,3-Dioxoindene derivatives have excellent inhibitory activity against picornaviruses including coxsackie-, entero-, echo-, Polio-, and rhinoviruses, as well as exhibiting low cytotoxicity, so that they can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

20 Claims, No Drawings

(51) Int. Cl.

| | |
|---|---|
| C07C 275/26 | (2006.01) |
| C07C 275/64 | (2006.01) |
| C07C 205/45 | (2006.01) |
| C07C 323/22 | (2006.01) |
| C07C 225/20 | (2006.01) |
| C07C 225/22 | (2006.01) |
| C07C 233/32 | (2006.01) |
| C07C 233/33 | (2006.01) |
| C07C 233/41 | (2006.01) |
| C07C 233/43 | (2006.01) |
| C07C 233/61 | (2006.01) |
| C07C 233/76 | (2006.01) |
| C07C 247/14 | (2006.01) |
| C07C 69/16 | (2006.01) |
| C07C 69/18 | (2006.01) |
| C07C 69/28 | (2006.01) |
| C07C 69/54 | (2006.01) |
| C07C 69/618 | (2006.01) |
| C07C 69/63 | (2006.01) |
| C07C 69/738 | (2006.01) |
| C07C 69/78 | (2006.01) |
| C07C 49/753 | (2006.01) |
| C07D 215/20 | (2006.01) |
| C07D 213/65 | (2006.01) |
| C07C 45/00 | (2006.01) |
| C07C 67/00 | (2006.01) |
| C07C 69/12 | (2006.01) |
| C07C 69/22 | (2006.01) |
| C07C 69/736 | (2006.01) |

(56) References Cited

FOREIGN PATENT DOCUMENTS

| | | |
|---|---|---|
| FR | 2392951 | 1/1976 |
| GB | 1533388 | 11/1978 |
| JP | 60-109541 A | 6/1985 |
| JP | 2001 089455 | 4/2001 |
| RU | 2207132 | 6/2003 |
| WO | WO 03/082265 A2 | 10/2003 |

OTHER PUBLICATIONS

Beverly A. Heinz, et al; "The Antiviral Compound Enviroxime Targets the 3A Coding Region of Rhinovirus and Poliovirus", Journal of Virology, vol. 6, No, 7, Jul. 1995, p. 4189-4197.
Rebecca M. Ledford, et al; "VP1 Sequencing of All Human Rhinovirus Serotypes: Insights into Genus Phylogeny and Susceptibility to Antiviral Capsid-Binding Compounds", Journal of Virology, vol. 78, No. 7, Apr. 2004, pp. 3663-3674.
Mark A. McKinlay, et al; "Treatment of the Picornavirus Common Cold by Inhibitors of Viral Uncoating and Attachment", Annual Review of Microbiollogy, Oct. 1992, vol. 46, pp. 635-654.
F. Dewolfe Miller, et al; "Controlled Trial of Enviroxime Against Natural Rhinovirus Infections in a Community", Antimicrobial Agents and Chemotherapy, Jan. 1985, vol. 27, No. 1, pp. 102-106.
A.K. Patrick, et al; "In Vitro Antiviral Activity of AG7088, a Potent Inhibitor of Human Rhinovirus 3C Protease", Antimicrobial Agents and Chemotherapy, Oct. 1999, vol. 43, No. 10, pp. 2444-2450.
Daniel C. Pevear, et al; "Activity of Pleconaril against Enteroviruses", Antimicrobial Agents and Chemotherapy, Sep. 1999, vol. 43, No. 9, pp, 2109-2115.
Suven Das, et al; "A simple synthesis of 4-substituted 2,3-benzoxazinones from C-2 arylated 1,3-indanediones", Tetrahedron Letters, vol. 52, pp. 3243-3246; Available online Apr. 27, 2011.
Mona Kafoor et al; "Stereoselective synthesis of Z-3-alkoxy-2-[(4'-methoxyphenyl)methylidene]-1(3H-isobenzofuranones", Tetrahedron; vol. 59, pp. 5027-2031; Jun. 30, 2003.
Hyun Nam Song, et al; "The Reaction of Ninhydrin with Polymethylbenzenes in the Presence of Acid Catalyst: Formation of 2-aryl-1,3-indanedione and Indenoindanone Derivatives", Bull. Korean Chem. Soc. vol. 20, No. 10, pp. 1229-1231; Oct. 20, 1999.
Masaya Suzuki, et al; "Photorearrangements in spiro-conjoined cyclohexa-2,5-dien-1-one", Tetrahedron vol. 67, pp. 5500-5506; Available online May 14, 2011.
International Search Report mailed Dec. 28, 2013; PCT/KR2012/004804.
Aleman, J. et al., "Organocatalytic Highly Enantioselective α-Arylation of β-Ketoesters", Angewandte Chemie International Edition, 2007, vol. 46, pp. 5515-5519.
Almog, Joseph et al., "The reaction between phloroglucinol and vic polycarbonyl compounds: extension and mechanistic elucidation of Kim's synthesis for bipolarofacial bowl-shaped compounds", Tetrahedron 65, (2009), pp. 7954-7962.
Benders, J. et al., "Esr spectra of semidiones derived from indandione -1,3," Journal of Molecular Structure, vol. 19, (Dec. 1, 1973), pp. 431-440.
Courant, J. et al., "1,3-Indandiones VIII. 2-Hydroxy-2-indolyl-1,3-indandiones, 2-(indol-3-ylmethylene indandione and derivatives: search for anti-inflammatory activity," European Journal of Medicinal Chemistry, Editions Scientifique Elsevier, Paris, FR., vol. 24, No. 2, (Mar. 1, 1989), pp. 145-154.
Das, S. et al., "A Facile Synthesis of Benzofuroisocoumarins from C-2 Arylated 1,3-Indanediones", Synlett, 2006, vol. 2, pp. 207-210.
Das, Suven et al., "A simple synthesis of 4-substituted 2,3-benzoxazinones from C-2 arylated 1,3-indanediones", Tetrahedron Letters, vol. 52, No. 25, (Apr. 27, 2011) pp. 3243-3246.
Extended European Search Report for EP 12799827.6, mailed Nov. 19, 2014.
Heffner, Robert J., Joullie, Madeleine, "A Synthesis of Two Novel Benzo[f]Ninhydrin Analogs: 6-Methoxybenzo[f]Ninhydrin and Thieno[f]Ninhydrin", Synthetic Communications, 21(8&9), (1991), pp. 1055-1069.
Heffner, Robert J., Joullie, Madeleine, "Synthetic Routes to Ninhydrines, Preparation of Ninhydrin, 5-Methoxyninhydrin, and 5-(Methylthio)Ninhydrin.", Synthetic Communications, 21(21); (1991); pp. 2231-2256.
Hark, Richard R. et al. "Synthetic studies of novel ninhydrin analogs", Can. J. Chem., vol. 79, (2001); pp. 1632-1654.
International Search Report and Written Opinion of the International Searching Authority for PCT/KR2012/004804, mailed Dec. 28, 2012.
Jeyachandran, Malaichamy et al., "Synthesis, Antimicrobial, and Anticoagulant Activities of 2-(Arylsulfonyl) indane-1,3-diones", Organic Chemistry International, vol. 2, No. 4, (Jan. 1, 2011), pp. 175-179.
Kapoor, Mona et al., "Stereoselective Synthesis of Z-3-alkoxy-2-[(4'-methoxyphenyl)methylidene]-1(3H)-isobenzofuranones", Tetrahedron Letters, vol. 59, No. 27, pp. 5027-5031, (Jun. 30, 2003).
Liu, Yaya et al., "Investigating the Origin of the Slow-Binding Inhibition of HCV NS3 Serine Protease by a Novel Substrate Based inhibitor", BioChemistry, vol. 42, No. 29, (Jul. 1, 2003), pp. 8862-8869.
Lombardino, J.G. et al., "Anti inflammatory 2-Aryl-1,3-indandiones", Journal of Medicinal Chemistry, (1968), vol. 11, No. 6, pp. 342-347.
Mosher, William A. et al., "Reactions of some methylene ketones with dimethyl phthalate. New route to 2-substituted 1,3-indandiones", The Journal of Organic Chemistry, vol. 36, No. 11, (Jun. 1, 1971), pp. 1561-1563.
Neiland, L.E. et al., "2-Aryl-4-azaindain-1, 3-diones", Chemistry of Heterocyclic Compounds, vol. 3, No. 1, (Jan. 1, 1969), pp. 81-83.
Ozola, A. Ya et al., "4-Azaindane-1, 3-dione derivatives. III. Reactivities and prototropic transformations of new 4-azaindane-1,3-diones", Chemistry of Heterocyclic Compounds, vol. 12, No. 2, (Feb. 1, 1976), pp. 220-226.
Ozola, A. Ya et al., "A new method of synthesizing 4-azaidan-1, 3-dione derivatives", Chemistry of Heterocyclic Compounds, vol. 9, No. 8, (Aug. 1, 1973), pp. 1062-1062.
Poupelin, Jean Pierre et al., "Synthese Et Proprietes Pharmalogiques De Derives De L'Hydroxy-2 Indanedione-1,3; I. Produits De Con-

(56) References Cited

OTHER PUBLICATIONS densation De La Ninhydrine Avec Les Phenols C-Alkyles", *Eur. J. Med. Chem.—Chimica Therapeutique*, Mar.-Apr. vol. 14, No. 2, (Jan. 1, 1979), pp. 171-179.

Poupelin, J.P. et al., "Dervies de 1 'hydroy-2 indanedione-1, 3.II. Produits de condensation de la ninhydrine avec les polyphenols et leurs derives 0-methyles// 2-hydroxy-1,3-indanedione derivatives. II. (Condensation of ninhydrin with polyphenols and their 3-methylated derivatives)", *European Journal of Medicinal Chemistry*, Editions Scientifique, vol. 15, No. 3, (Jan. 1, 1980), pp. 253-262.

Schmitt, Gerard et al., "A New and Mild Synthesis of Substituted Salicylic Acids", *Synthesis*, vol. 1984, No. 09 (Jan. 1, 1984), pp. 758-760.

Song, H.N. et al., "Formation of Benzo[b]Indeno [2,1-d]Furanone Ring System During Alkylation of 2-(2-Hydroxyaryl)-2-Hydroxy-1,3-Indanedione Derivatives", *Synthetic Communications*, (1999), vol. 29, No. 16, pp. 2759-2767.

Song, Hyun Nam et al., "Friedel-Crafts Type Reactions of Some Activated Cyclic Ketones with Phenol Derivatives", *Synthetic Communications*, 29(19), pp. 3303-3311, (1999).

Song, Hyun Nam et al., "A Study on the Friedel-Crafts Type Reaction of Ninhydrin with Arenes", *Synthetic Communications*, 28(10), pp. 1865-1870, (1998).

Song, Hyun Nam et al., "The Reaction of Ninhydrink with Trimethylbenzenes Under Friedel-Crafts Reaction Conditions", *Synthetic Communications*, 30(6), pp. 1057-1066, (2000).

Song, Hyun Nam et al., "Difference in Reactivity during Alkylation of 2-(2-Hydroxyaryl)-1,3-indanedione and N-(2-Hydroxyphenyl)phthalimide", *Bull. Korean Chem. Soc.*, (1999); vol. 20, No. 6, pp. 631-632.

Thibaut et al., "A novel class of highly potent small molecule inhibitors of entero/rhinovirus replication with an excellent safety and pharmacokinetic profile are highly effective against enterovirus infections in mice.", Poster presented at *26th International Conference on Antiviral Research*, San Francisco, CA, (May 11-15, 2013).

Thibaut et al., "A novel class of highly potent small molecule inhibitors of entero/rhinovirus replication that target the non-structural protein 2C", Poster presented at 26th International Conference on Antiviral Research, San Francisco, CA (May 11-15, 2013).

The Merck Index, 2001, Thirteenth Edition, p. 674, 1380, 2432, 7314.

Yin-Murphy, Marguerite and Almond, Jeffrey W., "Chapter 53Picornaviruses", *Medical Microbiology*, 4th Ed., Galveston (TX): Univ. of Texas Medical Branch at Galveston, (1996), pp. 1-18.

\* cited by examiner

1,3-DI-OXO-INDENE DERIVATIVE, PHARMACEUTICALLY ACCEPTABLE SALT OR OPTICAL ISOMER THEREOF, PREPARATION METHOD THEREOF, AND PHARMACEUTICAL COMPOSITION CONTAINING SAME AS AN ANTIVIRAL, ACTIVE INGREDIENT

TECHNICAL FIELD

The present invention relates to 1,3-Dioxoindene derivatives, pharmaceutically acceptable salts thereof or enantiomers thereof, preparation methods thereof, and pharmaceutical compositions for the prevention and treatment of viral diseases, comprising the same.

BACKGROUND ART

Picornaviruses are non-enveloped, positive single-stranded RNA viruses with an RNA genome 7.2-8.5 Kb long. These viruses are very small and globular in shape with a size of about 22~30 nm, and were first identified a long time ago. Among the viruses belonging to the family Picornaviridae are enteroviruses including rhinovirus, poliovirus, coxsackievirus A, coxsackievirus B, and echovirus, and hepatitis A virus.

The diseases that picornaviruses cause are varied, ranging from respiratory diseases to digestive diseses, to circulatory diseases and to dermal diseases, examples of which include poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, and foot-and-mouth disease. However, there are no therapeutics for curing these diseases. Most of the drugs under development are uncoating inhibitors. Viruses belonging to the family Picornaviridae cause various diseases including the aforementioned respiratory diseases, which evoke hygienic, social and economic issues. Picornaviruses are the main causative agents of waterborne diseases. Being very stable and difficult to disinfect, the RNA viruses incessantly cause related diseases.

Human rhinoviruses (hRV) have been recently associated with the majority of asthma exacerbations, and are known to exist even in bronchial tissues of many stable asthma patients. Comparison of respective bronchial mucosa biopsy specimens taken from asthma and non-asthma patients showed significantly higher frequencies of detection of human rhinoviruses in the lower respiratory tract of asthma patients, compared to non-asthma patients. It has also been reported that there is correlation between the presence of human rhinovirus and the clinical severity of asthma. In addition, rhinoviruses cause chronic obstructive pulmonary disease, pneumonia, sinusitis, and otitis media as well as asthma.

Rhinoviruses are the main causative of the common cold while enterovirus-induced diseases include meningitis, respectory tract infection, etc. Extensive effort to provide vaccination against poliovirus has significantly reduced the onset of poliomyelitis worldwide, but there are still reports of cases of the disease in Niger, Nigeria, Egypt, India, Pakistan, and Afghanistan. Hepatitis A is now possible to control to some degree thanks to vaccines for hepatitis A viruses. However, no vaccines for coxsackieviruses, echoviruses, or rhinoviruses have been developed, thus far.

Particularly, coxsackievirus B is a main cause of myocarditis, which may develop, in serious cases, into idiopathic dilated cardiomyopathy, which requires heart transplantation Enviroxime derivatives are considered the most promising candidate with a broad anti-enterovirus- and anti-rhinovirus activity. Enviroxime interferes with the synthesis of plus-strand RNA by binding to the virus protein 3A that is required for the formation of RNA intermediates in the virus reproduction (Heinz B A and Vance L M: J Virol, 1995, 69(7), 4189-97). In clinical studies, however, the compound was observed to have insignificant or few therapeutic effects, with the concomitant detection of bad pharmacokinetics and unwanted side effects (Miller F D et al.: Antimicrob Agents Chemother, 1985, 27(1), 102-6).

The protease inhibitor AG 7088 has been developed on the basis of the knowledge about the fine structure and function of the viral protease 2C. In the cell culture in the nanomolar concentration range, AG 7088 has an effect against 48 rhinovirus types and coxsackievirus A21, B3, enterovirus 70 and echovirus 11 (Pattick A K et al.: Antimicrobila Agents Chemother, 1999, 43(10), 2444-50).

Thanks to the clarification of the molecular structure of the viral capsids, the preconditions for a purposeful design of capsid blockers, the "WIN substances", have been obtained (Diana G D: Curr Med Chem 2003, 2, 1-12). They inhibit the adsorption and/or the uncoating of rhinoviruses and enteroviruses. Some of the WIN substances have a highly specific effect only against individual genera or virus types of the picornaviruses. Other derivatives inhibit the replication both of rhinoviruses and enteroviruses. Arildone, disoxaril and pirodavir belong, for example, to the WIN substances. These compounds showed very good antiviral effects in the cell culture. However, a poor solubility (arildone), low bioavailability (arildone and disoxaril), a rapid metabolization and excretion (disoxaril and WIN 54954) as well as side effects, such as skin rash (WIN 54954), made a clinical application impossible.

Pleconaril, a kind of WIN substance, has a very good oral bioavailability and after its binding to the hydrophobe pocket in the viruscapsid, it inhibits the penetration of rhino-, echo- and coxsackieviruses (Pevear D C et al.: Antimicrob Agents Chemother 1999, 43(9), 2109-15; McKinlay M A et al.: Annu Rev Microbiol 1992, 46, 635-54). Therefore, pleconaril is potentially effective against a broad spectrum of virus diseases, ranging from the common cold to the viral meningitis or myocarditis. Resistances were observed for rhinoviruses, enterovirus 71 and coxsackievirus B3 (Ledford R M et al.: J Virol 2004, 78(7), 3663-74; Groarke J M et al.: J Infect Dis 1999, 179(6), 1538-41). However, the proven therapeutic effect was not sufficient for the registration of pleconaril (Picovir, Viropharma, USA) as an agent for the treatment of rhinovirus infections in the USA. In March 2002, a corresponding application was refused by the Food and Drug Administration (FDA) because therapy success was too low and side effects were observed.

BTA-798 was found to have higher antiviral activity than pleconaril, as evaluated in vitro and in vivo with rhinoviruses, and is now being under a clinical test (Ryan, J. et al. Antiviral Res [18th Intl Conf Antiviral Res (April 11-14, Barcelona) 2005] 2005, 65(3): Abst LB-11).

However, no antiviral drugs that have gained approval for use in the treatment of entero- or rhinoviruses have been developed, so far.

Leading to the present invention, intensive and thorough research into effective virustatics against picornaviruses including coxsackie-, entero-, echo-, polio-, and rhinoviruses, culminated in the finding that novel 1,3-Dioxoindene derivatives exhibit highly inhibitory activity against picornaviruses including coxsackie-, entero-, echo-, polio-, and rhinoviruses.

DISCLOSURE

Technical Problem

It is therefore an object of the present invention to provide a 1,3-Dioxoindene derivative, or a pharmaceutically acceptable salt thereof.

It is another object of the present invention to provide a method for the preparation of the 1,3-Dioxoindene derivative, or pharmaceutically acceptable salt thereof.

It is a further object of the present invention to provide a pharmaceutical composition for the prevention or treatment of a viral disease, comprising the 1,3-Dioxoindene derivative, or pharmaceutically acceptable salt thereof as an active ingredient.

Technical Solution

In accordance with an aspect thereof, the present invention provides an 1,3-Dioxoindene derivative represented by the following Chemical Formula 1, a pharmaceutically acceptable salt thereof, or an enantiomer thereof:

[Chemical Formula 1]

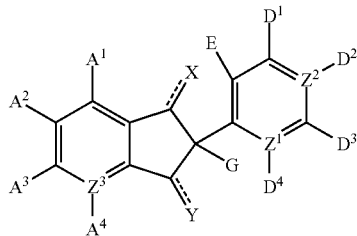

(wherein, $A^1, A^2, A^3, A^4, D^1, D^2, D^3, D^4, Z^1, Z^2, Z^3, X, Y, E$ and G are respectively as defined in the following description of the specification.)

In accordance with another aspect thereof, the present invention provides a method for the preparation of the 1,3-Dioxoindene derivative, pharmaceutically acceptable salt or enantiomer.

In accordance with a further aspect thereof, the present invention provides a pharmaceutical composition for the prevention or treatment of a viral disease, comprising the 1,3-Dioxoindene derivative, pharmaceutically acceptable salt or enantiomer as an active ingredient.

Advantageous Effects

Having excellent inhibitory activity against picornaviruses including coxsackie-, entero-, echo-, Polio-, and rhinoviruses, as well as exhibiting low cytotoxicity, the 1,3-Dioxoindene derivative of Chemical Formula 1 can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hapatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media.

BEST MODE

Below, a detailed description will be given of the present invention.

According to one aspect thereof, the present invention addresses 1,3-Dioxoindene derivatives expressed by Formula 1, pharmaceutically-acceptable salt thereof or optical isomer thereof:

[Chemical Formula 1]

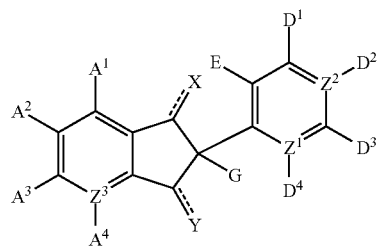

wherein, $A^1, A^2, A^3$ and $A^4$ are, either independently or optionally, any one selected from a group consisting of —H, halogen, —OH, —CN, —N$_3$, C$_1$~C$_{10}$ alkoxy, C$_1$~C$_{10}$ straight- or branched-chain alkyl, C$_6$~C$_{12}$ aryl, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$ and —NR$^1$(C=S)—NR$^2$R$^3$, or two or more neighboring substituents $A^1, A^2, A^3$ and $A^4$ may form a ring together, wherein a ring formed by two or more neighboring substituents $A^1, A^2, A^3$ and $A^4$ may include one or more hetero atom, and the hetero atom is N, O or S;

G is —H, halogen, —OH, —CN, —N$_3$, C$_1$~C$_{10}$ alkoxy, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, —NR$^1$(C=S)—NR$^2$R$^3$ or

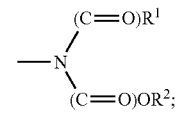

$D^1, D^2, D^3$ and $D^4$ are, either independently or optionally, any one selected from a group consisting of —H, halogen, —OH, —CN, C$_1$~C$_{10}$ alkoxy, C$_1$~C$_{10}$ straight- or branched-chain alkyl, C$_6$~C$_{12}$ aryl, —(CH$_2$)$_n$—(C=O)OR$^1$, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, —SR$^1$ and —NR$^1$(C=S)—NR$^2$R$^3$, or two or more neighboring substituents $D^1, D^2, D^3$ and $D^4$ may form a ring together, a ring formed by two or more neighboring substituent $D^1, D^2, D^3$ and $D^4$ may include one or more hetero atom, and the hetero atom is N, O or S;

E is —H, —OH, —OR$^1$, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —SR$^1$, —NR$^1$(C=S)R$^2$, —NR$^1$(C=O)OR$^2$, —NR$^1$(C=O)—NR$^2$R$^3$ or —NR$^1$(C=S)—NR$^2$R$^3$;

$R^1, R^2$ and $R^3$ are, each independently, hydrogen, nonsubstituted or phenyl-substituted C$_1$~C$_{10}$ straight- or branched-chain alkyl, C$_1$~C$_{10}$ alkoxy, nonsubstituted or phenyl-substituted C$_1$~C$_{10}$ straight- or branched-chain alkenyl, C$_3$~C$_7$ cycloalkyl or nonsubstituted or phenyl-substituted C$_6$~C$_{12}$ aryl;

X and Y are, each independently, hydrogen, oxygen, hydroxy or sulfur;

$Z^1$, $Z^2$ and $Z^3$ are carbon or nitrogen;

n is integer between 1~10; and

≡≡≡ denotes single or double bond.

In a preferred embodiment, $A^1$, $A^2$, A3 and $A^4$ are, either independently or optionally, any one selected from a group consisting of —H, halogen, $C_1$~$C_{10}$ straight- or branched-chain alkyl, —$NR^1R^2$, —$NR^1$(C=O)$R^2$, or two or more neighboring substituents $A^1$, $A^2$, $A^3$ and $A^4$ may form a ring together, wherein a ring formed by two or more neighboring substituents $A^1$, $A^2$, $A^3$ and $A^4$ may include one or more hetero atom, and the hetero atom is N, O or S;

G is —OH, —O(C=O)$R^1$, —O(C=O)O$R^1$, —$NR^1$(C=O)$R^2$, —$NR^1$(C=O)O$R^2$ or

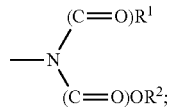

$D^1$, $D^2$, $D^3$ and $D^4$ are, either independently or optionally, any one selected from a group consisting of halogen, $C_1$~$C_{10}$ straight- or branched-chain alkyl, —$NR^1$(C=O)$R^2$, —$NR^1$(C=O)O$R^2$ and —$NR^1$(C=O)—$NR^2R^3$, or two or more neighboring substituents $D^1$, $D^2$, $D^3$ and $D^4$ may form a ring together, wherein a ring formed by two or more neighboring substituents $D^1$, $D^2$, $D^3$ and $D^4$ may include one or more hetero atom, and the hetero atom is N, O or S;

E is —H, —OH, —O$R^1$, —O(C=O)$R^1$, —O(C=O)O$R^1$, —O(C=O)$NR^1R^2$, —$NR^1$(C=O)$R^2$ or —$NR^1$(C=O)O$R^2$;

$R^1$, $R^2$ and $R^3$ are, each independently, hydrogen, nonsubstituted or phenyl-substituted $C_1$~$C_9$ straight- or branched-chain alkyl, nonsubstituted or phenyl-substituted $C_1$~$C_5$ straight- or branched-chain alkenyl or $C_6$~$C_{10}$ aryl;

X and Y are, each independently, oxygen or hydroxy;

$Z^1$, $Z^2$ and $Z^3$ are carbon;

n is integer between 1~5; and

≡≡≡ denotes single or double bond.

In a more preferred embodiment, $A^1$, $A^2$, $A^3$ and $A^4$ are, either independently or optionally, any one selected from a group consisting of —H, halogen and —$NR^1R^2$;

G is —OH, —$NR^1$(C=O)$R^2$ or —$NR^1$(C=O)O$R^2$;

$D^1$, $D^2$, $D^3$ and $D^4$ are, either independently or optionally, any one selected from a group consisting of halogen, $C_1$~$C_{10}$ straight- or branched-chain alkyl and —$NR^1$(C=O)$R^2$;

E is —H, —OH, —O$R^1$, —O(C=O)$R^1$, —O(C=O)O$R^1$ or —O(C=O)$NR^1R^2$;

$R^1$, $R^2$ and $R^3$ are, each independently, hydrogen, nonsubstituted or phenyl-substituted $C_1$~$C_8$ straight- or branched-chain alkyl, nonsubstituted or phenyl-substituted $C_1$~$C_4$ straight- or branched-chain alkenyl or $C_6$~$C_{10}$ aryl;

X and Y are oxygen;

$Z^1$, $Z^2$ and $Z^3$ are carbon;

n is integer between 1~3; and

≡≡≡ denotes double bond.

In a further more preferred embodiment, $A^1$, $A^2$, $A^3$ and $A^4$ are, either independently or optionally, any one selected from a group consisting of —H and —$NR^1R^2$;

G is —$NR^1$(C=O)$R^2$;

$D^1$, $D^2$, $D^3$ and $D^4$ are $C_1$~$C_{10}$ straight- or branched-chain alkyl;

E is —O(C=O)$R^1$;

$R^1$, $R^2$ and $R^3$ are, each independently, hydrogen or $C_1$~$C_7$ straight- or branched-chain alkyl;

X and Y are oxygen;

$Z^1$, $Z^2$ and $Z^3$ are carbon;

n is integer between 1-3; and

≡≡≡ denotes double bond.

Concrete examples of the compound represented by Chemical Formula 1 include:

1) Ethyl 2-(4-acetoxy-3-(2-acetoxy-1,3-dioxo-2,3-dihydro-1H-inden-2-yl)-5-methoxyphenyl)acetate;
2) 2-(2-Acetoxy-1,3-dioxo-2,3-dihydro-1H-inden-2-yl)-4,5-dimethylphenyl acetate;
3) 2-(2-Acetoxy-1,3-dioxo-2,3-dihydro-1H-inden-2-yl)-5-chlorophenyl acetate;
4) 6-(2-Acetoxy-1,3-dioxo-2,3-dihydro-1H-inden-2-yl)-2,3-dichlorophenyl acetate;
5) 2-(2-Acetoxy-1,3-dioxo-2,3-dihydro-1H-inden-2-yl)-4,6-dichlorophenyl acetate;
6) 2-(2-Acetoxy-1,3-dioxo-2,3-dihydro-1H-inden-2-yl)-5-ethylphenyl acetate;
7) 2-(2-Acetoxy-1,3-dioxo-2,3-dihydro-1H-inden-2-yl)-4-methoxyphenyl acetate;
8) 4-(2-Acetoxy-1,3-dioxo-2,3-dihydro-1H-inden-2-yl)biphenyl-3-yl acetate;
9) 2-(2-Acetoxy-1,3-dioxo-2,3-dihydro-1H-inden-2-yl)-4-nitrophenyl acetate;
10) 3-(2-Acetoxy-1,3-dioxo-2,3-dihydro-1H-inden-2-yl)biphenyl-4-yl acetate;
11) 2-(2-Acetoxy-1,3-dioxo-2,3-dihydro-1H-inden-2-yl)-4-propylphenyl acetate;
12) 2-(2-Acetoxy-1,3-dioxo-2,3-dihydro-1H-inden-2-yl)-4-ethylphenyl acetate;
13) 2-(2-Acetoxy-1,3-dioxo-2,3-dihydro-1H-inden-2-yl)-4-sec-butylphenyl acetate;
14) 2-(2-Acetoxy-1,3-dioxo-2,3-dihydro-1H-inden-2-yl)-4-tert-butylphenyl acetate;
15) 2-(2-Acetoxy-1,3-dioxo-2,3-dihydro-1H-inden-2-yl)-5-tert-butylphenyl acetate;
16) 2-(2-Acetoxy-1,3-dioxo-2,3-dihydro-1H-inden-2-yl)-3,4,5-trimethylphenyl acetate;
17) 2-(2-Acetoxy-1,3-dioxo-2,3-dihydro-1H-inden-2-yl)-4-tert-pentylphenyl acetate;
18) Acetic acid 2-(2,3-diacetoxy-5-methyl-phenyl)-1,3-dioxo-indan-2-yl ester;
19) Acetic acid 2-(2-acetoxy-4-isopropyl-phenyl)-1,3-dioxo-indan-2-yl ester;
20) 2-(4-Acetyl-2-hydroxy-phenyl)-2-hydroxy-indan-1,3-dione;
21) 2-(1,3-Dioxo-2-(propionyloxy)-2,3-dihydro-1H-inden-2-yl)-5-isopropylphenyl propionate;
22) 2-(2-(Butyryloxy)-1,3-dioxo-2,3-dihydro-1H-inden-2-yl)-5-isopropylphenyl butyrate;
23) 2-(2-Hydroxy-4-isopropylphenyl)-1,3-dioxo-2,3-dihydro-1H-inden-2-yl benzoate;
24) 2-(2-Benzyloxy-4-isopropyl-phenyl)-2-hydroxy-indan-1,3-dione;
25) 2-(2-Benzyloxy-4-isopropyl-phenyl)-2-methoxy-indan-1,3-dione;
26) 2-Hydroxy-2-(4-hydroxy-3,5-dimethyl-phenyl)-indan-1,3-dione;
27) 2-(2-Acetoxy-4-isopropylphenyl)-5-methoxy-1,3-dioxo-2,3-dihydro-1H-inden-2-yl acetate;
28) 2-(2-Hydroxy-4-isopropylphenyl)-2-methoxy-1H-inden-1,3(2H)-dione;
29) 2-(1,3-Dioxo-2-(pivaloyloxy)-2,3-dihydro-1H-inden-2-yl)-5-isopropylphenyl pivalate;

30) 2-(2-Hydroxy-1,3-dioxo-2,3-dihydro-1H-inden-2-yl)-5-isopropylphenyl cinnamate;
31) Dimethyl-carbamic acid 2-(2-dimethylcarbamoyloxy-1,3-dioxo-indan-2-yl)-5-isopropyl-phenyl ester;
32) 2-(2-(Acryloyloxy)-1,3-dioxo-2,3-dihydro-1H-inden-2-yl)-5-isopropylphenyl acrylate;
33) Diethyl-carbamic acid 2-(2-diethylcarbamoyloxy-1,3-dioxo-indan-2-yl)-5-isopropyl-phenyl ester;
34) 2-(2-Hydroxy-1,3-dioxo-2,3-dihydro-1H-inden-2-yl)-5-isopropylphenyl diethylcarbamate;
35) 2-Hydroxy-2-(4-hydroxy-2,5-dimethylphenyl)-1H-inden-1,3(2H)-dione;
36) Acetic acid 2-(2-acetoxy-4-isopropyl-phenyl)-4-amino-1,3-dioxo-indan-2-yl ester;
37) Acetic acid 2-(2-acetoxy-4-isopropyl-phenyl)-4-nitro-1,3-dioxo-indan-2-yl ester;
38) 2-Hydroxy-2-(4-isopropyl-2-methoxyphenyl)-4-nitro-2H-inden-1,3-dione;
39) 2-Chloro-2-(4-isopropyl-2-methoxyphenyl)-4-nitro-2H-inden-1,3-dione;
40) 2-Azido-2-(4-isopropyl-2-methoxyphenyl)-4-nitro-2H-inden-1,3-dione;
41) 4-Amino-2-hydroxy-2-(4-isopropyl-2-methoxyphenyl)-2H-inden-1,3-dione;
42) N-(2-Hydroxy-2-(4-isopropyl-2-methoxyphenyl)-7-nitro-1,3-dioxo-2,3-dihydro-1H-inden-4-yl)acetamide;
43) N-(2-Hydroxy-2-(4-isopropyl-2-methoxyphenyl)-5-nitro-1,3-dioxo-2,3-dihydro-1H-inden-4-yl)acetamide;
44) N-(7-Amino-2-hydroxy-2-(4-isopropyl-2-methoxyphenyl)-1,3-dioxo-2,3-dihydro-1H-inden-4-yl)acetamide;
45) N-(5-Amino-2-hydroxy-2-(4-isopropyl-2-methoxyphenyl)-1,3-dioxo-2,3-dihydro-1H-inden-4-yl)acetamide;
46) 4,7-Diamino-2-hydroxy-2-(4-isopropyl-2-methoxyphenyl)-2H-inden-1,3-dione;
47) 4,5-Diamino-2-hydroxy-2-(4-isopropyl-2-methoxyphenyl)-2H-inden-1,3-dione;
48) Methyl 2-(4-isopropyl-2(methoxycarbonyloxy)phenyl)-1,3-dioxo-2,3-dihydro-1H-inden-2-yl carbamate;
49) 2-(1,3-Dioxo-2-pentanamido-2,3-dihydro-1H-inden-2-yl)-5-isopropylphenyl pentanoate;
50) 2-(2-Isobutylamido-1,3-dioxo-2,3-dihydro-1H-inden-2-yl)-5-isopropylphenyl isobutyrate;
51) 2-Hydroxy-2-(2-hydroxy-4-isopropylphenyl)-2,3-dihydro-1H-inden-1-one;
52) 2-Azido-2-(4-isopropyl-2-methoxyphenyl)-2H-inden-1,3-dione;
53) 2-Amino-2-(4-isopropyl-2-methoxyphenyl)-2H-inden-1,3-dione;
54) N-(2-(4-Isopropyl-2-methoxyphenyl)-1,3-dioxo-2,3-dihydro-1H-inden-2-yl)acetamide;
55) N-(2-(4-Isopropyl-2-methoxyphenyl)-1,3-dioxo-2,3-dihydro-1H-inden-2-yl)benzamide;
56) N-(2-(4-Isopropyl-2-methoxyphenyl)-1,3-dioxo-2,3-dihydro-1H-inden-2-yl)cyclopropancarboxamide;
57) 2-(2-(Methylthio)phenyl)-2H-inden-1,3-dione;
58) 2-(4-(Methylthio)phenyl)-2H-inden-1,3-dione;
59) Methyl 2-(4-isopropyl-2-methoxyphenyl)-1,3-dioxo-2,3-dihydro-1H-inden-2-ylcarbamate;
60) 1-Ethyl-3-(2,3-dihydro-2-(4-isopropyl-2-methoxyphenyl)-1,3-dioxo-1H-inden-2-yl)urea;
61) 1-(2,3-Dihydro-2-(4-isopropyl-2-methoxyphenyl)-1,3-dioxo-1H-inden-2-yl)urea;
62) Isopropyl 2-(4-isopropyl-2-methoxyphenyl)-1,3-dioxo-2,3-dihydro-1H-inden-2-ylcarbamate;
63) 1-(2-(4-Isopropyl-2-methoxyphenyl)-1,3-dioxo-2,3-dihydro-1H-inden-2-yl)-3-methoxy urea;
64) Ethyl 2-(4-isopropyl-2-methoxyphenyl)-1,3-dioxo-2,3-dihydro-1H-inden-2-ylcarbamate;
65) N-(2-Bromo-2-(4-isopropyl-2-methoxyphenyl)-1,3-dioxo-2,3-dihydro-1H-inden-4-yl)acetamide;
66) N-(2-Amino-2-(4-isopropyl-2-methoxyphenyl)-1,3-dioxo-2,3-dihydro-1H-inden-4-yl)acetamide;
67) N,N'-(2-(4-Isopropyl-2-methoxyphenyl)-1,3-dioxo-2,3-dihydro-1H-inden-2,4-diyl)diacetamide;
68) 2-(1,3-Dioxo-2-propionamido-2,3-dihydro-1H-inden-2-yl)-5-isopropylphenyl propionate;
69) 2-(1,3-Dioxo-2-pentanamido-2,3-dihydro-1H-inden-2-yl)-5-isopropylphenyl pentanoate;
70) 2-(2-Benzamido-1,3-dioxo-2,3-dihydro-1H-inden-2-yl)-5-isopropylphenyl benzoate;
71) 2-(2-Acetoxy-1,3-dioxo-2,3-dihydro-1H-inden-2-yl)-6-methylpyridin-3-yl acetate;
72) 2-Hydroxy-2-(4-hydroxy-5-methylpyridin-3-yl)-1H-inden-1,3(2H)-dione;
73) 2-(5-Chloro-3-hydroxypyridin-2-yl)-2-hydroxy-1H-inden-1,3(2H)-dione;
74) 2-2-acetoxy-1,3-dioxo-2,3-dihydro-1H-inden-2-yl;
75) 2-Hydroxy-2-(6-hydroxyquinolin-7-yl)-1H-inden-1,3 (2H)-dione;
76) Butyric acid 2-(2-butyrylamino-1,3-dioxo-indan-2-yl)-5-isopropyl-phenyl ester;
77) Octanoic acid 7-isopropyl-9b-octanoylamino-10-oxo-9b,10-dihydro-5-oxa-indeno[2,1-a]inden-4b-yl ester;
78) Hexanoic acid 2-(2-hexanoylamino-1,3-dioxo-indan-2-yl)-5-isopropyl-phenyl ester;
79) Heptanoic acid 2-(2-heptanoylamino-1,3-dioxo-indan-2-yl)-5-isopropyl-phenyl ester;
80) 2,2-Dimethyl-propionic acid 2-(1,3-dioxo-2-pentanoylamino-indan-2-yl)-5-isopropyl-phenyl ester;
81) 2-(4-Amino-1,3-dioxo-2-pentanamido-2,3-dihydro-1H-inden-2-yl)-5-isopropylphenyl pentanoate;
82) 2-(4-Amino-2-hexanamido-1,3-dioxo-2,3-dihydro-1H-inden-2-yl)-5-isopropylphenyl hexanoate;
83) 2-(4-Amino-2-heptanamido-1,3-dioxo-2,3-dihydro-1H-inden-2-yl)-5-isopropylphenyl heptanoate;
84) 2-(4-Amino-1,3-dioxo-2-propionamido-2,3-dihydro-1H-inden-2-yl)-5-isopropylphenyl propionate;
85) 2-(4-Amino-2-butyramido-1,3-dioxo-2,3-dihydro-1H-inden-2-yl)-5-isopropylphenyl butyrate;
86) N-(2-(2-Hydroxy-1,3-dioxo-2,3-dihydro-1H-inden-2-yl)-4,5-dimethylphenyl)acetamide;
87) N-(2-(2-Hydroxy-1,3-dioxo-2,3-dihydro-1H-inden-2-yl)-4,5-dimethylphenyl)propionamide;
88) N-(5-Ethyl-2-(2-hydroxy-1,3-dioxo-2,3-dihydro-1H-inden-2-yl)phenyl)acetamide;
89) N-(2-(2-Hydroxy-1,3-dioxo-2,3-dihydro-1H-inden-2-yl)-4,5-dimethylphenyl)butyramide;
90) N-(2-(2-Hydroxy-1,3-dioxo-2,3-dihydro-1H-inden-2-yl)-4,5-dimethylphenyl)isobutyramide;
91) 2-(4-Amino-2-octanamido-1,3-dioxo-2,3-dihydro-1H-inden-2-yl)-5-isopropylphenyl octanoate;
92) 2-(2-Acetamido-1,3-dioxo-2,3-dihydro-1H-inden-2-yl)-5-isopropylphenyl methyl carbonate;
93) 2-(2-Acetamido-1,3-dioxo-2,3-dihydro-1H-inden-2-yl)-5-isopropylphenyl pentanoate;
94) N-(2-(4-Acetamido-2-hydroxy-7-nitro-1,3-dioxo-2,3-dihydro-1H-inden-2-yl)-4,5-dimethylphenyl)isobutyramide;
95) N-(2-(2-Hydroxy-1,3-dioxo-2,3-dihydro-1H-inden-2-yl)-5-isopropylphenyl)isobutyramide;
96) 2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate;
97) 2-(2-Acetamido-1,3-dioxo-2,3-dihydro-1H-inden-2-yl)-5-isopropylphenyl methylcarbamate;
98) Dimethyl-carbamic acid 2-(2-acetylamino-1,3-dioxo-indan-2-yl)-5-isopropyl-phenyl ester;
99) Carbonic acid 2-(2-acetylamino-1,3-dioxo-indan-2-yl)-5-isopropyl-phenyl ester phenyl ester;
100) 2-(2-Acetamido-4-amino-1,3-dioxo-2,3-dihydro-1H-inden-2-yl)-5-isopropylphenyl dimethylcarbamate;
101) 2-(2-Acetamido-1,3-dioxo-2,3-dihydro-1H-inden-2-yl)-5-isopropylphenyl ethyl carbonate;
102) Ethyl acetyl(2-(2-hydroxy-4-isopropylphenyl)-1,3-dioxo-2,3-dihydro-1H-inden-2-yl)carbamate;
103) 2-(2-Acetamido-4-amino-1,3-dioxo-2,3-dihydro-1H-inden-2-yl)-5-isopropylphenyl ethylcarbamate;
104) 2-(3-Methoxyphenyl)-2H-inden-1,3-dione;
105) Ethyl (6-(2-((ethoxycarbonyl)oxy)-4-isopropylphenyl)-5,7-dioxo-6,7-dihydro-5H-cyclopenta[b]pyridin-6-yl)carbonate;
106) N-(2-(2-Hydroxy-1,3-dioxo-2,3-dihydro-1H-inden-2-yl)-4,5-dimethoxyphenyl)isobutyramide;
107) N-[2-(4-Amino-2-hydroxy-1,3-dioxo-indan-2-yl)-4,5-dimethoxy-phenyl]-isobutyramide; and
108) N-[2-(2-Hydroxy-5,6-dimethoxy-1,3-dioxo-indan-2-yl)-4,5-dimethoxy-phenyl]-isobutyramide.

Preferred examples of the 1,3-Dioxoindene derivative represented by Chemcial Formula 1 are as follows:
Compounds 27), 36)~48), 53)~56), 59)~70), and 76)~108).

More preferred examples of the 1,3-Dioxoindene derivative represented by Chemical Formula include:
Compounds 6), 19), 21)~23), 30), 32), 36), 48), 49), 68)~70), 76), 78)~85), 92)~97), and 99)~103).

The 1,3-Dioxoindene derivatives, represented by Chemical Formula 1, according to the present invention may be used in the form of pharmaceutical acceptable salts. Useful are acid addition salts formed with pharmaceutically acceptable free acids. As used herein, the term "pharmaceutically acceptable salt" refers to any organic or inorganic salt of the base compounds of Chemical Formula 1, not exhibiting a side effect in which the beneficial activity of the base compounds of Chemical Formula 1 is degraded when it is present at a concentration causing no toxicity and harm in the body. The free acids may be inorganic or organic. examples of useful inorganic free acids include hydrochloric acid, bromic acid, nitric acid, sulfuric acid, perchloric acid and phosphoric acid. As organic acids, citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D)- or (L)-malic acid, maleic acid, methanesulfonic acid, ethanesulfonic acid, 4-toluenesulfonic acid, salicylic acid, benzoic acid, or malonic acid may be used. The pharmaceutically acceptable salts may include alkali metal salts (sodium salt, potassium salt, etc.) and alkaline earth metal salts (calcium salt, magnesium salt, etc.). Acid addition salts useful in the present invention include, but are not limited to, acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, alamine, potassium, sodium, tromethamine, and zinc salt, with hydrochloride or trifluoroacetate being preferred. Addition salts according to the present invention may be prepared by typical methods. For example, they may be prepared by dissolving the compound of Chemical Formula 1 in an organic solvent, such as methanol, ethanol, acetone, methylene chloride, or acetonitrile, and adding an excess of organic acids or an excess of aqueous inorganic acid solutions so as to precipitate or crystallize salts. These addition salts may be obtained by precipitation or crystallization, or by evaporating the solvent or excess acid and drying or suction-filtering the precipitated salt.

Also, pharmaceutically acceptable metal salts formed with bases may fall within the range of pharmaceutically acceptable salts of the compound of the present invention. Examples of the metal salts useful in the present invention include alkali metal salts and alkaline earth metal salts. By way of example, the compound of the present invention may be dissolved in excess alkali metal hydroxide or alkaline earth metal hydroxide in water, and, after the filtration of the solution to remove non-dissolved compound salts, the filtrate may be dried to afford the pharmaceutically acceptable salts of the compound of the present invention. Suitable for use in pharmaceutics are sodium, potassium or calcium salts. Corresponding silver salts may be obtained by reacting the alkali metal or alkaline earth metal salts with suitable silver salt (e.g., silver nitrate).

Not only the 1,3-Dioxoindene derivatives of compound of Chemical Formula 1 and pharmaceutically acceptable salts thereof, but also solvates, hydrates and isomers prepared therefrom, if having the same effect, are within the scope of the present invention.

Also, the present invention is concerned with a method for the preparation of the 1,3-Dioxoindene derivative according to the present invention. In one embodiment, the method comprises acylating or alkylating the compound of Chemical Formula 2 with a base in a solvent to afford a compound of Chemcial Formula 1a (step 1), as illustrated in the following Reaction Scheme 1:

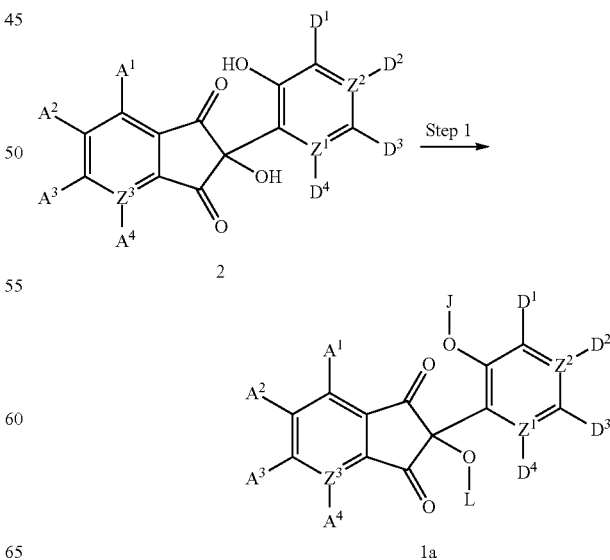

wherein, the compound of Chemical Formula 1a is a derivative of the compound of Chemical Formula 1, a pharmaceutically acceptable salt thereof, or an enantiomer thereof, $A^1, A^2, A^3, A^4, D^1, D^2, D^3, D^4, Z^2$, and $Z^3$ are as defined in Chemical Formula 1, respectively, J and L are, independently or optionally, the same as $A^1, A^2, A^3, A^4, D^1, D^2, D^3$, or $D^4$.

As the solvent useful in Reaction Scheme 1, diisopropylether, diethylether, dioxane, tetrahydrofurane (THF), dimethylformamide (DMF), dimethylacetamide (DMA), dimethylsulfoxide (DMSO), methylene chloride (MC), chlorobenzene, toluene, or benzene may be employed.

The base used in this reaction may be pyridine (PPTs), 4-dimethyl aminopyridine, trimethylamine, or ethyl amine.

In another embodiment, the method comprises:

reacting the compound of Chemcial Formula 2 with thionyl chloride or oxalic chloride in the presence of a base in a solvent and then with ammonia to give a compound of Chemcial Formula 3 (step 1); and acylating or alkylating the compound of Chemcial Formula 3 in the presence of a base in a solvent to afford a compound of Chemical Formula 1b (step 2), as illustrated in the following Reaction Scheme 2:

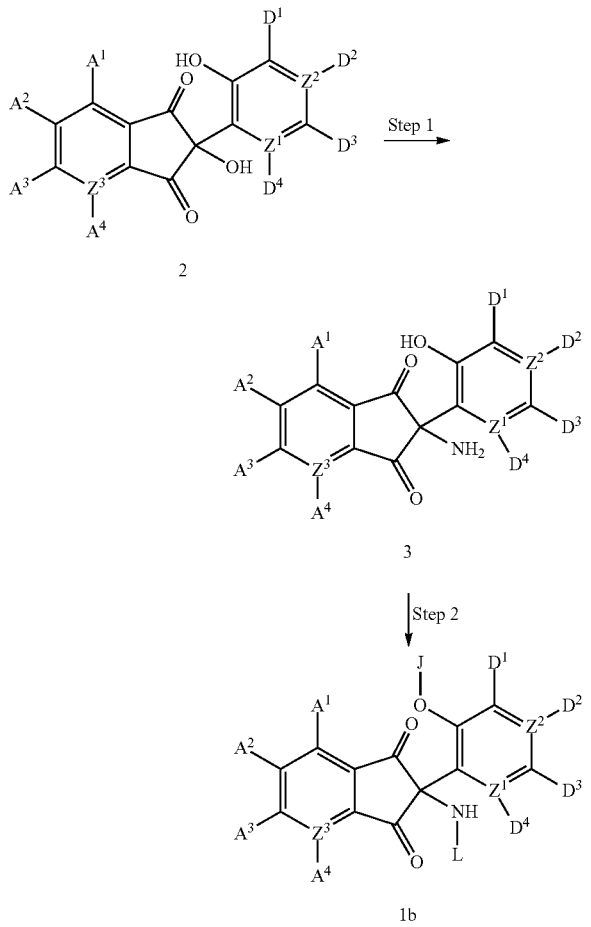

wherein, the compound of Chemical Formula 1b is a derivative of the compound of Chemical Formula 1, a pharmaceutically acceptable salt thereof, or an enantiomer thereof, $A^1, A^2, A^3, A^4, D^1, D^2, D^3, D^4, Z^1, Z^2$, and $Z^3$ are as defined in Chemical Formula 1, respectively, J and L are, independently or optionally, the same as $A^1, A^2, A^3, A^4, D^1, D^2, D^3$, or $D^4$.

The solvents used in steps 1 and 2 in Reaction Scheme 2 of this method may be, independently, selected from the group consisting of diisopropylether, diethylether, dioxane, tetrahydrofurane (THF), dimethylformamide (DMF), dimethylacetamide (DMA), dimethylsulfoxide (DMSO), methylene chloride (MC), chlorobenzene, toluene, and benzene.

As the base for the acylating or alkylating reaction in this method, pyridine (PPTs), trimethylamine, ethylamine, or triphosgene may be used.

Also contemplated in accordance with an aspect of the present invention is a pharmaceutical composition of the prevention or treatment of a viral disease, comprising an 1,3-Dioxoindene derivative represented by Chemical Formula 1, a pharmaceutically acceptable salt thereof, or an enantiomer thereof as an active ingredient.

The viral disease that the pharmaceutical composition of the present invention targets is a disease caused by picornaviruses including coxsackie-, entero-, polio-, and rhinoviruses. Examples of the viral disease include poliomyelitis, paralysis, acute hemorrhagic conjunctivitis, viral meningitis, hand-foot-and-mouth disease, vesicular disease, hepatitis A, myositis, myocarditis, pancreatitis, epidemic myalgia, encephalitis, cold, herpangina, and foot-and-mouth disease.

Having excellent antiviral activity against picornaviruses such as coxsackie-, entero-, echo-, polio- and rhinoviruses as well as exhibiting low cytotoxicity, the 1,3-Dioxoindene derivative of Chemical Formula 1 can be useful as an active ingredient of a pharmaceutical composition for the prevention or treatment of various viral diseases including poliomyelitis, paralysis, acute hemorrhagic conjunctivitis, viral meningitis, hand-foot-and-mouth disease, vesicular disease, hapatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis, and otitis media.

Clinically, the compound of the present invention may be administered in the form of various formulations. For this, the compound is usually formulated in combination with a diluent or excipient, such as a filler, a thickening agent, a binder, a wetting agent, a disintegrant, a surfactant, etc.

Solid preparations intended for oral administration of the compound of the present invention may take the form of tablets, pills, powders, granules, capsules, troches, and the like. These solid preparations are formulated in combination with at least one excipient such as starch, calcium carbonate, sucrose, lactose, or gelatine. In addition to a simple excipient, a lubricant such as magnesium stearate, talc, or the like may also be added. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations for the oral administration of the compound of the present invention.

Also, the compound of the present invention may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

The compound of the present invention is administered in a therapeutically effective amount. The effective dose of the compound of the present invention varies depending on various factors including a patient's age, weight, sex, and health condition, the route of administration, and the severity of disease. Typically, the compound of the present invention may be administered at a daily dose of from 0.001 to 100 mg/kg, and preferably at a daily dose of from 0.01 to 35 mg/kg. For an adult with a weight of 70 kg, the dose of the compound of the present invention may typically range from 0.07 to 7,000 mg/day, and preferably from 0.7 to 2,500 mg/day. The formulations of the compound may be administered in a single dose or may be divided into multiple doses at regular intervals of time according to the instructions of a physician or pharmacist who is responsible for monitoring or observing the administration of the drug.

MODE FOR INVENTION

A better understanding of the present invention may be obtained through the following examples which are set forth to illustrate, but are not to be construed as limiting the present invention.

Example 1

Ethyl 2-(4-acetoxy-3-(2-acetoxy-1,3-dioxo-2,3-dihydro-1H-inden-2-yl)-5-methoxyphenyl)acetate Ethyl 2-(4b,9b-dihydroxy-6-methoxy-10-oxo-9b,10-dihydro-4bH-benzo[d]indeno[1,2-b]furan-8-yl)acetate (0.50 g, 1.4 mmol) was completely dissolved in anhydrous dichloromethane (30 ml). This solution was added with anhydrous acetic acid (0.37 ml, 3.9 mmol), pyridine (0.11 ml, 1.4 mmol), and 4-dimethyl aminopyridine (0.05 g), and stirred at room temperature for 3 hrs. After the reaction mixture was extracted with dichloromethane, the organic layer was concentrated and purified using column chromatography (ethylacetate:hexane=1:2) to afford the title compound (0.03 g, 4%).

mp: 102-107° C.
$^1$H-NMR (300 MHz, CDCl$_3$) δ 1.25 (t, J=7.2 Hz, 3H, CH3) 1.98 (s, 3H, OAc) 2.19 (s, 3H, OAc) 3.60 (s, 2H, CH2) 3.73 (s, 3H OCH3) 4.12-4.19 (q, J=7.2, 14.4 Hz, 2H, CH2) 6.93 (s, 1H, ArH) 7.23 (s, 1H, ArH) 7.85-8.00 (m, 4H, ArH). MS(EI): 454.

Example 2

2-(2-Acetoxy-1,3-dioxo-2,3-dihydro-1H-inden-2-yl)-4,5-dimethylphenyl acetate 4b,9b-Dihydroxy-7,8-dimethyl-4bH-benzo[d]indeno[1,2-b]-furan-10(9bH)-one (1.00 g, 3.5 mmol) was dissolved in anhydrous THF (50 ml). This solution was added with anhydrous acetic acid (0.67 ml, 7.1 mmol), pyridine (0.30 ml, 3.5 mmol), and 4-dimethyl aminopyridine (0.1 g), and stirred at room temperature for 3 hrs. After the reaction mixture was extracted with dichloromethane, the organic layer was concentrated and purified using column chromatography (ethylacetate:hexane=1:4) to afford the title compound (0.55 g, 42%).

mp: 206-207° C.
$^1$H-NMR (300 MHz, CDCl$_3$) δ 2.05 (s, 3H, CH$_3$) 2.19 (s, 3H, OAc) 2.23 (s, 3H, OAc) 6.74 (s, 1H, ArH) 7.44 (s, 1H, ArH) 7.83-8.00 (m, 4H, ArH). MS(EI): 366.

Example 3

2-(2-Acetoxy-1,3-dioxo-2,3-dihydro-1H-inden-2-yl)-5-chlorophenyl acetate

7-Chloro-4b,9b-dihydroxy-4bH-benzo[d]indeno[1,2-b]-furan-10(9bH)-one (2.00 g, 6.9 mmol) was completely dissolved in anhydrous THF (20 ml). This solution was added with anhydrous acetic acid (1.41 ml, 13.8 mmol), pyridine (0.55 ml, 6.9 mmol), and 4-dimethyl aminopyridine (0.2 g), and stirred at room temperature for 12 hrs. After the reaction mixture was extracted with dichloromethane, the organic layer was concentrated and purified using column chromatography (ethylacetate:hexane=1:3) to afford the title compound (0.51 g, 19%).

mp: 148-150° C.
$^1$H-NMR (300 MHz, CDCl$_3$) δ 2.04 (s, 3H, OAc) 2.20 (s, 3H, OAc) 7.04 (d, J=2.1 Hz, 1H, ArH) 7.30 (d, J=1.8 Hz, 1H, ArH) 7.68 (d, J=9.0 Hz, 1H, ArH) 7.89-7.93 (m, 2H, ArH) 7.99-8.03 (m, 2H, ArH). MS(EI): 372.

Example 4

6-(2-Acetoxy-1,3-dioxo-2,3-dihydro-1H-inden-2-yl)-2,3-dichlorophenyl acetate 2-(3,4-Dichloro-2-hydroxyphenyl)-2-hydroyx-1H-inden-1,3(2H)-dione (2.00 g, 6.9 mmol) was completely dissolved in anhydrous THF (20 ml). This solution was added with anhydrous acetic acid (1.41 ml, 13.8 mmol), pyridine (0.55 ml, 6.9 mmol), and 4-dimethyl aminopyridine (0.2 g), and stirred at room temperature for 12 hrs. After the reaction mixture was extracted with dichloromethane, the organic layer was concentrated and purified using column chromatography (ethylacetate:hexane=1:4 to 1:2.5) to afford the title compound (0.037 g, 1.5%).

mp: 129-136° C.
$^1$H-NMR (300 MHz, CDCl$_3$) δ 2.07 (s, 3H, OAc) 2.19 (s, 3H, OAc) 7.42 (d, J=8.8 Hz, 1H, ArH) 7.64 (d, J=8.7 Hz, 1H, ArH) 7.89-8.03 (m, 4H, ArH). MS(EI): 407.

Example 5

2-(2-Acetoxy-1,3-dioxo-2,3-dihydro-1H-inden-2-yl)-4,6-dichlorophenyl acetate 2-(3,5-Dichloro-2-hycroxyphenyl)-2-hydroxy-1H-inden-1,3(2H)-dione (1.50 g, 4.6 mmol) was completely dissolved in anhydrous THF (20 ml). This solution was added with anhydrous acetic acid (0.95 ml, 9.28 mmol), pyridine (0.37 ml, 4.6 mmol), and 4-dimethyl aminopyridine (0.15 g), and stirred at room temperature for 12 hrs. After the reaction mixture was extracted with dichloromethane, the organic layer was concentrated and purified using column chromatography (ethylacetate:hexane=1:4) to afford the title compound (80 g, 4.2%).

mp: 178-180° C.
$^1$H-NMR (200 MHz, CDCl$_3$) δ 2.07 (s, 3H, OAc) 2.20 (s, 3H, OAc) 7.48 (d, J=3.6 Hz, 1H, ArH) 7.72 (d, J=3.3 Hz, 1H, ArH) 7.92-8.08 (m, 4H, ArH). MS(EI): 407.

Example 6

2-(2-Acetoxy-1,3-dioxo-2,3-dihydro-1H-inden-2-yl)-5-ethylphenyl acetate

7-Ethyl-4b,9b-dihydroxy-4bH-benzo[d]indeno[1,2-b]-furan-10(9bH)-one (2.00 g, 7.0 mmol) was completely dissolved in anhydrous THF (20 ml). This solution was added with anhydrous acetic acid (1.44 ml, 14.1 mmol), pyridine (0.56 ml, 7.0 mmol), and 4-dimethyl aminopyridine (0.2 g), and stirred at room temperature for 12 hrs. After the reaction mixture was extracted with dichloromethane, the organic layer was concentrated and purified using column chromatography (ethylacetate:hexane=1:4) to afford the title compound (2.28 g, 88%).

mp: 136-137° C.

$^1$H-NMR (300 MHz, CDCl$_3$) δ 1.19 (t, J=7.6 Hz, 3H, CH$_3$) 2.08 (s, 3H, OAc) 2.19 (s, 3H, OAc) 2.57-2.64 (q, J=15.3 Hz, J=7.8 Hz, 2H, CH$_2$) 6.81 (s, 1H, ArH) 7.11 (d, J=9.0 Hz, 1H, ArH) 7.59 (d, J=8.4 Hz, 1H, ArH) 7.86-7.90 (m, 2H, ArH) 7.97-8.01 (m, 2H, ArH). MS(EI): 366.

Example 7

2-(2-Acetoxy-1,3-dioxo-2,3-dihydro-1H-inden-2-yl)-4-methoxyphenyl acetate 4b,9b-Dihydroxy-8-methyl-4bH-benzo[d]indeno[1,2-b]-furan-10(9bH)-one (3.03 g, 10.6 mmol) was dissolved in anhydrous THF (20 ml). This solution was added with anhydrous acetic acid (2.01 g, 21.3 mmol), pyridine (0.84 ml, 10.6 mmol), and 4-dimethyl aminopyridine (0.3 g), and stirred at room temperature for 12 hrs. After the reaction mixture was extracted with dichloromethane, the organic layer was concentrated and purified using column chromatography (ethylacetate:hexane=1:3 to 1:2.5) to afford the title compound (0.44 g, 11%).

mp: 184-186° C.

$^1$H-NMR (300 MHz, CDCl$_3$) δ 2.15 (s, 3H, OAc) 2.17 (s, 3H, OAc) 3.78 (s, 3H, OCH$_3$) 6.78 (d, J=8.7 Hz, 1H, ArH) 6.91 (dd, J=2.7, 9.0 Hz, 1H, ArH) 7.12 (d, J=2.7 Hz, 1H, ArH) 7.60 (t, J=7.5 Hz, 1H, ArH) 7.76-7.85 (m, 2H, ArH) 8.14 (d, J=7.8 Hz, 1H, ArH). MS(EI): 368.

Example 8

4-(2-Acetoxy-1,3-dioxo-2,3-dihydro-1H-inden-2-yl) biphenyl-3-yl acetate 4b,9b-Dihydroxy-7-phenyl-4bH-benzo[d]indeno[1,2-b]-furan-10(9bH)-one (2.00 g, 6.0 mmol) was dissolved in anhydrous THF (20 ml). This solution was added with anhydrous acetic acid (1.24 ml, 12.1 mmol), pyridine (0.48 ml, 6.0 mmol), and 4-dimethyl aminopyridine (0.2 g), and stirred at room temperature for 12 hrs. After the reaction mixture was extracted with dichloromethane, the organic layer was concentrated and purified using column chromatography (ethylacetate:hexane=1:4) to afford the title compound (0.41 g, 11%).

mp: 165-167° C.

$^1$H-NMR (300 MHz, CDCl$_3$) δ 2.05 (s, 3H, OAc) 2.22 (s, 3H, OAc) 7.20 (s, 1H, ArH) 7.33-7.43 (m, 3H, ArH) 7.51 (d, J=6.0 Hz, 3H, ArH) 7.78 (dd, J=8.4 Hz, J=1.8 Hz, 1H, ArH) 7.88-7.92 (m, 2H, ArH) 8.01-8.05 (m, 2H, ArH). MS(EI): 414.

Example 9

2-(2-Acetoxy-1,3-dioxo-2,3-dihydro-1H-inden-2-yl)-4-nitrophenyl acetate 4b,9b-Dihydroxy-8-nitro-4bH-benzo[d]indeno[1,2-b]-furan-10(9bH)-one (0.80 g, 2.6 mmol) was dissolved in anhydrous THF (20 ml). This solution was added with anhydrous acetic acid (0.54 ml, 5.3 mmol), pyridine (0.21 ml, 2.6 mmol), and 4-dimethyl aminopyridine (0.08 g), and stirred at room temperature for 30 hrs. After the reaction mixture was extracted with dichloromethane, the organic layer was concentrated and purified using column chromatography (ethylacetate:hexane=1:2 to 1:1) to afford the title compound (0.44 g, 11%).

mp: 163-167° C.

$^1$H-NMR (300 MHz, CDCl$_3$) δ 1.92 (s, 3H, OAc) 2.24 (s, 3H, OAc) 7.22 (d, J=9.0 Hz, 1H, ArH) 7.93-7.97 (m, 2H, ArH) 8.03-8.08 (m, 2H, ArH) 8.24 (dd, J=8.4 Hz, J=3.0 Hz, 1H, ArH) 8.72 (d, J=2.7 Hz, 1H, ArH). MS(EI): 383.

Example 10

3-(2-Acetoxy-1,3-dioxo-2,3-dihydro-1H-inden-2-yl) biphenyl-4-yl acetate 4b,9b-Dihydroxy-8-phenyl-4bH-benzo[d]indeno[1,2-b]-furan-10(9bH)-one (1.00 g, 3.0 mmol) was dissolved in anhydrous THF (20 ml). This solution was added with anhydrous acetic acid (0.62 ml, 6.0 mmol), pyridine (0.25 ml, 3.0 mmol), and 4-dimethyl aminopyridine (0.1 g), and stirred at room temperature for 30 hrs. After the reaction mixture was extracted with dichloromethane, the organic layer was concentrated and purified using column chromatography (ethylacetate:hexane=1:4) to afford the title compound (0.12 g, 6%).

mp: 196-198° C.

$^1$H-NMR (300 MHz, CDCl$_3$) δ 2.08 (s, 3H, OAc) 2.22 (s, 3H, OAc) 7.06 (d, J=8.4 Hz, 1H, ArH) 7.35-7.48 (m, 3H, ArH) 7.54-7.58 (m, 3H, ArH) 7.88-7.92 (m, 3H, ArH) 8.00-8.04 (m, 2H, ArH). MS(EI): 414.

Example 11

2-(2-Acetoxy-1,3-dioxo-2,3-dihydro-1H-inden-2-yl)-4-propylphenyl acetate 4b,9b-Dihydroxy-8-propyl-4bH-benzo[d]indeno[1,2-b]-furan-10(9bH)-one (0.80 g, 2.70 mmol) was dissolved in anhydrous THF (20 ml). This solution was added with anhydrous acetic acid (0.55 ml, 5.40 mmol), pyridine (0.21 ml, 2.7 mmol), and 4-dimethyl aminopyridine (0.08 g), and stirred at room temperature for 12 hrs. After the reaction mixture was extracted with dichloromethane, the organic layer was concentrated and purified using column chromatography (ethylacetate:hexane=1:4) to afford the title compound (0.85 g, 56%).

mp: 108-111° C.

$^1$H-NMR (300 MHz, CDCl$_3$) δ 0.96 (t, J=8.0 Hz, 3H, CH$_3$) 1.55-1.70 (m, 2H, CH$_2$) 2.08 (s, 3H, OAc) 2.24 (s, 3H, OAc) 2.61 (t, J=8.4 Hz, 2H, CH$_2$) 6.92 (d, J=8.2 Hz, 1H, ArH) 7.28 (s, 1H, ArH) 7.55 (m, 1H, ArH) 7.78-8.07 (m, 4H, ArH). MS(EI): 380.

Example 12

2-(2-Acetoxy-1,3-dioxo-2,3-dihydro-1H-inden-2-yl)-4-ethylphenyl acetate

8-Ethyl-4b,9b-dihydroxy-4bH-benzo[d]indeno[1,2-b]-furan-10(9bH)-one (0.80 g, 2.70 mmol) was completely dissolved in anhydrous THF (20 ml). This solution was added with anhydrous acetic acid (0.57 ml, 5.66 mmol), pyridine (0.22 ml, 2.83 mmol), and 4-dimethyl aminopyridine (0.08 g), and stirred at room temperature for 12 hrs. After the reaction mixture was extracted with dichloromethane, the organic layer was concentrated and purified using column chromatography (ethylacetate:hexane=1:4 to 1:2) to afford the title compound (0.56 g, 27%).

mp: 153-154° C.

$^1$H-NMR (300 MHz, CDCl$_3$) δ 1.25 (t, J=7.2 Hz, 3H, CH$_3$) 2.16 (s, 3H, OAc) 2.20 (s, 3H, OAc) 2.61-2.69 (q, J=15.0, 7.5 Hz, 2H, CH$_2$) 6.89 (d, J=8.4 Hz, 1H, ArH) 7.20 (d, J=8.4 Hz, 1H, ArH) 7.53 (s, 1H, ArH) 7.86-7.90 (m, 2H, ArH) 7.98-8.02 (m, 2H, ArH). MS(EI): 366.

Example 13

2-(2-Acetoxy-1,3-dioxo-2,3-dihydro-1H-inden-2-yl)-4-sec-butylphenyl acetate 8-sec-Butyl-4b,9b-dihydroxy-4bH-benzo[d]indeno[1,2-b]-furan-10(9bH)-one (0.58 g, 1.8 mmol) was completely dissolved in anhydrous THF (10 ml). This solution was added with anhydrous acetic acid (0.39 ml, 3.7 mmol), pyridine (0.15 ml, 1.8 mmol), and 4-dimethyl aminopyridine (0.06 g), and stirred at room temperature for 12 hrs. After the reaction mixture was extracted with dichloromethane, the organic layer was concentrated and purified using column chromatography (ethylacetate:hexane=1:4 to 1:2) to afford the title compound (0.70 g, 48%).

mp: 118-120° C.

$^1$H-NMR (300 MHz, CDCl$_3$) δ 0.82 (t, J=9.0 Hz, 3H, CH$_3$) 1.21 (d, J=6.9 Hz, 3H, CH$_3$) 1.52-1.61 (m, 2H, CH$_2$) 2.06 (s, 3H, OAc) 2.21 (s, 3H, OAc) 2.59-2.66 (m, 1H, CH) 6.90 (d, J=8.4 Hz, 1H, ArH) 7.20 (dd, J=2.1, 8.4 Hz, 1H, ArH) 7.50 (d, J=1.8 Hz, 1H, ArH) 7.87-7.91 (m, 2H, ArH) 7.98-8.03 (m, 2H, ArH). MS(EI): 394.

Example 14

2-(2-Acetoxy-1,3-dioxo-2,3-dihydro-1H-inden-2-yl)-4-tert-butylphenyl acetate 8-tert-Butyl-4b,9b-dihydroxy-4bH-benzo[d]indeno[1,2-b]-furan-10(9bH)-one (0.50 g, 1.6 mmol) was completely dissolved in anhydrous THF (10 ml). This solution was added with anhydrous acetic acid (0.32 ml, 3.7 mmol), pyridine (0.13 ml, 1.8 mmol), and 4-dimethyl aminopyridine (0.05 g), and stirred at room temperature for 12 hrs. After the reaction mixture was extracted with dichloromethane, the organic layer was concentrated and purified using column chromatography (ethylacetate:hexane=1:4 to 1:2) to afford the title compound (0.44 g, 36%).

mp: 195-196° C.

$^1$H-NMR (300 MHz, CDCl$_3$) δ 1.29 (s, 9H, CH$_3$) 2.14 (s, 3H, OAc) 2.18 (s, 3H, OAc) 6.80 (d, J=8.7 Hz, 1H, ArH) 7.37-7.40 (dd, J=2.1, 8.7 Hz, 1H, ArH) 7.52-7.61 (m, 2H, ArH) 7.75-7.85 (m, 2H, ArH) 8.16 (d, J=8.1 Hz, 1H, ArH). MS(EI): 394.

Example 15

2-(2-Acetoxy-1,3-dioxo-2,3-dihydro-1H-inden-2-yl)-5-tert-butylphenyl acetate 7-sec-Butyl-4b,9b-dihydroxy-4bH-benzo[d]indeno[1,2-b]-furan-10(9bH)-one (0.52 g, 1.67 mmol) was completely dissolved in anhydrous THF (20 ml). This solution was added with anhydrous acetic acid (0.34 ml, 3.3 mmol), pyridine (0.13 g, 1.6 mmol), and 4-dimethyl aminopyridine (0.05 g), and stirred at room temperature for 12 hrs. After the reaction mixture was extracted with dichloromethane, the organic layer was concentrated and purified using column chromatography (ethylacetate:hexane=1:4 to 1:2) to afford the title compound (0.53 g, 42%).

mp: 119-120° C.

$^1$H-NMR (300 MHz, CDCl$_3$) δ 1.25 (s, 9H, CH$_3$) 2.04 (s, 3H, OAc) 2.10 (s, 3H, OAc) 6.95 (d, J=2.1 Hz, 1H, ArH) 7.29 (dd, J=8.4, 2.1 Hz, 1H, ArH) 7.60 (d, J=8.4 Hz, 1H, ArH) 7.84-7.90 (m, 2H, ArH) 7.97-8.02 (m, 2H, ArH). MS(EI): 394.

Example 16

2-(2-Acetoxy-1,3-dioxo-2,3-dihydro-1H-inden-2-yl)-3,4,5-trimethylphenyl acetate 4b,9b-Dihydroxy-8-propyl-4bH-benzo[d]indeno[1,2-b]-furan-10(9bH)-one (0.69 g, 2.33 mmol) was dissolved in anhydrous THF (20 ml). This solution was added with anhydrous acetic acid (0.48 ml, 4.66 mmol), pyridine (0.18 g, 2.33 mmol), and 4-dimethyl aminopyridine (0.07 g), and stirred at room temperature for 12 hrs. After the reaction mixture was extracted with dichloromethane, the organic layer was concentrated and purified using column chromatography (ethylacetate:hexane=1:4 to 1:1) to afford the title compound (0.016 g, 2%).

mp: 238-242° C.

$^1$H-NMR (300 MHz, CDCl$_3$) δ 2.05 (s, 6H, CH$_3$) 2.22 (s, 6H, OAc) 2.59 (s, 3H, CH$_3$) 6.54 (s, 1H, ArH) 7.56 (t, J=7.5 Hz, 1H, ArH) 7.78 (t, J=7.5 Hz, 2H, ArH) 7.94 (d, J=6.6 Hz, 1H, ArH). MS(EI): 380.

Example 17

2-(2-Acetoxy-1,3-dioxo-2,3-dihydro-1H-inden-2-yl)-4-tert-pentylphenyl acetate 4b,9b-Dihydroxy-8-tert-pentyl-4bH-benzo[d]indeno[1,2-b]-furan-10(9bH)-one (0.80 g, 2.46 mmol) was dissolved in anhydrous THF (20 ml). This solution was added with anhydrous acetic acid (0.50 g, 4.93 mmol), pyridine (0.19 ml, 2.46 mmol), and 4-dimethyl aminopyridine (0.08 g), and stirred at room temperature for 12 hrs. After the reaction mixture was extracted with dichloromethane, the organic layer was concentrated and purified using column chromatography (ethylacetate:hexane=1:3) to afford the title compound (0.71 g, 38%).

mp: 146-151° C.

$^1$H-NMR (300 MHz, CDCl$_3$) δ 0.68 (t, J=7.5 Hz, 3H, CH$_3$) 1.26 (s, 6H, CH$_3$) 1.56-1.66 (m, 2H, CH$_2$) 2.06 (s, 3H, OAc) 2.20 (s, 3H, OAc) 6.90 (d, J=8.7 Hz, 1H, ArH) 7.31 (dd, J=8.7 Hz, 2.7 Hz, 1H, ArH) 7.64 (d, J=2.4 Hz, 1H, ArH) 7.86-7.91 (m, 2H, ArH) 7.98-8.02 (m, 2H, ArH). MS(EI)=408.

Example 18

Acetic acid 2-(2,3-diacetoxy-5-methyl-phenyl)-1,3-dioxo-indan-2-yl ester 4b,6,9b-Trihydroxy-8-methyl-4b,9b-dihydro-5-oxa-indeno[1,2-a]-inden-10-one (0.50 g, 1.70 mmol) was dissolved in anhydrous THF (20 ml). This solution was added with anhydrous acetic acid (0.36 g, 3.5 mmol), pyridine (0.14 ml, 1.7 mmol), and 4-dimethyl aminopyridine (0.05 g), and stirred at room temperature for 12 hrs. After the reaction mixture was extracted with dichloromethane, the organic layer was concentrated and purified using column chromatography (ethylacetate:hexane=1:2) to afford the title compound (0.47 g, 65%).

mp: 192-194° C.

$^1$H-NMR (300 MHz, CDCl$_3$) δ 2.08 (s, 3H, OAc) 2.17 (s, 3H, OAc) 2.19 (s, 3H, OAc) 2.35 (s, 3H, CH$_3$) 7.06 (s, 1H, ArH) 7.35 (s, 1H, ArH) 7.86-7.89 (m, 2H, ArH) 7.98-8.01 (m, 2H, ArH). MS(EI): 410.

Example 19

Acetic acid 2-(2-acetoxy-4-isopropyl-phenyl)-1,3-dioxo-indan-2-yl ester 4b,9b-Dihydroxy-7-isopropyl-4b,9b-dihydro-5-oxa-indeno[2,1-a]-inden-10-one (0.80 g, 2.70 mmol) was dissolved in anhydrous THF (100 ml). This solution was added with anhydrous acetic acid (11.46 g, 121.4 mmol), pyridine (4.9 g, 60.7 mmol), and 4-dimethyl aminopyridine (1.8 g), and stirred at room temperature for 12 hrs. After the reaction mixture was extracted with dichloromethane, the organic layer was concentrated and purified using column chromatography (ethylacetate:hexane=1:4) to afford the title compound (19.0 g, 82%).

mp: 136-137° C.

$^1$H-NMR (300 MHz, CDCl$_3$) δ 1.18 (d, J=6.9 Hz, 6H, CH$_3$) 2.09 (s, 3H, OAc) 2.20 (s, 3H, OAc) 2.83-2.88 (q, J=6.9 Hz, 1H, CH) 6.83 (d, J=1.6 Hz, 1H, ArH) 7.14 (dd, J=8.4 Hz, J=1.8 Hz, 1H, ArH) 7.59 (d, J=8.4 Hz, 1H, ArH) 7.77-7.88 (m, 2H, ArH) 7.97-8.01 (m, 2H, ArH). MS(EI): 380.

Example 20

2-(4-Acetyl-2-hydroxy-phenyl)-2-hydroxy-indan-1,3-dione

To a solution of ninhydrin (1.00 g, 5.61 mmol) in acetic acid (20 ml) was added 1-(3-hydroxy-phenyl)-ethanone (0.76 g, 5.61 mmol), followed by heating for 3 hrs at 110° C. The reaction mixture was diluted with methylene chloride, extracted with 2N NaOH aqueous solution, and the concentrated organic layer was purified using column chromatography (ethylacetate:hexane=1:2) to afford the title compound (White, 1.32 g, 79%).

mp: 177-180° C.

$^1$H-NMR (300 MHz, CDCl$_3$) δ 3.87 (s, 3H, CH$_3$) 7.07 (d, J=7.0 Hz, 1H, ArH) 7.32 (d, J=7.9 Hz, 1H, ArH) 7.43 (d, J=8.1 Hz, 1H, ArH) 7.91-7.94 (q, J=5.7, 3.0 Hz, 2H, ArH) 8.06-8.08 (q, J=5.7, 3.0 Hz, 2H, ArH). MS(EI): 296.

Example 21

2-(1,3-Dioxo-2-(propionyloxy)-2,3-dihydro-1H-inden-2-yl)-5-isopropylphenyl propionate 2-hydroxy-2-(2-hydroxy-4-isopropyl-phenyl)-indan-1,3-dione (1.00 g, 3.37 mmol) was completely dissolved in anhydrous THF (20 ml). This solution was added with propionyl chloride (0.62 g, 6.74 mmol), and triethylamine (0.41 g, 4.04 mmol), followed by heating 12 hrs under reflux. After the reaction mixture was concentrated, extracted with dichloromethane, and the organic layer was concentrated and purified using column chromatography (ethylacetate:hexane=1:4) to afford the title compound (White, 0.23 g, 17%).

mp: 123-125° C.

$^1$H-NMR (300 MHz, CDCl$_3$) δ 1.10-1.19 (m, 12H, CH$_3$) 2.31-2.39 (q, J=15.0, 7.5 Hz, 2H, CH$_2$) 2.46-2.54 (q, J=15.0, 7.5 Hz, 2H, CH$_2$) 2.80-2.89 (m, 1H, CH) 6.82 (s, 1H, ArH) 7.14 (d, J=8.4 Hz, 1H, ArH) 7.61 (d, J=8.1 Hz, 1H, ArH) 7.83-7.86 (m, 2H, ArH) 7.95-7.99 (m, 2H, ArH). MS(EI)= 408.

Example 22

2-(2-(Butyryloxy)-1,3-dioxo-2,3-dihydro-1H-inden-2-yl)-5-isopropylphenyl butyrate 2-hydroxy-2-(2-hydroxy-4-isopropyl-phenyl)-indan-1,3-dione (1.00 g, 3.37 mmol) was completely dissolved in anhydrous methylene chloride (20 ml). This solution was added with butyryl chloride (0.72 g, 6.74 mmol), and triethylamine (0.41 g, 4.04 mmol), followed by heating 24 hrs under reflux. After the reaction mixture was concentrated, extracted with dichloromethane, and the organic layer was concentrated and purified using column chromatography (ethylacetate:hexane=1:2) to afford the title compound (White, 0.20 g, 14%).

mp: 98-102° C.

$^1$H-NMR (300 MHz, CDCl$_3$) δ 0.94-1.02 (m, 6H, CH$_3$) 1.17 (s, 3H, CH$_3$) 1.20 (s, 3H, CH$_3$) 1.59-1.73 (m, 4H, CH$_2$) 2.29 (t, J=7.2 Hz, 2H, CH$_2$) 2.45 (t, J=7.5 Hz, 2H, CH$_2$) 2.81-2.90 (m, 1H, CH) 6.80 (s, 1H, ArH) 7.13 (dd, J=8.4 Hz, 1.4H, 1H, ArH) 7.60 (d, J=8.4 Hz, 1H, ArH) 7.85-7.89 (m, 2H, ArH) 7.96-8.01 (m, 2H, ArH). MS(EI): 436.

Example 23

2-(2-Hydroxy-4-isopropylphenyl)-1,3-dioxo-2,3-dihydro-1H-inden-2-yl benzoate 2-hydroxy-2-(2-hydroxy-4-isopropyl-phenyl)-indan-1,3-dione (1.00 g, 3.37 mmol) was completely dissolved in anhydrous methylene chloride (20 ml). This solution was added with benzoyl chloride (0.94 g, 6.74 mmol), triethylamine (0.41 g, 4.04 mmol), and DMPA (0.01 g), followed by heating 24 hrs under reflux. After the reaction mixture was concentrated, extracted with dichloromethane, and the organic layer was concentrated and purified using column chromatography (ethylacetate:hexane=1:4) to afford the title compound (0.81 g, 14%).

mp: 117-119° C.

$^1$H-NMR (300 MHz, CDCl$_3$) δ 1.19-1.28 (m, 6H, CH$_3$) 2.84-2.97 (m, 1H, CH) 6.91-8.09 (m, 12H, ArH). MS(EI): 400.

Example 24

2-(2-Benzyloxy-4-isopropyl-phenyl)-2-hydroxy-indan-1,3-dione 4b,9b-dihydroxy-7-isopropyl-4b,9b-dihydroxy-5-oxa-indeno[2,1-a]inden-10-one (0.50 g, 1.68 mmol) was completely dissolved in anhydrous DMF (10 ml). This solution was added with potassium carbonate (0.46 g, 3.26 mmol) and benzyl bromide (0.26 g, 1.51 mmol), and stirred at room temperature for 13 hrs. The reaction mixture was washed with 1N NaOH, extracted with dichloromethane, and the concentrated organic layer was purified using column chromatography (ethylacetate:hexane=1:4) to afford the title compound (0.40 g, 61%).

mp: 197-199° C.

$^1$H-NMR (300 MHz, CDCl$_3$) δ 1.21 (d, J=6.9 Hz, 6H, CH$_3$) 2.83-2.93 (m, 1H, CH) 3.04 (s, 1H, OH) 4.67 (s, 2H, OCH$_2$) 6.69 (s, 1H, ArH) 6.91 (d, J=7.5 Hz, 2H, ArH) 6.99 (d, J=8.1

Hz, 1H, ArH) 7.11-7.23 (m, 3H, ArH) 7.57-7.60 (m, 2H, ArH) 7.61-7.71 (m, 3H, ArH). MS(EI): 386.

Example 25

2-(2-Benzyloxy-4-isopropyl-phenyl)-2-methoxy-indan-1,3-dione 2-(2-benzyloxy-4-isopropyl-phenyl)-2-hydroxy-indan-1,3-dione (0.10 g, 0.25 mmol) was completely dissolved in anhydrous DMF (2 ml). This solution was added with sodium hydride (0.007 g, 0.31 mmol) and methyl iodide (0.04 g, 0.28 mmol), and stirred at room temperature for 13 hrs. The reaction mixture was extracted with dichloromethane, and the concentrated organic layer was purified using column chromatography (ethylacetate:hexane=1:4) to afford the title compound (12 mg, 12%).
mp: 140-144° C.
$^1$H-NMR (300 MHz, CDCl$_3$) δ 1.21 (d, J=6.9 Hz, 6H, CH$_3$) 2.82-2.92 (m, 1H, CH) 3.44 (s, 1H, OCH$_3$) 4.63 (s, 2H, OCH$_2$) 6.68 (s, 1H, ArH) 6.88 (d, J=7.8 Hz, 2H, ArH) 6.99 (d, J=8.1 Hz, 1H, ArH) 7.09-7.21 (m, 3H, ArH) 7.54-7.58 (m, 2H, ArH) 7.63-7.70 (m, 3H, ArH). MS(EI): 400.

Example 26

2-Hydroxy-2-(4-hydroxy-3,5-dimethyl-phenyl)-indan-1,3-dione

Ninhydrin (1.00 g, 5.61 mmol) and 2,6-dimethylphenol (686 mg, 5.61 mmol) was dissolved in acetic acid (15 ml), and this solution was heated for 13 hrs. The reaction mixture was concentrated, and extracted with dichloromethane, and then concentrated organic layer was purified using column chromatography (ethylacetate:hexane=1:2) to afford the title compound (0.31 g, 20%).
mp: 210-213° C.
$^1$H-NMR (300 MHz, CDCl$_3$) δ 2.16 (s, 6H, CH$_3$) 3.27 (s, 1H, OH) 4.81 (s, 1H, OH) 7.02 (s, 2H, ArH) 7.90-7.92 (m, 2H, ArH) 8.04-8.07 (m, 2H, ArH). MS(EI): 282.

Example 27

2-(2-Acetoxy-4-isopropylphenyl)-5-methoxy-1,3-dioxo-2,3-dihydro-1H-inden-2-yl acetate 4b, 9b-dihydroxy-7-isopropyl-2-methoxy-4bH-benzo[d]indeno[1,2-b]furan-10(9bH)-one (0.30 g, 0.91 mmol) was completely dissolved in anhydrous THF (10 ml). This solution was added with anhydrous acetic acid (0.18 g, 1.82 mmol), pyridine (0.07 g, 0.91 mmol) and DMAP (0.03 g), and stirred at room temperature. The reaction mixture was concentrated, and extracted with ethylacetate, and the concentrated organic layer was purified using column chromatography (ethylacetate:hexane=1:3) to afford the title compound (0.19 g, 51%).
mp: 146-148° C.
$^1$H-NMR (300 MHz, CDCl$_3$) δ 1.19 (dd, J=2.1, 6.9 Hz, 6H, CH$_3$) 2.13 (s, 3H, OAc) 2.18 (s, 3H, OAc) 2.81-2.90 (m, 1H, CH) 3.93 (s, 3H, OCH$_3$) 6.84 (s, 1H, ArH) 7.13 (d, J=1.2 Hz, 8.4 Hz, 1H, ArH) 7.33-7.36 (m, 2H, ArH) 7.57 (d, J=8.4 Hz, 1H, ArH) 7.91 (d, J=6.0 Hz, 1H, ArH). MS(EI): 410.

Example 28

2-(2-Hydroxy-4-isopropylphenyl)-2-methoxy-1H-inden-1,3(2H)-dione 2-(2-(tert-butyldimethylsilyloxy)-4-isopropylphenyl)-2-methoxy-1H-indene-1,3(2H)-dione (0.2 g, 0.47 mmol) was completely dissolved in anhydrous THF (10 ml). This solution was added with quaternary ammonium fluoride (0.27 g, 1.04 mmol), and stirred at room temperature for 1 hr. The reaction mixture was concentrated, and extracted with ethylacetate, and the concentrated organic layer was purified using column chromatography (ethylacetate:hexane=1:4) to afford the title compound (38 mg, 27%).
mp: 272-274° C.
$^1$H-NMR (300 MHz, CDCl$_3$) δ 1.20 (d, J=7.2 Hz, 6H, CH$_3$) 2.82-2.91 (m, 1H, CH) 3.36 (s, 3H, OCH$_3$) 3.47 (s, 1H, OH) 6.59 (s, 1H, ArH) 6.94 (d, J=8.1 Hz, 1H, ArH) 7.62 (d, J=8.1 Hz, 1H, ArH) 7.87-8.05 (m, 4H, ArH). MS(EI)=310.

Example 29

2-(1,3-Dioxo-2-(pivaloyloxy)-2,3-dihydro-1H-inden-2-yl)-5-isopropylphenyl pivalate To a solution of 4b,9b-dihydroxy-7-isopropyl-4b,9H-dihydro-5-oxa-indeno[2,1-a]inden-10-one (1.00 g, 3.3 mmol) in anhydrous THF were added 2,2-dimethyl-propionyl chloride (0.81 g, 6.7 mmol), trimethylamine (0.40 g, 4.0 mmol), and DMAP (0.1 g), followed by heating for 24 hrs under reflux. The reaction mixture was concentrated in a vacuum, and extracted with ethylaceteta. The extracted organic layer was purified using column chromatography (ethylacetate:hexane=1:6) to afford the title compound (0.38 g, 24%).
mp: 121-124° C.
$^1$H-NMR (300 MHz, CDCl$_3$) δ 1.18 (d, J=8.7 Hz, 6H, CH$_3$) 1.26 (s, 9H, CH$_3$) 1.35 (s, 9H, CH$_3$) 6.67 (s, 1H, ArH) 7.07 (d, J=8.4 Hz, 1H, ArH) 7.42 (d, J=8.4 Hz, 1H, ArH) 7.79-7.83 (m, 2H, ArH) 7.93-7.97 (m, 2H, ArH). MS(EI): 464.

Example 30

2-(2-Hydroxy-1,3-dioxo-2,3-dihydro-1H-inden-2-yl)-5-isopropylphenyl cinnamate

To a solution of 4b,9b-dihydroxy-7-isopropyl-4b,9H-dihydro-5-oxa-indeno[2,1-a]inden-10-one (1.00 g, 3.3 mmol) in anhydrous THF (10 ml) were added 3-phenyl-acyloyl chloride (1.12 g, 6.7 mmol), trimethylamine (0.40 g, 4.0 mmol), and DMAP (0.1 g), followed by heating for 24 hrs under reflux. The reaction mixture was concentrated in a vacuum, and extracted with ethylacetate. The extracted organic layer was purified using column chromatography (ethylacetate:hexane=1:8 to 1:4) to afford the title compound (0.05 g, 3.5%).
mp: 95-97° C.
$^1$H-NMR (300 MHz, CDCl$_3$) δ 1.20 (dd, J=2.7 Hz, 6.8 Hz, 6H, CH$_3$) 2.86-2.91 (m, 1H, CH) 4.20 (m, 1H, OH) 6.24 (d, J=16.0 Hz, 1H, CH) 6.49 (d, J=16.0 Hz, 1H, CH) 6.93 (s, 1H, ArH) 7.20 (d, J=8.3 Hz, 1H, ArH) 7.35-7.59 (m, 6H, ArH) 7.67-7.76 (m, 3H, ArH) 7.67-7.98 (m, 1H, ArH). MS(EI)=426.

Example 31

Dimethyl-carbamic acid 2-(2-dimethylcarbamoyloxy-1,3-dioxo-indan-2-yl)-5-isopropyl-phenyl ester To a solution of 4b,9b-dihydroxy-7-isopropyl-4b,9H-dihydro-5-oxa-indeno[2,1-a]inden-10-one (1.00 g, 3.3 mmol) in anhydrous THF (10 ml) were added dimethylcarbamoyl chloride (0.72 g, 6.7 mmol), trimethylamine (0.41 g, 4.0 mmol), and DMAP (0.1 g), followed by heating for 24 hrs under reflux. The reaction mixture was concentrated in a vacuum, and extracted with ethylacetate. The extracted organic layer was purified using column chromatography (ethylacetate hexane=1:4 to 1:2) to afford the title compound (0.20 g, 13%).
mp: 203-205° C.
$^1$H-NMR (300 MHz, CDCl$_3$) δ 1.19 (d, J=6.8 Hz, 6H, CH$_3$) 2.73 (s, 3H, NCH$_3$) 2.83 (s, 3H, NCH$_3$) 2.93 (s, 3H, NCH$_3$) 3.08 (s, 3H, NCH$_3$) 6.78 (s, 1H, ArH) 7.12 (d, J=8.0 Hz, 1H, ArH) 7.59 (d, J=8.0 Hz, 1H, ArH) 7.79-7.82 (m, 2H, ArH) 7.95-7.98 (m, 2H, ArH). MS(EI): 438.

Example 32

2-(2-(Acryloyloxy)-1,3-dioxo-2,3-dihydro-1H-inden-2-yl)-5-isopropylphenyl acrylate To a solution of 4b,9b-dihydroxy-7-isopropyl-4b,9H-dihydro-5-oxa-indeno[2,1-a]inden-10-one (1.00 g, 3.37 mmol) in anhydrous THF (10 ml) were added acyloyl chloride (0.61 g, 6.74 mmol), trimethylamine (0.41 g, 4.0 mmol), and DMAP (0.1 g), followed by heating for 24 hrs under reflux. The reaction mixture was concentrated in a vacuum, and extracted with ethylacetate. The extracted organic layer was purified using column chromatography (ethylacetate:hexane=1:2 to 1:1) to afford the title compound (0.26 g, 19%).
$^1$H-NMR (300 MHz, CDCl$_3$) δ 1.18 (d, J=2.1 Hz, 7.2 Hz, 6H, CH$_3$) 2.81-2.87 (m, 1H, CH) 5.94-6.24 (m, 4H, CH$_2$) 6.44-6.47 (m, 2H, CH) 6.87 (s, 1H, ArH) 7.15 (d, J=8.1 Hz, 1H, ArH) 7.58 (d, J=8.1 Hz, 1H, ArH) 7.83-7.86 (m, 2H, ArH) 7.96-7.99 (m, 2H, ArH). MS (EI): 404

Example 33

Diethyl-carbamic acid 2-(2-diethylcarbamoyloxy-1,3-dioxo-indan-2-yl)-5-isopropyl-phenyl ester To a solution of 4b,9b-dihydroxy-7-isopropyl-4b,9H-dihydro-5-oxa-indeno[2,1-a]inden-10-one (1.00 g, 3.3 mmol) in anhydrous THF were added trimethylamine (0.40 g, 4.0 mmol), diethylcarbamoyl chloride (0.91 g, 6.7 mmol), and DMAP (0.1 g), followed by heating for 24 hrs under reflux. The reaction mixture was concentrated in a vacuum, and extracted with ethylacetate. The extracted organic layer was purified using column chromatography (ethylacetate:hexane=1:4 to 1:2) to afford the title compound (0.54 g, 32%).
mp: 103-105° C.
$^1$H-NMR (300 MHz, CDCl$_3$) δ 1.02-1.28 (m, 18H, CH$_3$) 2.82-2.86 (m, 1H, CH) 3.10-3.26 (m, 6H, NCH$_2$) 3.40 (q, J=14.2 Hz, 7.1 Hz, 2H, NCH$_2$) 6.73 (s, 1H, ArH) 7.10 (d, J=8.3 Hz, 1H, ArH) 7.60 (d, J=8.3 Hz, 1H, ArH) 7.76-7.79 (m, 2H, ArH) 7.93-7.96 (m, 2H, ArH). MS(EI): 494.

Example 34

2-(2-Hydroxy-1,3-dioxo-2,3-dihydro-1H-inden-2-yl)-5-isopropylphenyl diethylcarbamate To a solution of 4b,9b-dihydroxy-7-isopropyl-4b,9H-dihydro-5-oxa-indeno[2,1-a]inden-10-one (1.00 g, 3.3 mmol) in anhydrous THF were added trimethylamine (0.40 g, 4.0 mmol), diethylcarbamoyl chloride (0.91 g, 6.7 mmol), and DMAP (0.1 g), followed by heating for 24 hrs under reflux. The reaction mixture was concentrated in a vacuum, and extracted with ethylacetate. The extracted organic layer was purified using column chromatography (ethylacetate:hexane=1:4 to 1:2) to afford the title compound (0.06 g, 5%).
mp: 103-106° C.
$^1$H-NMR (300 MHz, CDCl$_3$) δ 0.94-1.04 (m, 6H, CH$_3$) 1.20 (d, J=6.9 Hz, 6H, CH$_3$) 2.81-2.89 (m, 3H, CH, NCH$_2$) 3.08 (q, J=14.2 Hz, 7.1 Hz, 2H, NCH$_2$) 4.03 (s, 1H, OH) 6.74 (s, 1H, ArH) 7.14 (d, J=8.1 Hz, 1H, ArH) 7.70 (d, J=7.8 Hz, 1H, ArH) 7.84-7.89 (m, 2H, ArH) 7.99-8.03 (m, 2H, ArH). MS(EI): 395

Example 35

2-Hydroxy-2-(4-hydroxy-2,5-dimethylphenyl)-1H-inden-1,3(2H)-dione

To a solution of ninhydrin (1.00 g, 5.6 mmol) in glacial acetic acid (20 ml) was added 2,5-dimethyl phenol (0.68 g, 5.6 mmol), followed by heating for 24 hrs under reflux. The reaction mixture was concentrated in a vacuum, and extracted with ethylacetate. The concentrated organic layer was purified using column chromatography (ethylacetate:hexane=1:6 to 1:4) to afford the title compound (0.13 g, 8%).
mp: 228-230° C.
$^1$H-NMR (300 MHz, CDCl$_3$+CD$_3$OD) δ 2.12 (s, 3H, CH$_3$) 2.24 (s, 3H, CH$_3$) 3.39 (s, 1H, OH) 5.59 (s, 1H, OH) 6.54 (s, 1H, ArH) 7.02 (s, 1H, ArH) 7.90-7.93 (m, 2H, ArH) 8.03-8.06 (m, 2H, ArH). MS(EI)=282.

Example 36

Acetic acid 2-(2-acetoxy-4-isopropyl-phenyl)-4-amino-1,3-dioxo-indan-2-yl ester

Triethylamine (0.10 g, 0.6 mmol) was added to a solution of 1-amino-4b,9b-dihydroxy-7-isopropyl-4b,9b-dihydro-5-oxa-indeno[2,1-a]inden-10-one (0.20 g, 0.6 mmol) in methylene chloride (5 ml) at room temperature. To this reaction mixture, a dilution of 10% acetyl chloride (1 ml) in methylene chloride was slowly added at 0° C. and stirred at room temperature 1 hr. The reaction mixture was concentrated in a vacuum, and extracted with ethylacetate. The concentrated organic layer was purified using column chromatography (ethylacetate:hexane=1:4 to 1:2) to afford the title compound (100 mg, 40%).
mp: 148-151° C.
$^1$H-NMR (300 MHz, CDCl$_3$) δ 1.19 (d, J=6.9 Hz, 6H, CH$_3$) 2.07 (s, 3H, OAc) 2.18 (s, 3H, OAc) 2.83-2.88 (m, 1H, CH) 5.67 (s, 2H, NH$_2$) 6.83 (d, J=1.8 Hz, 1H, ArH) 6.88 (d, J=8.4 Hz, 1H, ArH) 7.14 (dd, J=8.4 Hz, 2.1 Hz, 1H, ArH) 7.22 (d, J=7.2 Hz, 1H, ArH) 7.53 (t, J=7.2 Hz, 1H, ArH) 7.59 (d, J=8.4 Hz, 1H, ArH). 13C-NMR (300 MHz, DMSO) δ 19.86, 20.83, 23.98, 34.89, 82.49, 111.47, 122.19, 122.52, 123.17, 123.91, 125.54, 130.59, 138.55, 141.87, 148.87, 149.94, 153.17, 17.077, 171.10, 195.88, 196.68. MS(EI): 395.

Example 37

Acetic acid 2-(2-acetoxy-4-isopropyl-phenyl)-4-nitro-1,3-dioxo-indan-2-yl ester

Triethylamine (0.11 g, 1.16 mmol) was added to a solution of 4b,9b-dihydroxy-7-isopropyl-1-nitro-4b,9b-dihydro-5-oxa-indeno[2,1-a]inden-10-one (0.20 g, 0.58 mmol) in anhydrous chloroform (10 ml) at room temperature. To this reaction mixture, acetyl chloride (1 ml) was slowly added at ° C. and stirred at room temperature 1 hr. The reaction mixture was concentrated in a vacuum, and extracted with ethylacetate. The concentrated organic layer was purified using column chromatography (ethylacetate:hexane=1:4 to 1:2) to afford the title compound (30 mg, 12%).

mp: 94-98° C.

¹H-NMR (300 MHz, CDCl₃) δ 1.20 (dd, J=6.9 Hz, 6H, CH₃) 2.19 (s, 3H, OAc) 2.27 (s, 3H, OAc) 2.83-2.92 (m, 1H, CH) 6.91 (s, 1H, ArH) 7.15 (dd, J=8.2 Hz, 1.7 Hz, 1H, ArH) 7.53 (d, J=8.2 Hz, 1H, ArH) 7.99 (t, J=7.8 Hz, 1H, ArH) 8.23 (dd, J=3.0 Hz, 7.8 Hz, 2H, ArH). ¹³C-NMR (300 MHz, CDCl₃) δ 19.72, 20.92, 23.45, 33.71, 82.07, 119.57, 12.83, 125.03, 127.88, 129.86, 130.24, 131.48, 136.49, 141.09, 145.18, 148.77, 153.02, 168.90, 169.92, 187.91, 190.47. MS(EI): 425.

Example 38

2-Hydroxy-2-(4-isopropyl-2-methoxyphenyl)-4-nitro-2H-inden-1,3-dione

A solution of 4-nitro-2,3-dihydro-1H-inden-1-one (4.00 g, 20.9 mmol) in 1,4-dioxane (40 ml) and glacial acetic acid (4 ml) was added with selenium dioxide (5.10 g, 46.03 mmol), and refluxed for 3 hrs. After filtration at high temperature, the filtrate was concentrated to afford 2,2-dihydroxy-4-nitro-2H-inden-1,3-dione (4.67 g, 100%). To a solution of 2,2-dihydoxy-4-nitro-2H-inden-1,3-dione (4.67 g, 20.9 mmol) in TFA (10 ml) was added isopropyl anisole (3.14 g, 20.9 mmol), followed by stirring at 60° C. for 6 hrs. The reaction mixture was concentrated in a vacuum, and extracted with aq. sodium bicarbonate and ethylacetate. The concentrated organic layer was purified using column chromatography (ethylacetate:hexane=1:4) to afford the title compound (1.19 mg, 16%).

¹H-NMR (300 MHz, CDCl₃) δ 1.21 (d, J=6.9 Hz, 6H, CH₃) 2.82-2.92 (m, H, CH) 3.05 (s, 3H, OCH₃) 3.75 (s, 3H, OH) 6.60 (s, 1H, ArH) 6.96 (dd, J=7.8 Hz, 1H, ArH) 7.65 (d, J=8.1 Hz, 1H, ArH) 8.01 (t, J=7.8 Hz, 1H, ArH) 8.20-8.26 (m, 2H, ArH). MS(EI): 355.3.

Example 39

2-Chloro-2-(4-isopropyl-2-methoxyphenyl)-4-nitro-2H-inden-1,3-dione 2-hydroxy-2-(4-isopropyl-2-methoxyphenyl)-4-nitro-2H-inden-1,3-dione (1.00 g, 2.8 mmol) was dissolved in excess of thionyl chloride (10 ml), stirred at room temperature for 2 hrs. The reaction mixture was concentrated in a vacuum, and extracted with aq. sodium bicarbonate and ethylacetate. The organic layer was concentrated to afford the title compound (1.05 g, 77%).

mp: 81-84° C.

¹H-NMR (300 MHz, CDCl₃) δ 1.25 (d, J=6.9 Hz, 6H, CH₃) 2.87-2.96 (m, 1H, CH) 3.44 (s, 3H, OCH₃) 6.65 (s, 1H, ArH) 7.02 (dd, J=1.2 Hz, 7.8 Hz, 1H, ArH) 8.05-8.12 (m, 1H, ArH) 8.22 (dd, J=1.2 Hz, 7.8 Hz, 1H, ArH) 8.28-8.35 (m, 2H, ArH). MS(EI): 373.

Example 40

2-Azido-2-(4-isopropyl-2-methoxyphenyl)-4-nitro-2H-inden-1,3-dione 2-chloro-2-(4-isopropyl-2-methoxyphenyl)-4-nitro-2H-inden-1,3-dione (1.23 g, 3.2 mmol) was completely dissolved in acetone (30 ml). This solution was added with sodium azide (0.47 g, 7.2 mmol), sodium iodide (0.59 g, 3.9 mmol), water (6 ml), followed by heating 12 hrs under reflux. The reaction mixture was concentrated, and extracted with ethylacetate, and the concentrated organic layer was purified using column chromatography (ethylacetate:hexane=1:4) to afford the title compound (Brown syrup, 600 mg, 48%).

¹H-NMR (300 MHz, CDCl₃) δ 1.23 (d, J=6.9 Hz, 6H, CH₃) 2.28-2.94 (m, 1H, CH) 3.40 (s, 3H, OCH₃) 6.63 (d, J=1.5 Hz, 1H, ArH) 7.01 (dd, J=1.5 Hz, 8.1 Hz, 1H, ArH) 7.56-7.60 (m, 2H, ArH) 7.78-7.90 (m, 2H, ArH). MS(EI): 380.

Example 41

4-Amino-2-hydroxy-2-(4-isopropyl-2-methoxyphenyl)-2H-inden-1,3-dione 2-hydroxy-2-(4-isopropyl-2-methoxyphenyl)-4-nitro-2H-inden-1,3-dione (52 mg, 1.4 mmol) was completely dissolved in anhydrous ethanol (10 ml). This solution was added with iron (0.59 g, 10.6 mmol), conc. HCl (0.01 ml) and water (1 ml). The reaction mixture was heated for 3 hrs under reflux. After filtration at high temperature to remove iron, the filtrate was concentrated in a vacuum and purified using column chromatography (ethylacetate:hexane=1:2) to afford the title compound (0.32 g, 68%).

mp: 219-220° C.

¹H-NMR (300 MHz, CDCl₃) δ 1.21 (d, J=6.9 Hz, 6H, CH₃) 2.82-2.91 (m, 1H, CH) 3.41-3.45 (s, 3H, OCH₃) 6.60 (d, J=1.2 Hz, 1H, ArH) 6.89-6.98 (m, 2H, ArH) 7.21-7.27 (m, 1H, ArH) 7.56-7.66 (m, 2H, ArH). MS(EI): 325.

Example 42

N-(2-Hydroxy-2-(4-isopropyl-2-methoxyphenyl)-7-nitro-1,3-dioxo-2,3-dihydro-1H-inden-4-yl)acetamide N-(2,2-dihydroxy-7-nitro-1,3-dioxo-2,3-dihydro-1H-inden-4-yl)acetamide (1.50 g, 6.4 mmol) was completely dissolved in anhydrous dioxane (15 ml). This solution was added with selenium oxide (1.56 g, 14.0 mmol) and AcOH (1.5 ml). The reaction mixture was heated for 12 hrs under reflux. After filtration at high temperature, the filtrate was concentrated to afford 1.79 g (100%). A trifluoroacetic acid solution of the resulting product was added with isopropyl-3-methoxy benzene (962 mg, 6.4 mmol) followed by stirring for 12 hours. The resulting product was extracted with ethyl acetate, and concentrated organic layer was purified using column chromatography (ethylacetate:hexane=1:1) to afford the title compound (0.52 g, 20%).

mp: 110-115° C.

¹H-NMR (300 MHz, CDCl₃) δ 1.23 (d, J=6.9 Hz, 6H, CH₃) 2.29 (s, 3H, CH₃), 2.84-2.93 (m, 1H, CH) 3.57 (s, 3H, OCH₃), 3.78 (s, 1H, OH), 6.63 (s, 1H, ArH) 7.00 (dd, J=1.5, 8.1 Hz, 1H, ArH) 7.68 (d, J=8.1 Hz, 1H, ArH) 8.28 (d, J=8.7 Hz, 1H, ArH) 9.04 (d, J=2.4, 9.0 Hz, 1H, ArH) 10.54 (s, 1H, NH). MS(EI): 412.39.

Example 43

N-(2-Hydroxy-2-(4-isopropyl-2-methoxyphenyl)-5-nitro-1,3-dioxo-2,3-dihydro-1H-inden-4-yl)acetamide N-(2,2-dihydroxy-5-nitro-1,3-dioxo-2,3-dihydro-1H-inden-4-yl)acetamide (2.60 g, 11.1 mmol) was completely dissolved in anhydrous dioxane (20 ml). This solution was added with selenium oxide (2.70 g, 24.4 mmol) and AcOH (1.5 ml). The reaction mixture was heated for 7 hrs under reflux. After filtration at high temperature, the filtrate was concentrated to afford 1.79 g (100%). Trifluoroacetic solution of the resulting product was added with isopropyl-3-methoxybenzene (1.66 g, 11.1 mmol), followed by stirring for 12 hrs. The remainder was extracted with ethyl acetate, and concentrated organic layer was purified using column chromatography (ethylacetate 100%) to afford the title compound (0.64 g, 14%).

mp: 199-201° C.

$^1$H-NMR (300 MHz, CDCl$_3$) δ 1.23 (d, J=6.9 Hz, 6H, CH$_3$) 2.28 (s, 3H, CH$_3$), 2.84-2.91 (m, 1H, CH) 3.42 (s, 3H, OCH$_3$), 3.77 (s, 1H, OH), 6.65 (s, 1H, ArH) 7.00 (dd, J=1.4, 7.9 Hz, 1H, ArH) 7.63 (d, J=7.9 Hz, 1H, ArH) 7.85 (d, J=8.1 Hz, 1H, ArH) 8.35 (d, J=8.1 Hz, 1H, ArH) 9.79 (s, 1H, NH). MS(EI): 412.

Example 44

N-(7-Amino-2-hydroxy-2-(4-isopropyl-2-methoxyphenyl)-1,3-dioxo-2,3-dihydro-1H-inden-4-yl)acetamide N-(2-hydroxy-2-(4-isopropyl-2-methoxyphenyl)-7-nitro-1,3-dioxo-2,3-dihydro-1H-inden-4-yl)acetamide (0.10 g, 0.24 mmol) was completely dissolved in anhydrous ethanol (3 ml). This solution was added with iron (0.098 g), conc. HCl (0.05 ml) and water (0.3 ml). The reaction mixture was heated for 2 hrs under reflux. After filtration at high temperature to remove iron, the filtrate was concentrated in a vacuum and purified using column chromatography (ethylacetate:hexane=1:2) to afford the title compound (65 mg, 71%).

$^1$H-NMR (300 MHz, CDCl$_3$) δ 1.22 (s, 6H, CH$_3$) 2.20 (s, 3H, CH$_3$) 2.83-2.92 (m, 1H, CH) 3.50 (s, 3H, OCH$_3$) 3.78 (s, 1H, OH) 5.54 (s, 2H, NH$_2$) 6.66 (d, J=2.7 Hz, 1H, ArH) 6.91-7.07 (m, 2H, ArH) 7.56 (d, J=7.8 Hz, 1H, ArH) 8.76 (d, J=3.3, 9.0 Hz, 1H, ArH) 9.81 (s, 1H, NH). MS(EI): 382.

Example 45

N-(5-Amino-2-hydroxy-2-(4-isopropyl-2-methoxyphenyl)-1,3-dioxo-2,3-dihydro-1H-inden-4-yl)acetamide N-(2-hydroxy-2-(4-isopropyl-2-methoxyphenyl)-5-nitro-1,3-dioxo-2,3-dihydro-1H-inden-4-yl)acetamide (0.10 g, 0.24 mmol) was completely dissolved in anhydrous ethanol (3 ml). This solution was added with iron (0.098 g), conc. HCl (0.05 ml) and water (0.3 ml). The reaction mixture was heated for 2 hrs under reflux. After filtration at high temperature to remove iron, the filtrate was concentrated in a vacuum and purified using column chromatography (ethylacetate 100%) to afford the title compound (90 mg, 98%).

mp: 124-131° C.

$^1$H-NMR (300 MHz, CDCl$_3$) δ 1.21 (d, J=6.9 Hz, 6H, CH$_3$) 2.30 (s, 3H, CH$_3$) 2.83-2.92 (m, CH) 3.46 (s, 3H, OCH$_3$) 3.78 (s, 1H, OH) 5.36 (s, 2H, NH$_2$) 6.62 (s, 1H, ArH) 6.93 (d, J=8.1 Hz, 1H, ArH) 7.14 (d, J=8.4 Hz, 1H, ArH) 7.56 (d, J=8.1 Hz, 1H, ArH) 7.70 (d, J=8.1 Hz, 1H, ArH) 9.56 (s, 1H, NH). MS(EI): 382.

Example 46

4,7-Diamino-2-hydroxy-2-(4-isopropyl-2-methoxyphenyl)-2H-inden-1,3-dione

N-(7-amino-2-hydroxy-2-(4-isopropyl-2-methoxyphenyl)-1,3-dioxo-2,3-dihydro-1H-inden-4-yl)acetamide (45 mg, 0.10 mmol) was completely dissolved in 6M HCl (1.4 ml) and methanol (0.1 ml), followed by heating for 90 min at 80. The reaction mixture was diluted with methylene chloride, extracted with 2N NaOH aqueous solution, and the concentrated organic layer was purified using column chromatography (ethylacetate:hexane=1:1) to afford the title compound (80 mg, 200%).

mp: 243-247° C.

$^1$H-NMR (300 MHz, CDCl$_3$) δ 1.21 (d, J=6.9 Hz, 6H, CH$_3$) 2.84-2.88 (m, 1H, CH) 3.55 (s, 3H, OCH$_3$) 3.78 (s, 1H, OH) 5.20 (s, 2H, NH$_2$) 6.64 (s, 1H, ArH) 6.90 (s, 3H, ArH) 7.52 (d, J=7.8 Hz, 1H, ArH). MS(EI): 340.

Example 47

4,5-Diamino-2-hydroxy-2-(4-isopropyl-2-methoxyphenyl)-2H-inden-1,3-dione

N-(5-amino-2-hydroxy-2-(4-isopropyl-2-methoxyphenyl)-1,3-dioxo-2,3-dihydro-1H-inden-4-yl)acetamide (85 mg, 0.19 mmol) was completely dissolved in 6M HCl (1.4 ml) and methanol (0.1 ml), followed by heating for 40 min at 80. The reaction mixture was diluted with methylene chloride, extracted with 2N NaOH aqueous solution, and the concentrated organic layer was purified using column chromatography (ethylacetate:hexane=1:1) to afford the title compound (30 mg, 44%).

mp: 272-274° C.

$^1$H-NMR (300 MHz, CDCl$_3$) δ 1.21 (d, J=6.9 Hz, 6H, CH$_3$) 2.83-2.92 (m, 1H, CH) 3.33 (s, 3H, OCH$_3$) 3.76 (s, 1H, OH) 4.13 (s, 2H, NH$_2$) 6.63 (s, 1H, ArH) 6.96 (d, J=7.8 Hz, 1H, ArH) 7.68 (d, J=7.8 Hz, 1H, ArH) 7.83 (d, J=8.1 Hz, 1H, ArH) 8.08 (d, J=8.4 Hz, 1H, ArH). MS(EI): 340.

Example 48

Methyl 2-(4-isopropyl-2(methoxycarbonyloxy)phenyl)-1,3-dioxo-2,3-dihydro-1H-inden-2-yl carbamate 9b-amino-4b-hydroxy-7-isopropyl-4b,9b-dihydro-5-oxaindeno[2,1-a]inden-10-one (0.30 g, 1.01 mmol) was completely dissolved in THF (10 ml). This solution was added with triethylamine (0.17 ml, 1.21 mmol) and methylchloroformate (0.07 ml, 1.01 mmol), followed by heating for 3 hrs under room temperature. After the reaction mixture was concentrated in a vaccum, extracted with water and methylene chloride, and purified using column chromatography (ethylacetate:hexane=1:2) to afford the title compound (0.30 g, 72%).

mp: 105-107° C.

$^1$H-NMR (300 MHz, CDCl$_3$) δ 1.18 (d, J=6.9 Hz, 6H), 2.85 (q, J=7.1 Hz, 1H), 3.61 (s, 3H), 3.89 (s, 3H), 5.97 (s, 1H), 6.91 (s, 1H), 7.14 (d, J=8.4 Hz, 1H), 7.51 (d, J=8.4 Hz, 1H), 7.82-7.87 (m, 2H), 7.97-8.03 (m, 2H).

Example 49

2-(1,3-Dioxo-2-pentanamido-2,3-dihydro-1H-inden-2-yl)-5-isopropylphenyl pentanoate 9b-amino-4b-hydroxy-7-isopropyl-4b,9b-dihydro-5-oxaindeno[2,1-a]inden-10-one (0.30 g, 1.01 mmol) was dissolved in THF (10 ml). This solution was added with valeryl chloride (0.12 ml, 1.01 mmol), followed by heating for 1 hr under room temperature. After the reaction mixture was concentrated in a vaccum, extracted with water and methylene chloride, and purified using column chromatography (ethylacetate:hexane=1:4) to afford the title compound (0.10 g, 20%).

mp: 117-118° C.

¹H-NMR (300 MHz, CDCl₃) δ 0.89 (t, J=7.8 Hz, 3H), 1.00 (t, J=8.1 Hz, 3H), 1.17 (d, J=6.8 Hz, 6H), 1.29-1.40 (m, 2H), 1.42-1.62 (m, 4H), 1.77 (q, J=8.8 Hz, 2H), 2.24 (t, J=8.3 Hz, 2H), 2.65 (t, J=9.4 Hz, 2H), 2.84 (q, J=7.8 Hz, 1H), 6.67 (s, 1H), 6.85 (s, 1H), 7.05 (dd, J=1.4 Hz, 8.3 Hz, 1H), 7.34 (d, J=8.1 Hz, 1H), 7.79-7.84 (m, 2H), 7.93-7.99 (m, 2H).

Example 50

2-(2-Isobutylamido-1,3-dioxo-2,3-dihydro-1H-inden-2-yl)-5-isopropylphenyl isobutyrate 9b-Amino-4b-hydro-7-isopropyl-4b,9b-dihydro-5-oxaindeno[2,1-a]-inden-10-one (0.30 g, 1.01 mmol) was dissolved in THF (10 ml). This solution was added with triethylamine (0.17 ml, 1.21 mmol), isobutyryl chloride (0.10 ml, 1.01 mmol), and stirred at room temperature for 1 hrs. The reaction mixture was concentrated in a vacuum, and extracted with water and methylene chloride. The extracted organic layer was purified using column chromatography (ethylacetate:hexane=1:2) to afford the title compound (0.10 g, 23%).
mp: 195-197° C.
¹H-NMR (300 MHz, CDCl₃) δ 1.15 (d, J=6.9 Hz, 6H), 1.17 (d, J=6.9 Hz, 6H), 1.38 (d, J=7.0 Hz, 6H), 2.45 (q, J=7.3 Hz, 1H), 2.77-3.00 (m, 2H), 6.70 (s, 1H), 6.82 (d, J=1.7 Hz, 1H), 7.04 (dd, J=1.7 Hz, 8.2 Hz, 1H), 7.29 (d, J=8.2 Hz, 1H), 7.77-7.84 (m, 2H), 7.93-7.99 (m, 2H).

Example 51

2-Hydroxy-2-(2-hydroxy-4-isopropylphenyl)-2,3-dihydro-1H-inden-1-one

To a solution of 4b,9b-dihydroxy-7-isopropyl-4bH-benzo[d]indeno[1,2-b]furan-10(9bH)-one (1.0 g, 3.3 mmol) in diethylene glycol (10 ml) were added with hydrazine hydrate (80%, 0.36 g, 9.6 mmol), followed by stirring at 150° C. for 15 min. The reaction mixture was added potassium hydroxide (360 mg, 6.4 mmol), and stirred at 165-170° C. for 1 hrs. The reaction mixture was extracted with ethylacetate, and purified using column chromatography (20% ethylacetate in hexane) to afford the title compound (60 g, 6.5%).
mp: 144-146° C.
¹H-NMR (300 MHz, CDCl₃) δ 1.17 (d, J=7 Hz, 6H, CH₃) 2.75-2.79 (septet, 1H, CH) 3.52-3.69 (m, 2H, CH₂) 6.57 (d, J=8.0 Hz, 1H, ArH) 6.70 (d, J=8.0 Hz, 1H, ArH) 6.79 (s, 1H, ArH) 7.41 (t, J=6.8 Hz, 2H, ArH) 7.65 (t, J=7.1 Hz, 1H, ArH) 7.82 (d, J=7.7 Hz, 1H, ArH). MS(EI): 282.

Example 52

2-Azido-2-(4-isopropyl-2-methoxyphenyl)-2H-inden-1,3-dione

To a solution of 2-chloro-2-(4-isopropyl-2-methoxyphenyl)-1H-inden-1,3(2H)-dione (0.10 g, 0.3 mmol) in acetone (5 ml) were added with sodium iodide (54 mg, 0.36 mmol) and sodium azide (50 mg, 0.76 mmol) and distilled water (1 ml), followed by stirring at 80° C. for 6 hrs. The reaction mixture was added water, and extracted diethyl ether, and washed with water and brine in that order. The washed organic layer was concentrated to afford the title compound (100 g, 98%).
mp: 175-177° C.
¹H-NMR (300 MHz, CDCl₃) δ 1.24 (d, J=6.9 Hz, 6H, CH₃) 2.89 (septet, J=6.9 Hz, 1H, CH) 3.43 (s, 3H, OCH₃) 6.62 (d, J=1.2 Hz, 1H, ArH) 7.02 (dd, J=7.8 Hz, J=1.2 Hz, 1H, ArH) 7.61 (d, J=8.1 Hz, 1H, ArH) 7.89-7.95 (m, 2H, ArH) 8.03-8.09 (m, 2H, ArH). MS(EI): 335.

Example 53

2-Amino-2-(4-isopropyl-2-methoxyphenyl)-2H-inden-1,3-dione

To a solution of 2-azido-2-(4-isopropyl-2-methoxyphenyl)-2H-inden-1,3-dione (50 mg, 0.15 mmol) in methanol (10 ml) were added with triphenylphosphine (47 mg, 0.18 mmol), followed by stirring at 60° C. for 4 hrs. The concentrated reaction mixture was purified using silica column chromatography (25% ethylacetate in hexane) to afford the title compound (25 g, 54%).
mp: 164-166° C.
¹H-NMR (300 MHz, CDCl₃) δ 1.22 (d, J=6.9 Hz, 6H, CH₃) 2.88 (septet, J=6.9 Hz, 1H, CH) 3.30 (s, 3H, OCH₃) 6.57 (d, J=1.2 Hz, 1H, ArH) 6.97 (dd, J=7.8 Hz, J=1.5 Hz, 1H, ArH) 7.60 (d, J=7.8 Hz, 1H, ArH) 7.86-7.90 (m, 2H, ArH) 8.00-8.04 (m, 2H, ArH). MS(EI): 309.

Example 54

N-(2-(4-Isopropyl-2-methoxyphenyl)-1,3-dioxo-2,3-dihydro-1H-inden-2-yl)acetamide 2-Amino-2-(4-isopropyl-2-methoxyphenyl)-2H-inden-1,3-dione (0.10 g, 0.32 mmol) was dissolved in methylene chloride (4 ml). This solution was added with acetyl chloride (0.05 ml, 0.70 mmol), followed by stirring at room temperature for 15 min, and added with triethylamine (0.12 ml, 0.86 mmol), and stirred for 6 hrs. After the reaction mixture was extracted with methylene chloride (50 ml×3), the organic layer was purified using column chromatography (45% ethylacetate in hexane) to afford the title compound (70 g, 62%).
mp: 222-224° C.
¹H-NMR (300 MHz, CDCl₃) δ 1.18 (d, J=6.9 Hz, 6H, CH₃) 1.95 (s, 3H, OAc) 2.82 (septet, J=6.9 Hz, 1H, CH) 3.51 (s, 3H, OCH3) 6.63 (d, J=1.5 Hz, 1H, ArH) 6.85-6.90 (m, 2H, NH, ArH) 7.41 (d, J=8.4 Hz, 1H, ArH) 7.76-7.82 (m, 2H, ArH) 7.93-7.97 (m, 2H, ArH). MS(EI): 351.

Example 55

N-(2-(4-Isopropyl-2-methoxyphenyl)-1,3-dioxo-2,3-dihydro-1H-inden-2-yl)benzamide A solution of 2-amino-2-(4-isopropyl-2-methoxyphenyl)-2H-inden-1,3-dione (200 mg, 0.60 mmol) in dichloromethane (10 ml) was stirred overnight together with benzoyl chloride (0.09 mL, 0.77 mmol) and triethylamine (0.27 mL, 1.9 mmol) at room temperature. The reaction mixture was extracted with dichloromethane, and purified by silica gel column chromatography (30% ethylacetate in hexane) to afford the title compound (250 mg, 97%).
mp: 106-108° C.
¹H-NMR (300 MHz, CDCl₃) δ 1.21 (d, J=6.9 Hz, 6H, CH₃) 2.86 (septet, J=6.9 Hz, 1H, CH) 3.64 (s, 3H, OCH₃) 6.72 (s, 1H, ArH) 6.90 (d, J=8.1 Hz, 1H, ArH) 7.40-7.45 (m, 3H, ArH) 7.50-7.55 (m, 2H, ArH) 7.80-7.87 (m, 4H, ArH) 8.01-8.06 (m, 2H, ArH). MS(EI): 413.

Example 56

N-(2-(4-Isopropyl-2-methoxyphenyl)-1,3-dioxo-2,3-dihydro-1H-inden-2-yl)cyclopropancarboxamide A solution of 2-amino-2-(4-isopropyl-2-methoxyphenyl)-2H-inden-1,3-dione (200 mg, 0.60 mmol) in dichloromethane (10 ml) was stirred overnight together with cyclopropyl carbonyl chloride (0.07 mL, 0.77 mmol) and triethylamine (0.27 mL, 1.9 mmol) at room temperature. The reaction mixture was extracted with dichloromethane, and purified by silica gel column chromatography (30% ethylacetate in hexane) to afford the title compound (235 mg, 96%).

mp: 145-147° C.

$^1$H-NMR (300 MHz, CDCl$_3$) δ 1.22 (d, J=6.9 Hz, 6H, CH$_3$) 2.88 (septet, J=6.9 Hz, 1H, CH) 3.30 (s, 3H, OCH$_3$) 6.57 (d, J=1.2 Hz, 1H, ArH) 6.97 (dd, J=7.8 Hz, J=1.5 Hz, 1H, ArH) 7.60 (d, J=7.8 Hz, 1H, ArH) 7.86-7.90 (m, 2H, ArH) 8.00-8.04 (m, 2H, ArH). MS(EI): 377.

Example 57

2-(2-(Methylthio)phenyl)-2H-inden-1,3-dione

Ninhydrin (0.10 g, 0.56 mmols) and thioanisole (0.07 mL, 0.56 mmols) were dissolved in trifluoroacetic acid (3 mL) and was stirred for 90 min at room temperature. The reaction mixture was neutralization with an aqueous sodium bicarbonate solution and was extracted with ethylacetate and was purified by silica gel column chromatography to afford the title compound (20 mg, 13%).

mp: 191-193° C.

$^1$H-NMR (300 MHz, CDCl$_3$) δ 2.11 (s, 3H, SMe) 3.70 (b, 1H, OH) 7.34-7.42 (m, 3H, ArH) 7.82 (m, 1H, ArH) 7.87-7.96 (m, 2H, ArH) 8.01-8.05 (m, 2H, ArH). MS(EI): 284.

Example 58

2-(4-(Methylthio)phenyl)-2H-inden-1,3-dione

The title compound (115 mg, 77%) was obtained in a similar manner as described in EXAMPLE 70.

mp: 153-155° C.

$^1$H-NMR (300 MHz, CDCl$_3$) δ 2.14 (s, 3H, SMe) 3.74 (b, 1H, OH) 7.13-7.17 (m, 2H, ArH) 7.26-7.31 (m, 2H, ArH) 7.90-7.95 (m, 2H, ArH) 8.03-8.06 (m, 2H, ArH). MS(EI): 284.

Example 59

Methyl 2-(4-isopropyl-2-methoxyphenyl)-1,3-dioxo-2,3-dihydro-1H-inden-2-ylcarbamate A solution of 2-amino-2-(4-isopropyl-2-methoxyphenyl)-2H-inden-1,3-dione (0.50 g, 1.62 mmol) in anhydrous THF (10 ml) was added triphosgene (0.21 g, 0.71 mmol) and stirred for 30 min. The reaction mixture was concentrated and was dissolved in methanol (6 mL) and was stirred for 2 hrs and was concentrated to afford the title compound (220 mg, 93%).

mp: 153-155° C.

$^1$H-NMR (300 MHz, CDCl$_3$) δ 1.18 (d, J=6.9 Hz, 6H, CH$_3$) 2.83 (septet, J=6.9 Hz, 1H, CH) 3.50 (s, 3H, OCH$_3$) 3.65 (s, 3H, OCH$_3$) 5.94 (br, 1H, NH) 6.63 (d, J=1.5 Hz, 1H, ArH) 6.89 (dd, J=8.1 Hz, J=1.5 Hz, 1H, ArH) 7.44 (d, J=8.1 Hz, 1H, ArH) 7.79-7.85 (m, 2H, ArH) 7.97-8.03 (m, 2H, ArH). MS(EI): 367.

Example 60

1-Ethyl-3-(2,3-dihydro-2-(4-isopropyl-2-methoxyphenyl)-1,3-dioxo-1H-inden-2-yl)urea A solution of 2-amino-2-(4-isopropyl-2-methoxyphenyl)-2H-inden-1,3-dione (0.50 g, 1.62 mmol) in anhydrous THF (10 ml) was added triphosgene (0.52 g, 1.77 mmol) and stirred for 15 min. The reaction mixture was concentrated and was dissolved in anhydrous THF (10 ml) and was added ethylamine (2.0M in methanol, 2 mL, 400 mmol) and was stirred for 2 hrs. Concentrated reaction mixture was added dichloromethane to afford the title compound (450 mg, 74%).

mp: 267-269° C.

$^1$H-NMR (300 MHz, CDCl$_3$) δ 1.17·1.23 (m, 9H, CH$_3$) 2.72 (br, 1H, NH) 2.89 (septet, J=6.9 Hz, 1H, CH) 3.30-3.44 (m, 4H, CH$_3$ and CH$_2$) 3.50-3.62 (m, 1H, CH2) 5.33 (s, 1H, NH) 6.70 (s, 1H, ArH) 6.96 (dd, J=8.1 Hz, J=1.2 Hz, 1H, ArH) 7.51 (d, J=8.1 Hz, 1H, ArH) 7.59-7.64 (m, 1H, ArH) 7.75-7.83 (m, 2H, ArH) 7.94 (d, J=7.8 Hz, 1H, ArH). MS(EI): 380.

Example 61

1-(2,3-Dihydro-2-(4-isopropyl-2-methoxyphenyl)-1,3-dioxo-1H-inden-2-yl)urea

A solution of 2-amino-2-(4-isopropyl-2-methoxyphenyl)-2H-inden-1,3-dione (0.50 g, 1.62 mmol) in anhydrous THF (10 ml) was added triphosgene (0.52 g, 1.77 mmol) and stirred for 15 min. The reaction mixture was concentrated and was dissolved in anhydrous THF (10 ml) and was added ammonia ((2.0M in IPA, 1.6 mL, 3.23 mmol) was stirred for 2 hrs. The reaction mixture was oncentrated and was purified using silica gel column chromatography to afford the title compound (150 mg, 29%).

mp: 272-274° C.

$^1$H-NMR (300 MHz, Acetone-D$_6$) δ 1.24 (d, J=6.9 Hz, 6H, CH$_3$) 2.84-2.96 (m, 3H, CH, NH$_2$) 3.30 (s, 3H, OMe) 6.81 (d, J=1.5 Hz, 1H, ArH) 6.91-6.95 (m, 1.7H, ArH and NH) 7.18 (br, 0.63H, NH) 7.51 (d, J=7.8 Hz, 1H, ArH) 7.59-7.64 (m, 1H, ArH) 7.79-7.86 (m, 3H, ArH). MS(EI): 352.

Example 62

Isopropyl 2-(4-isopropyl-2-methoxyphenyl)-1,3-dioxo-2,3-dihydro-1H-inden-2-ylcarbamate The title compound (150 mg, 23%) was obtained in a similar manner as described in EXAMPLE 75.

mp: 159-161° C.

$^1$H-NMR (300 MHz, CDCl$_3$) δ 1.10-1.17 (m, 12H, CH$_3$) 2.82 (septet, J=6.9 Hz, 1H, CH) 3.48 (s, 3H, OMe) 4.76 (m, 1H, CH) 5.83 (s, 1H, NH) 6.62 (d, J=1.5 Hz, 1H, ArH) 6.88-6.93 (m, 1H, ArH) 7.45-7.49 (m, 1H, ArH) 7.80-7.84 (m, 2H, ArH) 7.97-8.01 (m, 2H, ArH). MS(EI): 395.

Example 63

1-(2-(4-Isopropyl-2-methoxyphenyl)-1,3-dioxo-2,3-dihydro-1H-inden-2-yl)-3-methoxy urea A solution of 2-amino-2-(4-isopropyl-2-methoxyphenyl)-2H-inden-1,3-dione (0.50 g, 1.61 mmol) in anhydrous THF (20 ml) was added triphosgene (0.528 g, 1.77 mmol) and stirred for 15 min. The reaction mixture was concentrated and was dissolved in anhydrous THF (20 ml) and was added O-methyl-hydroxylamine hydrochloride (0.28 g, 4.04 mmol) was stirred for 2 hrs at room temperature. The reaction mixture was oncentrated and was purified using silica gel column chromatography (1:1=ethylacetate:hexane) to afford the title compound (420 mg, 69%).

mp: 153-155° C.

$^1$H-NMR (300 MHz, CDCl$_3$) δ 1.25 (dd, J=1.5 Hz, J=6.9 Hz, 6H, CH$_3$) 2.91 (septet, J=6.9 Hz, 1H, CH) 2.97 (s, 1H, NH) 3.45 (s, 3H, OCH₃) 4.02 (s, 3H, OCH₃) 5.51 (br, 1H, NH) 6.76 (d, J=1.5 Hz, 1H, ArH) 7.00 (dd, J=1.5 Hz, J=7.8 Hz, 1H, ArH) 7.47 (d, J=7.8 Hz, 1H, ArH) 7.60-7.65 (m, 1H, ArH) 7.76-7.81 (m, 1H, ArH) 7.89-7.95 (t, J=8.4 Hz, 2H, ArH). MS(EI): 382.

Example 64

Ethyl 2-(4-isopropyl-2-methoxyphenyl)-1,3-dioxo-2,3-dihydro-1H-inden-2-ylcarbamate A solution of 2-amino-2-(4-isopropyl-2-methoxyphenyl)-2H-inden-1,3-dione (0.80 g, 2.58 mmol) in anhydrous THF (20 ml) was added triphosgene (0.84 g, 2.84 mmol) and stirred for 15 min. The reaction mixture was concentrated and was dissolved in ethanol (20 ml) was stirred for 2 hrs at room temperature to afford the title compound (0.95 g, 96%).

mp: 149-150° C.

¹H-NMR (300 MHz, CDCl₃) δ 1.17-1.24 (m, 9H, CH₃) 2.83 (septet, J=6.9 Hz, 1H, CH) 3.49 (s, 3H, OCH₃) 4.02 (q, 2H, CH₂) 5.89 (br, 1H, NH) 6.62 (s, 1H, ArH) 6.89 (d, J=8.1 Hz, 1H, ArH) 7.46 (d, J=8.1 Hz, 1H, ArH) 7.80-7.83 (m, 2H, ArH) 7.98-8.01 (m, 2H, ArH). MS(EI): 381.

Example 65

N-(2-Bromo-2-(4-isopropyl-2-methoxyphenyl)-1,3-dioxo-2,3-dihydro-1H-inden-4-yl)acetamide A solution of N-(2-hydroxy-2-(4-isopropyl-2-methoxyphenyl)-1,3-dioxo-2,3-2,3-dihydro-1H-inden-4-yl)acetamide (0.25 g, 0.68 mmol) in dichloromethane (10 ml) and was added thionyl bromide (0.08 mL, 1.02 mmol) and DMF (2 drops) was stirred for 2 hrs at room temperature. The reaction mixture was extracted with dichloromethane and was purified using silica gel column chromatography (20% ethylacetate in hexane) to afford the title compound (0.22 g, 75%).

mp: 143-145° C.

¹H-NMR (300 MHz, CDCl₃) δ 1.24 (d, J=6.9 Hz, 6H, CH₃) 2.63 (s, 3H, NAc) 2.91 (septet, J=6.9 Hz, 1H, CH) 3.41 (s, 3H, OCH₃) 6.61 (d, J=1.2 Hz, 1H, ArH) 6.98 (dd, J=8.1 Hz, J=1.2 Hz, 1H, ArH) 7.70 (d, J=8.1 Hz, 1H, ArH) 7.81 (d, J=7.8 Hz, 1H, ArH) 7.86-7.91 (m, 1H, ArH) 9.00 (d, J=8.4 Hz, 1H, ArH) 10.31 (br, 1H, NH). MS(EI): 430.2.

Example 66

N-(2-Amino-2-(4-isopropyl-2-methoxyphenyl)-1,3-dioxo-2,3-dihydro-1H-inden-4-yl)acetamide A solution of N-(2-azido-2-(4-isopropyl-2-methoxyphenyl)-1,3-dioxo-2,3-2,3-dihydro-1H-inden-4-yl)acetamide (115 mg, 0.29 mmol) in methanol (5 ml) and was added triphenylphosphine (92 mg, 0.35 mmol) and water (1 mL) was stirred for 2.5 hrs at 50° C. The reaction mixture was concentrated and purified using silica gel column chromatography (30% ethylacetate in hexane, 1% triethylamine) to afford the title compound (75 mg, 70%).

mp: 183-185° C.

¹H-NMR (300 MHz, CDCl₃) δ 1.23 (d, J=6.9 Hz, 6H, CH₃) 1.99 (br, 2H, NH₂) 2.24 (s, 3H, NAc) 2.88 (septet, J=6.9 Hz, 1H, CH) 3.35 (s, 3H, OCH₃) 6.59 (d, J=1.5 Hz, 1H, ArH) 6.98 (dd, J=7.8 Hz, J=1.5 Hz, 1H, ArH) 7.60 (d, J=7.8 Hz, 1H, ArH) 7.66 (d, J=7.2 Hz, 1H, ArH) 7.84 (t, J=7.8 Hz, 1H, ArH) 8.93 (d, J=8.1 Hz, 1H, ArH) 10.2 (br, 1H, NH). MS(EI): 366.

Example 67

N,N'-(2-(4-Isopropyl-2-methoxyphenyl)-1,3-dioxo-2,3-dihydro-1H-inden-2,4-diyl)diacetamide A solution of N-(2-amino-2-(4-isopropyl-2-methoxyphenyl)-1,3-dioxo-2,3-dihydro-1H-indene-4-yl)acetamide (0.20 g, 0.54 mmol) in dichloromethane (10 mL) and was added triethylamine (0.23 mL, 1.6 mmol) and acetyl chloride (0.040 mL, 0.56 mmol) and then stirred for overnight. The reaction mixture was extracted with dichloromethane and purified using silica gel column chromatography (50% ethylacetate in hexane) to afford the title compound (210 mg, 95%).

mp: 241-243° C.

¹H-NMR (300 MHz, CDCl₃) δ 1.19 (d, J=6.9 Hz, 6H, CH₃) 2.05 (s, 3H, NAc) 2.23 (s, 3H, NAc) 2.85 (septet, J=6.9 Hz, 1H, CH) 3.55 (s, 3H, OCH₃) 6.65-6.74 (m, 2H, ArH and NH) 6.91 (dd, J=8.1 Hz, J=1.5Hz, 1H, ArH) 7.39 (d, J=8.1 Hz, 1H, ArH) 7.62 (d, J=7.5 Hz, 1H, ArH) 7.78 (t, J=8.1 Hz, 1H, ArH) 8.86 (d, J=8.4 Hz, 1H, ArH) 10.1 (br, 1H, NH). MS(EI): 408.

Example 68

2-(1,3-Dioxo-2-propionamido-2,3-dihydro-1H-inden-2-yl)-5-isopropylphenyl propionate A solution of 9b-amino-4b-hydroxy-7-isopropyl-4bH-benzo[d]indeno[1,2-b]furan-10(9bH)-one (0.10 g, 0.34 mmol) in dichloromethane (5 ml) was added triethylamine (0.14 mL, 1.02 mmol) and propionyl chloride (32.5 μL, 0.37 mmol) at 0° C. and then stirred for 4 hrs at room temperature. The reaction mixture was extracted with dichloromethane and purified using silica gel column chromatography (40% ethylacetate in hexane) to afford the title compound (116 mg, 85%).

mp: 173-175° C.

¹H-NMR (300 MHz, CDCl₃) δ 1.07-1.19 (m, 9H, CH₃) 1.23-1.33 (m, 3H, CH₃) 2.27 (q, J=7.5 Hz, 2H, CH₂) 2.68 (q, J=7.5 Hz, 2H, CH₂) 2.84 (septet, J=6.9 Hz, 1H, CH) 6.69 (s, 1H, NH) 6.86 (d, J=1.5 Hz, 1H, ArH) 7.06 (dd, J=1.5 Hz, J=8.1 Hz, 1H, ArH) 7.35 (d, J=8.1 Hz, 1H, ArH) 7.80-7.83 (m, 2H, ArH) 7.95-7.98 (m, 2H, ArH). MS(EI): 407.

Example 69

2-(1,3-Dioxo-2-pentanamido-2,3-dihydro-1H-inden-2-yl)-5-isopropylphenyl pentanoate A solution of 9b-amino-4b-hydroxy-7-isopropyl-4bH-benzo[d]indeno[1,2-b]furan-10(9bH)-one (0.15 g, 0.50 mmol) in dichloromethane (5 ml) was added triethylamine (0.21 mL, 1.52 mmol) and valeroyl chloride (74 μL, 0.61 mmol) at 0° C. and then stirred for overnight at room temperature. The reaction mixture was extracted with dichloromethane and purified using silica gel column chromatography (30% ethylacetate in hexane) to afford the title compound (150 mg, 68%).

mp: 128-130° C.

¹H-NMR (300 MHz, CDCl₃) δ 0.89 (t, J=7.2 Hz, 3H, CH₃) 0.99 (t, J=7.2 Hz, 3H, CH₃) 1.18 (d, J=6.9 Hz, 6H, CH₃) 1.23-1.40 (m, 2H, CH₂) 1.42-1.62 (m, 4H, CH₂) 1.72-1.82 (m, 2H, CH₂) 2.43 (t, J=7.5 Hz, 2H, CH₂) 2.65 (t, J=7.8 Hz, 2H, CH₂) 2.84 (septet, J=6.9 Hz, 1H, CH) 6.67 (s, 1H, NH) 6.85 (d, J=1.5 Hz, 1H, ArH) 7.06 (dd, J=1.5 Hz, J=8.4 Hz, 1H, ArH) 7.34 (d, J=8.4 Hz, 1H, ArH) 7.79-7.84 (m, 2H, ArH) 7.93-7.97 (m, 2H, ArH). MS(EI): 463.

Example 70

2-(2-Benzamido-1,3-dioxo-2,3-dihydro-1H-inden-2-yl)-5-isopropylphenyl benzoate A solution of 9b-amino-4b-hydroxy-7-isopropyl-4bH-benzo[d]indeno[1,2-b]furan-10(9bH)-one (0.25 g, 0.85 mmol) in dichloromethane (15 ml) was added diisopropylethylamine (0.73 mL, 4.22 mmol) and benzoyl chloride (0.29 mL, 2.54 mmol) at 0° C. and then stirred for overnight at room temperature. The reaction mixture was extracted with dichloromethane and purified using silica gel column chromatography (20% ethylacetate in hexane) to afford the title compound (280 mg, 66%).

mp: 138-140° C.
$^1$H-NMR (300 MHz, CDCl$_3$) δ 1.22 (d, J=6.9 Hz, 6H, CH$_3$) 2.90 (septet, J=6.9 Hz, 1H, CH) 7.00 (d, J=1.5 Hz, 1H, ArH) 7.16 (dd, J=1.5 Hz, J=8.1 Hz, 1H, ArH) 7.34-7.61 (m, 9H, ArH) 7.73-7.76 (m, 4H, ArH) 7.77-7.86 (m, 2H, ArH) 8.10-8.12 (m, 2H, ArH). MS(EI): 503.

Example 71

2-(2-Acetoxy-1,3-dioxo-2,3-dihydro-1H-inden-2-yl)-6-methylpyridin-3-yl acetate The title compound was obtained in a similar manner as described in EXAMPLE 2.
$^1$H-NMR (200 MHz, CDCl$_3$): δ 8.33 (d, J=7.7 Hz, 1H), 7.80 (t, J=7.7 Hz, 1H), 7.61 (t, J=7.6 Hz, 1H), 7.52-7.44 (m, 2H), 7.26 (d, J=8.0 Hz, 1H), 2.59 (s, 3H), 2.35 (s, 3H), 2.30 (s, 3H).

Example 72

2-Hydroxy-2-(4-hydroxy-5-methylpyridin-3-yl)-1H-inden-1,3(2H)-dione

The title compound was obtained in a similar manner as described in EXAMPLE 24.
$^1$H-NMR (200 MHz, DMSO-d$_6$): δ 10.5 (s, 1H), 8.15 (d, J=8.0 Hz, 1H), 7.90 (m, 2H), 7.65 (m, 2H), 7.52 (d, J=8.5 Hz, 1H), 7.38 (d, J=8.6 Hz, 1H), 2.51 (s, 3H).

Example 73

2-(5-Chloro-3-hydroxypyridin-2-yl)-2-hydroxy-1H-inden-1,3(2H)-dione

The title compound was obtained in a similar manner as described in EXAMPLE 24.
$^1$H-NMR (200 MHz, CDCl$_3$): δ 8.32 (d, J=7.9 Hz, 1H), 8.08 (m, 1H), 7.89 (td, J=8.2, 1.2 Hz, 1H), 7.65 (t, J=7.0 Hz, 1H), 7.42 (d, J=2.0 Hz, 1H), 7.32 (d, J=1.4 Hz, 1H).

Example 74

2-2-Acetoxy-1,3-dioxo-2,3-dihydro-1H-inden-2-yl

A solution of 4b,9b-dihyroxy-7-methyl-4bH-benzo[d]indeno[1,2-b]furan-10(9bH)-one (0.25 g, 0.85 mmol) in anhydrous dichloromethane (50 ml) was added anhydrous acetic acid (0.7 ml, 7.4 mmol), pyridine (0.3 ml, 3.7 mmol), 4-dimethylaminopyridine (0.1 g) and then stirred for 3 hrs at room temperature. The reaction mixture was extracted with dichloromethane, the concentrated organic layer was purified using silica gel column chromatography (ethylacetate:hexane=1:8) to afford the title compound (1.1 g, 84%).

m.p: 145-147° C.
$^1$H-NMR (300 MHz, CDCl$_3$): δ 2.07 (s, 3H, OAc), 2.19 (s, 3H, OAc), 2.31 (s, 3H, CH$_3$), 6.80 (s, 1H, ArH), 7.08 (d, J=8.1 Hz, 1H, ArH), 7.57 (d, J=8.1 Hz, 1H, ArH), 7.86-8.02 (m, 4H, ArH). MS(EI): 352.

Example 75

2-Hydroxy-2-(6-hydroxyquinolin-7-yl)-1H-inden-1,3(2H)-dione

The title compound was obtained in a similar manner as described in EXAMPLE 24.
$^1$H-NMR (200 MHz, CDCl$_3$): δ 8.86 (d, J=8.5 Hz, 1H), 8.75 (m, 1H), 8.35 (s, 1H), 8.05-7.88 (m, 3H), 7.75-7.55 (m, 3H), 7.36 (d, J=9.1 Hz, 1H), 6.87 (s, 1H).

Example 76

Butyric acid 2-(2-butyrylamino-1,3-dioxo-indan-2-yl)-5-isopropyl-phenyl ester A solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) was added triethylamine (0.20 g, 2.01 mmol) and butyryl chloride (0.18 g, 1.69 mmol) at room temperature and then stirred for 3 hrs. The reaction mixture was diluted in ethylacetate, and washed with water several time. The organic layer was dried, filtered, and purified using silica gel column chromatography (ethylacetate:hexane=1:4 to 1:2) to afford the title compound (230 mg, 79%).

$^1$H-NMR (300 MHz, CDCl$_3$) δ 0.95 (t, J=7.5 Hz, 3H, CH$_3$) 1.08 (t, J=7.5 Hz, 3H, CH$_3$) 1.18 (d, J=6.9 Hz, 6H, CH$_3$) 1.57-1.67 (m, 2H, CH$_2$) 1.78-1.86 (m, 2H, CH$_2$) 2.23 (t, J=7.5 Hz, 2H, CH$_2$) 2.64 (t, J=7.5 Hz, 2H, CH$_2$) 2.82-2.86 (m, 1H, CH) 6.61 (s, 1H, NH) 6.85 (d, J=1.5 Hz, 1H, ArH) 7.06 (dd, J=1.5, 8.1 Hz, 1H, ArH) 7.33 (d, J=8.1 Hz, 1H, ArH) 7.80-7.85 (m, 2H, ArH) 7.94-7.98 (m, 2H, ArH).

Example 77

Octanoic acid 7-isopropyl-9b-octanoylamino-10-oxo-9b,10-dihydro-5-oxa-indeno[2,1-a]inden-4b-yl ester A solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) was added triethylamine (0.20 g, 2.01 mmol) and octanoyl chloride (0.27 g, 1.67 mmol) and then stirred for 28 hrs. The reaction mixture was concented and extracted with ethylacetate. The concentrated organic layer was purified using silica gel column chromatography (ethylacetate:hexane=1:6 to 1:4) to afford the title compound as a syrup (55 mg, 15%).

$^1$H-NMR (300 MHz, CDCl$_3$) δ 0.88 (t, J=7.5 Hz, 3H, CH$_3$) 1.18 (d, J=6.9 Hz, 6H, CH$_3$) 1.26-1.45 (m, 12H, CH$_2$) 1.54-1.65 (m, 4H, CH$_2$) 1.73-1.83 (m, 2H, CH$_2$) 2.24 (t, J=7.8 Hz, 2H, CH$_2$) 2.34 (t, J=7.5 Hz, 2H, CH$_2$) 2.65 (t, J=7.5 Hz, 2H, CH$_2$) 2.80-2.89 (m, 1H, CH) 6.61 (s, 1H, NH) 6.85 (d, J=1.5 Hz, 1H, ArH) 7.06 (dd, J=1.8, 8.4 Hz, 1H, ArH) 7.33 (d, J=8.4 Hz, 1H, ArH) 7.79-7.84 (m, 2H, ArH) 7.94-7.99 (m, 2H, ArH).

Example 78

Hexanoic acid 2-(2-hexanoylamino-1,3-dioxo-indan-2-yl)-5-isopropyl-phenyl ester

A solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) was added triethylamine (0.20 g, 2.01 mmol) and hexanoyl chloride (0.22 g, 1.69 mmol) and then stirred for 5 hrs. The reaction mixture was concented and extracted with ethylacetate. The concentrated organic layer was purified using silica gel column chromatography (ethylacetate:hexane=1:6 to 1:4) to afford the title compound as a syrup (0.14 g, 46%).

$^1$H-NMR (300 MHz, CDCl$_3$) δ 0.88 (t, J=6.9 Hz, 3H, CH$_3$) 0.95 (t, J=6.9 Hz, 3H, CH$_3$) 1.18 (d, J=6.9 Hz, 6H, CH$_3$) 1.25-1.37 (m, 6H, CH$_2$) 1.40-1.47 (m, 2H, CH$_2$) 1.55-1.65 (m, 2H, CH$_2$) 1.74-1.84 (m, 2H, CH$_2$) 2.24 (t, J=7.5 Hz, 2H, CH$_2$) 2.65 (t, J=7.5 Hz, 2H, CH$_2$) 280-2.89 (m, 1H, CH) 6.60 (s, 1H, NH) 6.85 (d, J=1.8 Hz, 1H, ArH) 7.05 (dd, J=1.8, 8.1 Hz, 1H, ArH) 7.33 (d, J=8.4 Hz, 1H, ArH) 7.80-7.84 (m, 2H, ArH) 7.93-7.98 (m, 2H, ArH).

Example 79

Heptanoic acid 2-(2-heptanoylamino-1,3-dioxo-indan-2-yl)-5-isopropyl-phenyl ester A solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) was added triethylamine (0.20 g, 2.01 mmol) and heptanoyl chloride (0.25 g, 1.69 mmol) and then stirred for 3 hrs. The reaction mixture was concented and extracted with ethylacetate. The concentrated organic layer was purified using silica gel column chromatography (ethylacetate:hexane=1:6 to 1:4) to afford the title compound as a syrup (0.21 g, 60%).

$^1$H-NMR (300 MHz, CDCl$_3$) δ 0.85-0.94 (m, 6H, CH$_3$) 1.18 (d, J=7.2 Hz, 6H, CH$_3$) 1.25-1.37 (m, 10H, CH$_2$) 1.54-1.63 (m, 4H, CH$_2$) 1.73-1.80 (m, 2H, CH$_2$) 2.24 (t, J=7.5 Hz, 2H, CH$_2$) 2.65 (t, J=7.5 Hz, 2H, CH$_2$) 2.82-2.86 (m, 1H, CH) 6.60 (s, 1H, NH) 6.85 (d, J=1.5 Hz, 1H, ArH) 7.05 (dd, J=1.5, 8.4 Hz, 1H, ArH) 7.33 (d, J=8.1 Hz, 1H, ArH) 7.80-7.83 (m, 2H, ArH) 7.95-7.98 (m, 2H, ArH).

Example 80

2,2-Dimethyl-propionic acid 2-(1,3-dioxo-2-pentanoylamino-indan-2-yl)-5-isopropyl-phenyl ester A solution of pentanoic acid [2-(2-hydroxy-4-isopropyl-phenyl)-1,3-dioxo-indan-2-yl]-amide (0.10 g, 0.26 mmol) in anhydrous methylene chloride (10 ml) was added triethylamine (0.03 g, 0.31 mmol) and pivaloyl chloride (0.047 g, 0.39 mmol) and then stirred for 2 hrs. The reaction mixture was concented and extracted with ethylacetate. The concentrated organic layer was purified using silica gel column chromatography (ethylacetate:hexane=1:4) to afford the title compound (0.11 g, 91%).

$^1$H-NMR (300 MHz, CDCl$_3$) δ 0.88 (t, J=7.2 Hz, 3H, CH$_3$) 1.17 (d, J=6.9 Hz, 6H, CH$_3$) 1.44-1.25 (m, 2H, CH$_2$) 1.50 (s, 9H, CH$_3$) 1.53-1.61 (m, 2H, CH$_2$) 2.23 (t, J=7.2 Hz, 2H, CH$_2$) 2.78-2.88 (m, 1H, CH) 6.77-6.79 (m, 2H, NH, ArH) 6.97 (d, J=1.2, 8.1 Hz, 1H, ArH) 7.08 (d, J=1.2, 8.1 Hz, 1H, ArH) 7.79-7.82 (m, 2H, ArH) 7.95-7.98 (m, 2H, ArH).

Example 81

2-(4-amino-1,3-dioxo-2-pentanamido-2,3-dihydro-1H-inden-2-yl)-5-isopropylphenyl pentanoate Iron powder (0.03 g, 0.6 mmol), conc. HCl (0.05 ml), and water (0.5 ml) were added in that order to a solution of 5-isopropyl-2-(4-nitro-1,3-dioxo-2-pentanamido-2,3-dihydro-1H-inden-2-yl)phenyl pentanoate (43 mg, 0.08 mmol) in ethanol (5 ml). The reaction mixture was heated for 1 hrs under reflux. The reaction mixture was hot filtered off, the filtrate was concentrated in a vacuum and purified by column chromatography (ethylacetate:hexane=1:4 to 1:2) to afford the title compound (22 mg, 55%).

$^1$H-NMR (300 MHz, CDCl$_3$) δ 0.90 (t, J=7.2 Hz, 3H, CH$_3$) 0.98 (t, J=7.2 Hz, 3H, CH$_3$) 1.16-1.61 (m, 12H, CH$_2$, CH$_3$) 1.73 (t, J=7.5 Hz, 2H, CH$_2$) 2.25 (t, J=7.5 Hz, 2H, CH$_2$) 2.63 (t, J=8.1 Hz, 2H, CH$_2$) 2.80-2.89 (m, 1H, CH) 5.69 (s, 2H, NH$_2$) 6.62 (s, 1H, NH) 6.77 (d, J=8.1 Hz, 1H, ArH) 6.85 (s, 1H, ArH) 7.05 (d, J=6.9 Hz, 1H, ArH) 7.13 (d, J=6.9 Hz, 1H, ArH) 7.30 (d, J=8.1 Hz, 1H, ArH) 7.40 (t, J=7.8 Hz, 1H, ArH).

Example 82

2-(4-Amino-2-hexanamido-1,3-dioxo-2,3-dihydro-1H-inden-2-yl)-5-isopropylphenyl hexanoate Iron powder (0.03 g, 0.5 mmol), conc. HCl (0.05 ml), and water (0.5 ml) were added in that order to a solution of 2-(2-hexanamido-4-nitro-1,3-dioxo-2,3-dihydro-1H-inden-2-yl)-5-isopropylphenyl hexanoate (40 mg, 0.07 mmol) in ethanol (5 ml). The reaction mixture was heated for 1 hrs under reflux. The reaction mixture was hot filtered off, the filtrate was concentrated in a vacuum and purified by column chromatography (ethylacetate:hexane=1:4 to 1:2) to afford the title compound (21 mg, 57%).

$^1$H-NMR (300 MHz, CDCl$_3$) δ 0.79-0.96 (m, 6H, CH$_3$) 1.18 (dd, J=6.9 Hz, 6H, CH$_3$) 1.22-1.32 (m, 6H, CH$_3$) 1.36-1.41 (m, 2H, CH$_2$) 1.47-1.63 (m, 3H, CH$_2$) 1.73-1.82 (m, 1H, CH$_2$) 2.24 (t, J=7.5 Hz, 2H, CH$_2$) 2.65 (t, J=7.8 Hz, 2H, CH$_2$) 2.80-2.89 (m, 1H, CH) 5.66 (s, 2H, NH2) 6.59 (s, 1H, NH) 6.80 (d, J=8.1 Hz, 1H, ArH) 6.86 (d, J=1.8 Hz, 1H, ArH) 7.05 (dd, J=1.8, 8.1 Hz, 1H, ArH) 7.15 (d, J=7.2 Hz, 1H, ArH) 7.30 (d, J=8.4 Hz, 1H, ArH) 7.44 (d, J=7.8 Hz, 1H, ArH).

Example 83

2-(4-Amino-2-heptanamido-1,3-dioxo-2,3-dihydro-1H-inden-2-yl)-5-isopropylphenyl heptanoate Iron powder (0.03 g, 0.5 mmol), conc. HCl (0.05 ml), and water (0.5 ml) were added in that order to a solution of 2-(2-heptanamido-4nitro-1,3-dioxo-2,3-dihydro-1H-inden-2-yl)-5-isopropylphenyl heptanoate (60 mg, 0.10 mmol) in ethanol (5 ml). The reaction mixture was heated for 1 hrs under reflux. The reaction mixture was hot filtered off, the filtrate was concentrated in a vacuum and purified by column chromatography (ethylacetate:hexane=1:6 to 1:4) to afford the title compound (20 mg, 36%).

$^1$H-NMR (300 MHz, CDCl$_3$) δ 0.79-0.97 (m, 6H, CH$_3$) 1.18 (dd, J=6.9 Hz, 6H, CH$_3$) 1.25-1.49 (m, 12H, CH$_2$) 1.58 (t, J=7.2 Hz, 2H, CH$_2$) 1.82 (t, J=7.2 Hz, 2H, CH$_2$) 2.22 (t, J=7.5 Hz, 2H, CH$_2$) 2.65 (t, J=7.5 Hz, 2H, CH$_2$) 2.80-2.89 (m, 1H, CH) 5.66 (s, 2H, NH$_2$) 6.59 (s, 1H, NH) 6.79 (d, J=8.1 Hz, 1H, ArH) 6.85 (d, J=1.5 Hz, 1H, ArH) 7.05 (dd, J=1.8, 8.4 Hz,

1H, ArH) 7.15 (d, J=7.2 Hz, 1H, ArH) 7.29 (d, J=8.1 Hz, 1H, ArH) 7.42 (t, J=8.1 Hz, 1H, ArH).

Example 84

2-(4-Amino-1,3-dioxo-2-propionamido-2,3-dihydro-1H-inden-2-yl)-5-isopropylphenyl propionate Iron powder (0.03 g, 0.5 mmol), conc. HCl (0.05 ml), and water (0.5 ml) were added in that order to a solution of 5-isopropyl-2-(4-nitro-1,3-dioxo-2-propionamido-2,3-dihydro-1H-inden-2-yl)phenyl propionate (40 mg, 0.08 mmol) in ethanol (5 ml). The reaction mixture was heated for 1 hrs under reflux. The reaction mixture was hot filtered off, the filtrate was concentrated in a vacuum and purified by column chromatography (ethylacetate:hexane=1:4 to 1:2) to afford the title compound (28 mg, 75%).

$^1$H-NMR (300 MHz, CDCl$_3$) δ 1.18 (dd, J=6.9 Hz, 6H, CH$_3$) 1.27 (dd, J=3.3, 7.5 Hz, 6H, CH$_3$) 2.29 (q, J=7.5 Hz, 2H, CH$_2$) 2.70 (q, J=7.5 Hz, 2H, CH$_2$) 2.80-2.89 (m, 1H, CH) 5.67 (s, 2H, NH$_2$) 6.60 (s, 1H, NH) 6.80 (d, J=8.1 Hz, 1H, ArH) 6.87 (d, J=1.5 Hz, 1H, ArH) 7.06 (dd, J=1.5, 6.9 Hz, 1H, ArH) 7.16 (d, J=7.2 Hz, 1H, ArH) 7.32 (t, J=8.1 Hz, 1H, ArH) 7.43 (t, J=7.5 Hz, 1H, ArH).

Example 85

2-(4-Amino-2-butyramido-1,3-dioxo-2,3-dihydro-1H-inden-2-yl)-5-isopropylphenyl butyrate Iron powder (0.07 g, 1.3 mmol), conc. HCl (0.05 ml), and water (1 ml) were added in that order to a solution of 2-(2-butyramido-4-nitro-1,3-dioxo-2,3-dihydro-1H-inden-2-yl)-5-isopropylphenyl butyrate (90 mg, 0.18 mmol) in ethanol (5 ml). The reaction mixture was heated for 1 hrs under reflux. After filtration at high temperature, the filtrate was concentrated in a vacuum and purified using column chromatography (ethylacetate:hexane=1:4 to 1:2) to afford the title compound (70 mg, 83%).

$^1$H-NMR (300 MHz, CDCl$_3$) δ 0.95 (t, J=7.5 Hz, 3H, CH$_3$) 1.07 (t, J=7.5 Hz, 3H, CH$_3$) 1.18 (d, J=6.9 Hz, 6H, CH$_3$) 1.64 (q, J=7.5, 14.7 Hz, 2H, CH$_2$) 1.80 (q, J=7.5, 14.7 Hz, 2H, CH$_2$) 2.23 (t, J=7.5 Hz, 2H, CH$_2$) 2.64 (t, J=7.5 Hz, 2H, CH$_2$) 2.80-2.89 (m, 1H, CH) 5.70 (s, 2H, NEU 6.62 (s, 1H, NH) 6.74 (d, J=8.4 Hz, 1H, ArH) 6.86 (d, J=1.5 Hz, 1H, ArH) 7.05 (dd, J=1.5, 8.4 Hz, 1H, ArH) 7.12 (d, J=7.2 Hz, 1H, ArH) 7.28 (t, J=7.5 Hz, 1H, ArH) 7.38 (t, J=7.5 Hz, 1H, ArH).

Example 86

N-(2-(2-Hydroxy-1,3-dioxo-2,3-dihydro-1H-inden-2-yl)-4,5-dimethylphenyl)acetamide N-(3,4-dimethylphenyl)acetamide (915 mg, 5.62 mmol) and ninhydrin (1.00 g, 5.62 mmol) were dissolved in conc. sulfuric acid (20 mL) and stirred at room temperature for 1.5 hrs. The reaction was stopped by slowing pouring the solution to 150 g of ice and stirring. The reaction mixture was extracted with ethylacetate and water, washed with brine. The washed organic layer was dried over sodium sulfate, concentrated in a vacuum, and purified through column chromatography (30% ethylacetate in hexane) to afford the title compound (yellow solid, 800 mg, 44%).

$^1$H-NMR (300 MHz, CDCl$_3$) δ 2.02 (s, 3H, NAc) 2.20 (s, 3H, CH$_3$) 2.22 (s, 3H, CH$_3$) 6.11 (s, 1H, ArH) 7.03 (s, 1H, ArH) 7.99-8.02 (m, 2H, ArH) 8.13-8.16 (m, 2H, ArH).

Example 87

N-(2-(2-Hydroxy-1,3-dioxo-2,3-dihydro-1H-inden-2-yl)-4,5-dimethylphenyl)propionamide N-(3,4-dimethylphenyl)propion amide (500 mg, 2.82 mmol) and ninhydrin (500 mg, 2.82 mmol) were dissolved in conc. sulfuric acid (10 mL) and stirred at room temperature for 1.5 hrs. The reaction was stopped by slowing pouring the solution to 150 g of ice and stirring. The reaction mixture was extracted with ethylacetate and water, washed with brine. The washed organic layer was dried over sodium sulfate, concentrated in a vacuum, and purified through silica gel column chromatography (30% ethylacetate in hexane) to afford the title compound (yellow solid, 430 mg, 45%).

$^1$H-NMR (300 MHz, DMSO) δ 1.26 (t, J=7.5 Hz, 3H, CH$_3$) 2.14 (s, 6H, CH$_3$) 3.06-3.58 (m, 2H, CH$_2$) 6.84 (s, 1H, ArH/OH) 7.16 (s, 1H, ArH/OH) 7.48 (s, 1H, ArH/OH) 7.56-7.61 (m, 1H, ArH) 7.70 (d, J=7.8 Hz, 1H, ArH) 7.80-7.86 (m, 2H, ArH) 7.95-8.01 (m, 1H, ArH).

Example 88

N-(5-Ethyl-2-(2-hydroxy-1,3-dioxo-2,3-dihydro-1H-inden-2-yl)phenyl)acetamide

N-(3-ethylphenyl)acetamide (500 mg, 3.06 mmol) and ninhydrin (546 mg, 3.06 mmol) were dissolved in conc. sulfuric acid (10 mL) and stirred at room temperature for 3 hrs. The reaction was stopped by slowing pouring the solution to 150 g of ice and stirring. The reaction mixture was extracted with ethylacetate and water, washed with brine. The washed organic layer was dried over sodium sulfate, concentrated in a vacuum, and purified through silica gel column chromatography (30% ethylacetate in hexane) to afford the title compound (90 mg, 9%).

$^1$H-NMR (300 MHz, CDCl$_3$) δ 1.17 (t, J=7.5 Hz, 3H, CH$_3$) 2.45 (s, 3H, NAc) 2.57 (q, J=7.5 Hz, 2H, CH$_2$) 6.30 (d, J=7.5 Hz, 1H, ArH) 6.81 (dd, J=7.5 Hz, J=1.5 Hz, 1H, ArH) 7.09 (d, J=1.5 Hz, 1H, ArH) 7.98-8.03 (m, 2H, ArH) 8.11-8.15 (m, 2H, ArH).

Example 89

N-(2-(2-Hydroxy-1,3-dioxo-2,3-dihydro-1H-inden-2-yl)-4,5-dimethylphenyl)butyramide N-(3,4-dimethylphenyl)butyramide (1.00 mg, 5.61 mmol) and ninhydrin (1.07 mg, 5.61 mmol) were dissolved in conc. sulfuric acid (15 mL) and stirred at room temperature for 5 hrs. The reaction was stopped by slowing pouring the solution to 150 g of ice and stirring. The reaction mixture was extracted with ethylacetate and water, washed with brine. The washed organic layer was dried over sodium sulfate, concentrated in a vacuum, and purified through silica gel column chromatography (30% ethylacetate in hexane) to afford the title compound (yellow solid, 1.10 g, 56%).

$^1$H-NMR (300 MHz, CDCl$_3$) δ 1.028 (t, J=7.5 Hz, 3H, CH$_3$) 1.69-1.79 (m, 2H, CH$_2$) 2.01 (s, 3H, CH$_3$) 2.17 (s, 3H, CH$_3$) 2.43 (t, J=7.5 Hz, 2H, CH$_2$) 6.11 (s, 1H, ArH) 7.05 (s, 1H, ArH) 7.99-8.03 (m, 2H, ArH) 8.11-8.16 (m, 2H, ArH).

Example 90

N-(2-(2-Hydroxy-1,3-dioxo-2,3-dihydro-1H-inden-2-yl)-4,5-dimethylphenyl)isobutyramide N-(3,4-dimethylphenyl)isobutyramide (1.00 mg, 5.61 mmol) and ninhydrin (1.07 mg, 5.61 mmol) were dissolved in conc. sulfuric acid (15 mL) and stirred at room temperature for 5 hrs. The reaction was stopped by slowing pouring the solution to 200 g of ice and stirring. The reaction mixture was extracted with ethylacetate and water, washed with brine. The washed organic layer was dried over sodium sulfate, concentrated in a vacuum, and purified through silica gel column chromatography (30% ethylacetate in hexane) to afford the title compound (yellow solid, 1.85 g, 94%).

$^1$H-NMR (300 MHz, CDCl$_3$) δ 1.26 (d, J=6.9 Hz, 6H, CH$_3$) 2.01 (s, 3H, CH$_3$) 2.18 (s, 3H, CH$_3$) 2.68 (sept, J=6.9 Hz, 1H, CH) 6.11 (s, 1H, ArH) 7.08 (s, 1H, ArH) 7.99-8.03 (m, 2H, ArH) 8.11-8.16 (m, 2H, ArH).

Example 91

2-(4-Amino-2-octanamido-1,3-dioxo-2,3-dihydro-1H-inden-2-yl)-5-isopropylphenyl octanoate Iron powder (58 mg, 1.03 mmol) and conc. HCl (3 drops) were added in that order to a solution of 5-isopropyl-2-(4-nitro-2-octanamino-1,3-dioxo-2,3-dihydro-1H-inden-2-yl) phenyl octanoate (80 mg, 0.14 mmol) in ethanol:water (9:1, 7 ml). The reaction mixture was heated for 3 hrs under reflux. After filtration at high temperature, the filtrate was concentrated in a vacuum and purified using silica gel column chromatography (20% ethylacetate in hexane, 1% triethylamine) to afford the title compound (45 mg, 59%).

$^1$H-NMR (300 MHz, CDCl$_3$) δ 0.84-0.88 (m, 6H, CH$_3$) 1.16-1.28 (m, 16H+6H, CH$_2$+CH$_3$) 1.51-1.64 (m, 4H, CH$_2$) 2.10-2.46 (m, 4H, CH$_2$) 2.85 (sept, J=6.9 Hz, 1H, CH) 4.40 (br, 2H, NH$_2$) 5.98 (s, 1H, ArH/NH) 6.72 (s, 1H, ArH/NH) 6.89-6.96 (m, 2H, ArH) 7.22-7.34 (m, 2H, ArH) 7.40-7.43 (m, 1H, ArH).

Example 92

2-(2-Acetamido-1,3-dioxo-2,3-dihydro-1H-inden-2-yl)-5-isopropylphenyl methyl carbonate Triethylamine (0.24 ml, 1.77 mmol) and methylchloroformate (0.11 ml, 1.48 mmol) were added to N-(4b-hydroxy-7-isopropyl-10-oxo-9b,10-dihydro-4bH-benzo[d]indeno[1,2-b]furan-9b-yl)acetamide (0.50 g, 1.48 mmol) in THF (5 ml). The reaction mixture was stirred at room temperature for 12 hrs, concentrated in a vacuum to remove solvent. The reaction mixture was extracted with water and methylene chloride, and purified through silica gel column chromatography (ethylacetate:hexane=1:2) to afford the title compound (0.10 g, 14%).

$^1$H-NMR (300 MHz, CDCl$_3$) δ 1.17 (d, J=6.8 Hz, 6H), 1.89 (s, 3H), 2.84 (q, J=7.8 Hz, 1H), 3.89 (s, 3H), 6.90 (s, 1H), 7.01 (s, 1H), 7.10 (d, J=7.7 Hz, 1H), 7.44 (d, J=8.2 Hz, 1H), 7.77-7.83 (m, 2H), 7.92-7.96 (m, 2H).

Example 93

2-(2-Acetamido-1,3-dioxo-2,3-dihydro-1H-inden-2-yl)-5-isopropylphenyl pentanoate Triethylamine (0.24 ml, 1.77 mmol) and Valeroyl chloride (0.18 ml, 1.48 mmol) were added to N-(4b-hydroxy-7-isopropyl-10-oxo-9b,10-dihydro-4bH-benzo[d]indeno[1,2-b]furan-9b-yl)acetamide (0.50 g, 1.48 mmol) in THF (10 ml). The reaction mixture was stirred at room temperature for 12 hrs, concentrated in a vacuum to remove solvent. The reaction mixture was extracted with water and methylene chloride, and purified through silica gel column chromatography (ethylacetate:hexane=1:2) to afford the title compound (0.20 g, 32%).

$^1$H-NMR (300 MHz, CDCl$_3$) δ 0.99 (t, J=8.9 Hz, 3H), 1.17 (d, J=7.0 Hz, 6H), 1.44-1.52 (m, 2H), 1.75 (q, J=8.3 Hz, 2H), 2.62 (t, J=8.9 Hz, 2H), 2.83 (q, J=7.7 Hz, 1H), 6.81-6.87 (m, 2H), 7.06 (dd, J=1.3 Hz, 8.3 Hz, 1H), 7.38 (d, J=7.7 Hz, 1H), 7.79-7.85 (m, 2H), 7.92-7.98 (m, 2H).

Example 94

N-(2-(4-Acetamido-2-hydroxy-7-nitro-1,3-dioxo-2,3-dihydro-1H-inden-2-yl)-4,5-dimethylphenyl)isobutyramide N-(2,2-dihydroxy-7-nitro-1,3-dioxo-2,3-dihydro-1H-inden-4-yl)acetamide (0.20 g, 0.71 mmol) and N-(3,4-dimethylphenyl)isobutyramide (136 mg, 0.71 mmol) were dissolved in conc. sulfuric acid (5 mL) and stirred at room temperature for 3 hrs. The reaction mixture was extracted with ethylacetate and ice-water, washed with brine. The washed organic layer dried over sodium sulfate, concentrated in a vacuum, and purified through silica gel column chromatography (30% ethylacetate in hexane) to afford the title compound (30 mg, 10%).

$^1$H-NMR (300 MHz, CDCl$_3$) δ 1.27 (d, J=6.9 Hz, 6H, CH$_3$) 2.08 (s, 3H, NAc) 2.19 (s, 6H, CH$_3$) 2.69 (sept, J=6.9 Hz, 1H, CH) 6.30 (s, 1H, ArH), 7.02 (d, J=9 Hz, 1H, ArH) 7.08 (s, 1H, ArH) 8.22 (d, J=9 Hz, 1H, ArH).

Example 95

N-(2-(2-Hydroxy-1,3-dioxo-2,3-dihydro-1H-inden-2-yl)-5-isopropylphenyl)isobutyramide Ninhydrin (0.5 g, 2.80 mmol) and N-(4-isopropylphenyl) acetamide (575 mg, 2.80 mmol) were dissolved in conc. sulfuric acid (5-6 mL) and stirred at room temperature for 15 hrs. The reaction mixture was extracted with ethylacetate and ice-water, washed with brine. The washed organic layer was dried over sodium sulfate, concentrated in a vacuum, and purified through silica gel column chromatography (20% ethylacetate in hexane) to afford the title compound (320 mg, 31%).

$^1$H-NMR (300 MHz, CDCl$_3$) δ 1.19 (d, J=6.9 Hz, 6H, CH$_3$) 1.29 (d, J=6.9 Hz, 6H, CH$_3$) 2.71 (sept, J=6.9 Hz, 1H, CH) 2.81 (sept, J=6.9 Hz, 1H, CH) 6.31 (d, J=7.8 Hz, 1H, ArH) 6.83 (dd, J=1.5 Hz, J=7.8 Hz, 1H, ArH) 7.17 (d, J=1.5 Hz, 1H, ArH) 7.98-8.02 (m, 2H, ArH) 8.11-8.15 (m, 2H, ArH).

Example 96

2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate 9b-acetamido-7-isopropyl-1-nitro-10-oxo-9b,10-dihydro-4bH-benzo[d]indeno[1,2-b]furan-4b-yl butylcarbonate (0.11 g, 0.22 mmol) was completely dissolved in anhydrous ethanol (5 ml). This solution was added with iron (0.09 g, 1.66 mmol), conc. HCl (0.05 ml) and water (0.5 ml). The reaction mixture was heated for 1.5 hrs under reflux. After filtration at high temperature to remove iron, the filtrate was concentrated in a vacuum and purified using column chromatography (ethylacetate:hexane=1:2) to afford the title compound (50 mg, 50%).

¹H-NMR (300 MHz, CDCl₃) δ 0.91 (t, J=7.2 Hz, 3H, CH₃) 1.22 (dd, J=7.2 Hz, 16.8 Hz, 6H, CH₃) 1.33-1.44 (m, 2H, CH₂) 1.59-1.73 (m, 2H, CH₂) 1.95 (s, 3H, CH₃) 2.04-2.90 (m, 1H, CH) 4.07-4.46 (m, 2H, OCH₂) 5.59 (s, 1H, NH) 6.10 (s, 1H, ArH) 6.60 (d, J=8.1 Hz, 1H, ArH) 6.75 (s, 1H, ArH) 6.91 (dd, J=1.5, 7.8 Hz, 1H, ArH) 7.12 (d, J=7.2 Hz, 1H, ArH) 7.39-7.48 (m, 1H, ArH).

Example 97

2-(2-Acetamido-1,3-dioxo-2,3-dihydro-1H-inden-2-yl)-5-isopropylphenyl methylcarbamate 9b-chloro-4b-hydroxy-7-isopropyl-1-nitro-4bH-benzo[d]indeno[1,2-b]furan-10(9bH)-one (0.50 g, 1.48 mmol) was dissolved in anhydrous THF (15 ml). This solution was added with methyl isocyanate (0.12 g, 2.22 mmol), trimethylamine (0.18 g, 1.77 mmol). The reaction mixture was heated for 5 hrs under reflux. After concentrating in a vacuum to remove THF, and the remainder was diluted with methylene chrolide and washed with water many times. After drying and filtrating, the organic layer was purified using column chromatography (ethylacetate:hexane=1:2) to afford the title compound (0.25 g, 44%).
¹H-NMR (300 MHz, CDCl₃) δ 1.17 (d, J=6.9 Hz, 6H, CH₃) 2.01 (s, 3H, CH₃) 2.79-2.91 (m, 4H, CH, CH₃) 5.22 (s, 1H, NH) 6.86 (s, 1H, NH) 6.95 (s, 1H, ArH) 7.04 (d, J=7.8 Hz, 1H, ArH) 7.32 (d, J=8.4 Hz, 1H, ArH) 7.80-7.83 (m, 2H, ArH) 7.94-7.97 (m, 2H, ArH).

Example 98

Dimethyl-carbamic acid 2-(2-acetylamino-1,3-dioxo-indan-2-yl)-5-isopropyl-phenyl ester N-(4b-hydroxy-7-isopropyl-10-oxo-4b,10-dihydro-5-oxa-indeno[2,1-a]inden-9b-yl)-acetamide (0.50 g, 1.48 mmol) was dissolved in anhydrous THF (15 ml). This solution was added with Dimethyl-carbamylchrolide (0.23 g, 2.22 mmol), Trimethylamine (0.17 g, 1.77 mmol). The reaction mixture was heated for 24 hrs under reflux. After concentrating in a vacuum to remove THF, and the remainder was diluted with Ethylacetate and washed with Bicarbonate sodium aqueous solution many times. After drying and filtrating, the organic layer was purified using column chromatography (ethylacetate:hexane=1:1) to afford the title compound (0.26 g, 43%).
¹H-NMR (300 MHz, CDCl₃) δ 1.17 (d, J=6.9 Hz, 6H, CH₃) 1.98 (s, 3H, CH₃) 2.80-2.88 (sept, 1H, CH) 3.04 (s, 3H, CH₃) 3.23 (s, 3H, CH₃) 6.88 (s, 1H, ArH) 7.01 (d, J=8.1 Hz, 1H, ArH) 7.16 (s, 1H, ArH) 7.23 (d, J=8.4 Hz, 1H, ArH) 7.79-7.82 (m, 2H, ArH) 7.94-7.97 (m, 2H, ArH).

Example 99

Carbonic acid 2-(2-acetylamino-1,3-dioxo-indan-2-yl)-5-isopropyl-phenyl ester phenyl ester N-(4b-hydroxy-7-isopropyl-10-oxo-4b,10-dihydro-5-oxa-indeno[2,1-a]inden-9b-yl)-acetamide (0.50 g, 1.48 mmol) was dissolved in anhydrous THF (15 ml). This solution was added with Phenyl chroloformate (0.35 g, 2.22 mmol), Trimethylamine (0.18 g, 1.77 mmol). The reaction mixture was heated for 24 hrs under reflux. After concentrating in a vacuum to remove THF, and the remainder was diluted with Ethylacetate and washed with Bicarbonate sodium aqueous solution many times. After drying and filtrating, the organic layer was purified using column chromatography (ethylacetate:hexane=1:1) to afford the title compound (0.18 g, 26%).
¹H-NMR (300 MHz, CDCl₃) δ 1.19 (d, J=6.9 Hz, 6H, CH₃) 2.04 (s, 3H, CH₃) 2.82-2.91 (sept, 1H, CH) 6.67 (s, 1H, NH) 7.03 (s, 1H, ArH) 7.15 (d, J=8.4 Hz, 1H, ArH) 7.30-7.34 (m, 1H, ArH) 7.45-7.47 (m, 5H, ArH) 7.81-7.84 (m, 2H, ArH) 8.00-8.02 (m, 2H, ArH).

Example 100

2-(2-Acetamido-4-amino-1,3-dioxo-2,3-dihydro-1H-inden-2-yl)-5-isopropylphenyl dimethylcarbamate 2-(2-acetamido-4-nitro-1,3-dioxo-2,3-dihydro-1H-inden-2-yl)-5-isopropylphenyl dimethylcarbamate (0.20 g, 0.4 mmol) was dissolved in anhydrous ethanol (10 ml) and water (1 ml). This solution was added with iron (0.18 g, 3.2 mmol) and conc. HCl (0.03 ml). The reaction mixture was heated for 2 hrs under reflux. After filtrating and washing with MeOH, the remainder was concentrated in a vacuum and purified using column chromatography (ethylacetate:hexane=1:2) to afford the title compound (90 mg, 50%).
¹H-NMR (300 MHz, CDCl₃) δ 1.18 (d, J=6.9 Hz, 6H, CH₃) 1.98 (s, 3H, CH₃) 2.97 (s, 3H, CH₃) 2.79-2.89 (m, 1H, CH) 3.05 (s, 3H, CH₃) 3.23 (s, 3H, CH₃) 5.67 (s, 2H, NH₂) 6.81 (d, J=8.1 Hz, 1H, ArH) 6.85 (s, 1H, NH) 7.01 (d, J=8.4 Hz, 1H, ArH) 7.08 (s, 1H, ArH) 7.13-7.21 (m, 2H, ArH) 7.44 (t, J=8.1 Hz, 1H, ArH).

Example 101

2-(2-Acetamido-1,3-dioxo-2,3-dihydro-1H-inden-2-yl)-5-isopropylphenyl ethyl carbonate 9b-chrolo-4b-hydroxy-7-isopropyl-1-nitro-4bH-benzo[d]indeno[1,2-b]furan-10(9bH)-one (0.70 g, 2.07 mmol) was dissolved in anhydrous THF (15 ml). This solution was added with Ethyl chroloformate (0.32 g, 3.11 mmol) and Trimethylamine (0.25 g, 2.48 mmol). The reaction mixture was stirred for 4 hrs. After concentrating in a vacuum to remove THF, and the remainder was diluted with Methylene chrolide and washed with water many times. After drying and filtrating, the organic layer was purified using column chromatography (ethylacetate:hexane=1:4) to afford the title compound (30 mg, 3.6%).
¹H-NMR (300 MHz, CDCl₃) δ 1.16-1.28 (m, 9H, CH₃) 2.33 (s, 3H, CH₃) 2.79-2.88 (m, 1H, CH) 4.02-4.15 (m, 2H, OCH₂) 5.90 (s, 1H, NH) 6.68 (s, 1H, ArH) 7.07 (dd, J=1.5, 8.3 Hz, 1H, ArH) 7.42 (d, J=8.3 Hz, 1H, ArH) 7.81-7.90 (m, 2H, ArH) 7.96-8.02 (m, 2H, ArH).

Example 102

Ethyl acetyl(2-(2-hydroxy-4-isopropylphenyl)-1,3-dioxo-2,3-dihydro-1H-inden-2-yl)carbamate N-(4b-hydroxy-7-isopropyl-10-oxo-4b,10-dihydro-9bH-indeno[1,2-b]benzofuran-9b-yl)acetamide (0.70 g, 2.07 mmol) was dissolved in anhydrous THF (15 ml). This solution was added with Ethyl chroloformate (0.32 g, 3.11 mmol) and Trimethylamine (0.25 g, 2.48 mmol). The reaction mixture was stirred for 4 hrs. After concentrating in a vacuum to remove THF, and the remainder was diluted with Methylene chrolide and washed with water many times. After drying and filtrating, the organic layer was purified using column chromatography (ethylacetate:hexane=1:4) to afford the title compound (0.64 g, 71%).

$^1$H-NMR (300 MHz, CDCl$_3$) δ 1.18 (d, J=6.9 Hz, 6H, CH$_3$) 1.46 (t, J=7.1 Hz, 3H, CH$_3$) 2.03 (s, 3H, CH$_3$) 2.83-2.88 (m, 1H, CH) 4.31-4.38 (q, J=7.1 Hz, 2H, OCH$_2$) 6.67 (s, 1H, NH) 6.92 (s, 1H, ArH) 7.12 (dd, J=1.2, 8.2 Hz, 1H, ArH) 7.43 (d, J=8.2 Hz, 1H, ArH) 7.81-7.84 (m, 2H, ArH) 7.96-7.99 (m, 2H, ArH).

Example 103

2-(2-Acetamido-4-amino-1,3-dioxo-2,3-dihydro-1H-inden-2-yl)-5-isopropylphenyl ethylcarbamate 2-(2-acetamido-4-nitro-1,3-dioxo-2,3-dihydro-1H-inden-2-yl)-5-isopropylphenyl ethylcarbamate (0.27 g, 0.59 mmol) was dissolved in Ethanol (10 ml) and water (1 ml). This solution was added with iron (0.24 g, 4.3 mmol) and conc. HCl (0.03 ml). The reaction mixture was heated for 2 hrs under reflux. After filtrating and washing with MeOH, the remainder was concentrated in a vacuum and purified using column chromatography (ethylacetate:hexane=1:1) to afford the title compound (90 mg, 36%).

$^1$H-NMR (300 MHz, CDCl$_3$) δ 1.11-1.92 (d, J=6.9 Hz, 6H, CH$_3$) 1.95 (s, 3H, CH$_3$) 2.79-2.88 (m, 1H, CH) 3.10-3.26 (m, 2H, CH$_3$) 5.24 (s, 1H, NCH) 5.56 (s, 2H, NH$_2$) 6.21 (s, 1H, NH) 6.60 (d, J=8.4 Hz, 1H, ArH) 6.71 (s, 1H, ArH) 6.88 (d, J=7.8 Hz, 1H, ArH) 7.06 (d, J=7.5 Hz, 1H, ArH) 7.42 (t, J=7.8 Hz, 2H, ArH).

Example 104

2-(3-Methoxyphenyl)-2H-inden-1,3-dione

Sodium (1.1 g) was dissolved in anhydrous Ethanol (90 ml). This solution was added with Phthalide (4.43 g, 33.04 mmol) and m-Methoxy benzaldehyde (3.00 g, 22.03 mmol). The reaction mixture was heated for 3 hrs under reflux. The reaction mixture was concentrated in a vacuum. White solid was obtained by adding conc.HCl. And then the white solid was recrystalized in ethylacetate:hexane (=1:2) to afford the title compound (2.45 g, 44%).

$^1$H-NMR (300 MHz, CDCl$_3$) δ 3.78 (s, 3H, OCH$_3$) 6.73-6.76 (m, 2H, ArH) 6.85 (d, J=7.2 Hz, 1H, ArH) 7.26 (t, J=7.8 Hz, 1H, ArH) 7.89-7.93 (m, 2H, ArH) 8.06-8.09 (m, 2H, ArH).

Example 105 ethyl (6-(2-((ethoxycarbonyl)oxy)-4-isopropylphenyl)-5,7-dioxo-6,7-dihydro-5H-cyclopenta[b]pyridin-6-yl)carbonate 4b,9b-dihydroxy-7-isopropyl-4bH-benzofuro[2',3':3,4]cyclopenta[1,2-b]pyridin-10(9bH)-one (0.50 g, 1.68 mmol) was dissolved in THF (10 ml) and Et$_3$N (0.70 ml, 5.04 mmol). This solution was added with Ethyl chroloformate (0.40 ml, 4.20 mmol). The reaction mixture was stirred for 2 hrs. After concentrating in a vacuum, and the remainder was purified using column chromatography (ethylacetate:hexane=1:2) to afford the title compound (0.20 g, 27%).

$^1$H-NMR (300 MHz, CDCl$_3$) δ 1.19 (d, J=6.8 Hz, 6H), 1.28 (t, J=7.2 Hz, 3H), 1.32 (t, J=7.6 Hz, 3H), 2.87 (q, J=7.1 Hz, 1H), 4.10-4.18 (m, 4H), 6.92 (s, 1H), 6.20 (dd, J=1.1 Hz, 8.4 Hz, 1H), 7.73-7.79 (m, 2H), 8.33 (d, J=7.9 Hz, 1H), 9.16 (d, J=4.7 Hz, 1H).

Example 106

N-(2-(2-Hydroxy-1,3-dioxo-2,3-dihydro-1H-inden-2-yl)-4,5-dimethoxyphenyl)isobutyramide Ninhydrin (1.00 g, 5.6 mmol) was dissolved in conc.H$_2$SO$_4$ (10 ml). This solution was added with N-(3,4-dimethoxyphenyl)isobutyramide (1.25 g, 5.62 mmol) at 0° C. and stirred for 30 min under room temperature. Ice water was added with the reaction mixture, and then washed with ice water and ethylacetate. After drying and filtrating, the ethylacetate layer was purified using column chromatography (ethylacetate:hexane=1:4) to afford the title compound (1.37 g, 63%).

$^1$H-NMR (300 MHz, CDCl$_3$) δ 1.28 (d, J=6.9 Hz, 6H, CH$_3$) 2.63-2.72 (m, 1H, CH) 3.56 (s, 3H, OCH$_3$) 3.86 (s, 3H, OCH$_3$) 5.84 (s, 1H, ArH) 6.87 (s, 1H, ArH) 7.99-8.04 (m, 2H, ArH) 8.13-8.18 (m, 2H, ArH).

Example 107

N-[2-(4-Amino-2-hydroxy-1,3-dioxo-indan-2-yl)-4,5-dimethoxy-phenyl]-isobutyramide N-[2-(2-hydroxy-4-nitro-1,3-dioxo-indan-2-yl)-4,5-dimethoxy-phenyl]-isobutyramide (150 mg, 0.35 mmol) was dissolved in ethanol (3 ml) and water (0.3 ml). This solution was added with iron (Fe) (0.14 g, 2.55 mmol) and conc. HCl (0.03 ml), followed by heating for 3 hrs under reflux. The reaction mixture was filtrated with MeOH washing via celite pad, and the filtrate was concentrated in a vaccume. The concentrated organic layer was purified using column chromatography (ethylacetate:hexane=1:4) to afford the title compound (17 mg, 12%).

$^1$H-NMR (300 MHz, CDCl$_3$) δ 0.77 (d, J=6.9 Hz, 3H, CH$_3$) 1.19 (d, J=6.9 Hz, 3H, CH$_3$) 2.01-2.10 (m, 1H, CH), 3.91 (s, 3H, OMe) 4.07 (s, 3H, OMe) 5.36 (s, 2H, NH$_2$) 6.49 (d, J=7.2 Hz, 1H, ArH) 6.74 (d, J=8.1 Hz, 1H, ArH) 7.15 (s, 1H, ArH) 7.37 (t, J=7.5 Hz, 1H, ArH) 8.35 (s, 1H, ArH).

Example 108

N-[2-(2-Hydroxy-5,6-dimethoxy-1,3-dioxo-indan-2-yl)-4,5-dimethoxy-phenyl]-isobutyramide 5,6-dimethoxy-indan-1-one (3.0 g, 15.6 mmol) was dissolved in anhydrous dioxane (30 ml). This solution was added with SeO2 (3.80 g, 34.3 mmol) and acetic acid (3 ml), followed by heating for 5 hrs under reflux. The reaction mixture was filtrated with MeOH washing via celite pad, and the filtrate was concentrated in a vaccume to remove solvent. The remainder (2.13 g, 8.95 mmol) was dissolved in conc.H2SO4 (20 ml), and added with isobutyramide (3.50 g, 15.6 mmol), followed by stirring for 2 hrs under room temperature. After stirring, the reaction mixture was washed with ethylacetate and water in several times. The obtained organic layer was dried, filtrated and concentrated in a vaccume. The concentrated organic layer was purified using column chromatography (ethylacetate:hexane=1:4) to afford the title compound (218 mg, 3%).

$^1$H-NMR (300 MHz, CDCl$_3$) δ 1.36 (d, J=6.6 Hz, 6H, CH$_3$) 2.67-2.76 (m, 1H, CH) 3.63 (s, 3H, OMe) 3.85 (s, 3H, OMe) 4.06 (s, 6H, OMe) 6.24 (s, 1H, ArH) 7.15 (s, 1H, ArH) 7.99 (s, 1H, ArH) 9.70 (s, 1H, ArH).

In Table 1, chemical formulas of compounds of examples 1 to 108 are shown.

TABLE 1

| Ex. | Chemical structure |
|---|---|
| 1 | 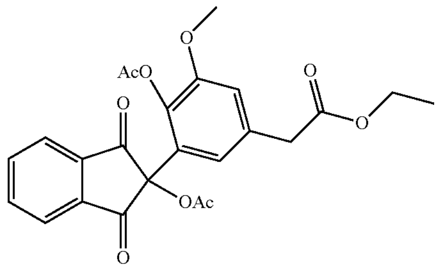 [SMILES: CCOC(=O)Cc1cc(OC)c(OC(C)=O)c(C2(OC(C)=O)C(=O)c3ccccc3C2=O)c1] |
| 2 | 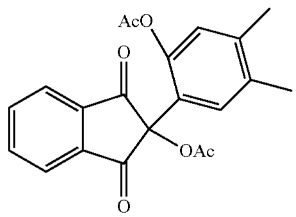 [SMILES: CC(=O)Oc1cc(C)c(C)cc1C1(OC(C)=O)C(=O)c2ccccc2C1=O] |
| 3 | 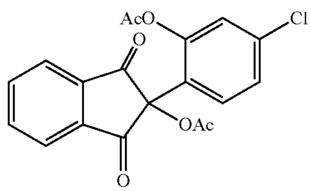 [SMILES: CC(=O)Oc1cc(Cl)ccc1C1(OC(C)=O)C(=O)c2ccccc2C1=O] |
| 4 | 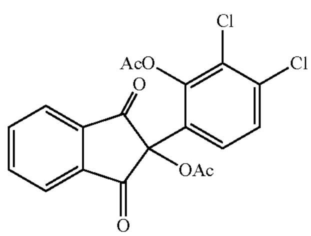 [SMILES: CC(=O)Oc1c(C2(OC(C)=O)C(=O)c3ccccc3C2=O)ccc(Cl)c1Cl] |
| 5 | 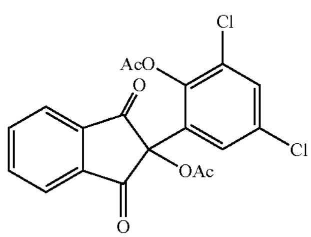 [SMILES: CC(=O)Oc1c(Cl)cc(Cl)cc1C1(OC(C)=O)C(=O)c2ccccc2C1=O] |
| 6 | 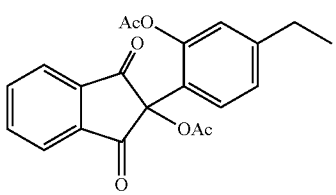 [SMILES: CCc1ccc(C2(OC(C)=O)C(=O)c3ccccc3C2=O)c(OC(C)=O)c1] |
| 7 | 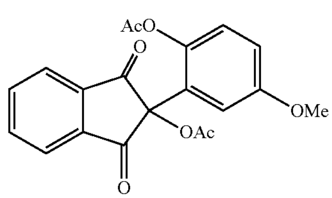 [SMILES: COc1ccc(OC(C)=O)c(C2(OC(C)=O)C(=O)c3ccccc3C2=O)c1] |

TABLE 1-continued

| Ex. | Chemical structure |
|---|---|
| 8 | 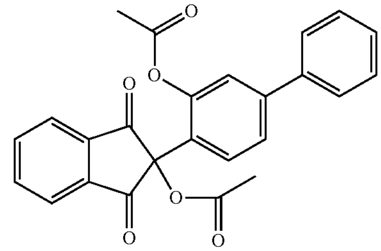 [SMILES: CC(=O)Oc1cc(-c2ccccc2)ccc1C1(OC(C)=O)C(=O)c2ccccc2C1=O] |
| 9 | 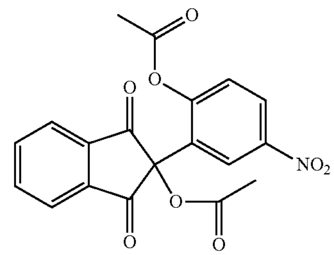 [SMILES: CC(=O)Oc1ccc([N+](=O)[O-])cc1C1(OC(C)=O)C(=O)c2ccccc2C1=O] |
| 10 | 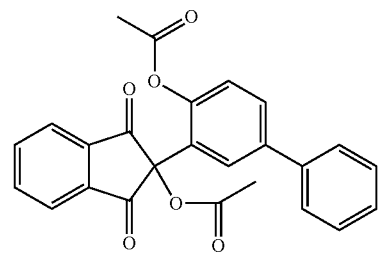 [SMILES: CC(=O)Oc1ccc(-c2ccccc2)cc1C1(OC(C)=O)C(=O)c2ccccc2C1=O] |
| 11 | 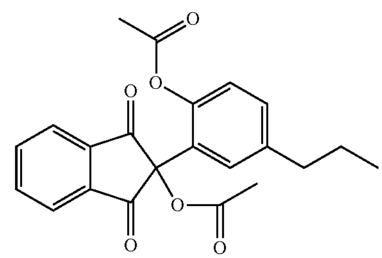 [SMILES: CCCc1ccc(OC(C)=O)c(C2(OC(C)=O)C(=O)c3ccccc3C2=O)c1] |
| 12 | 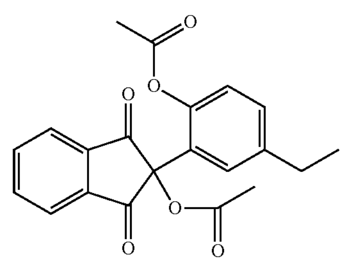 [SMILES: CCc1ccc(OC(C)=O)c(C2(OC(C)=O)C(=O)c3ccccc3C2=O)c1] |
| 13 | 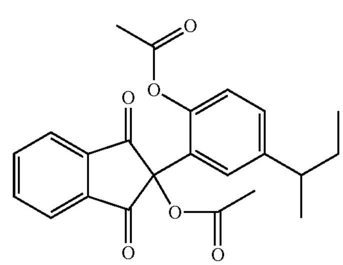 [SMILES: CCC(C)c1ccc(OC(C)=O)c(C2(OC(C)=O)C(=O)c3ccccc3C2=O)c1] |

TABLE 1-continued

| Ex. | Chemical structure |
|---|---|
| 14 | 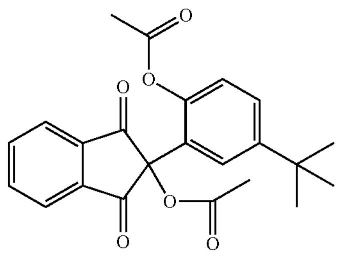 [SMILES: CC(=O)Oc1ccc(C(C)(C)C)cc1C1(OC(C)=O)C(=O)c2ccccc2C1=O] |
| 15 | 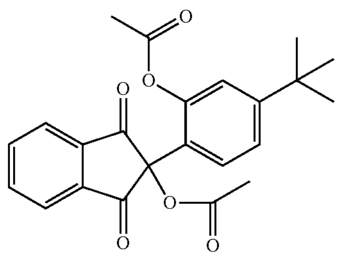 [SMILES: CC(=O)Oc1cc(C(C)(C)C)ccc1C1(OC(C)=O)C(=O)c2ccccc2C1=O] |
| 16 | 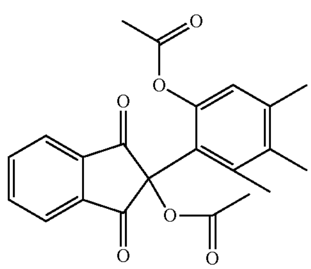 [SMILES: CC(=O)Oc1cc(C)c(C)c(C)c1C1(OC(C)=O)C(=O)c2ccccc2C1=O] |
| 17 | 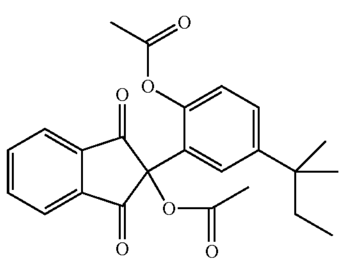 [SMILES: CCC(C)(C)c1ccc(OC(C)=O)c(C2(OC(C)=O)C(=O)c3ccccc3C2=O)c1] |
| 18 | 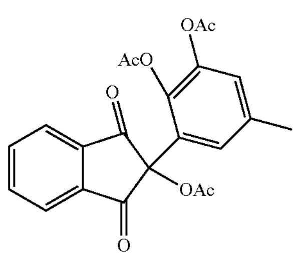 [SMILES: CC(=O)Oc1cc(C)cc(C2(OC(C)=O)C(=O)c3ccccc3C2=O)c1OC(C)=O] |
| 19 | 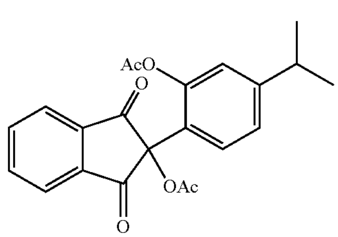 [SMILES: CC(=O)Oc1cc(C(C)C)ccc1C1(OC(C)=O)C(=O)c2ccccc2C1=O] |
| 20 | |
| 21 | |
| 22 | |
| 23 | |
| 24 | |

TABLE 1-continued
| Ex. | Chemical structure |
|---|---|
| 25 | 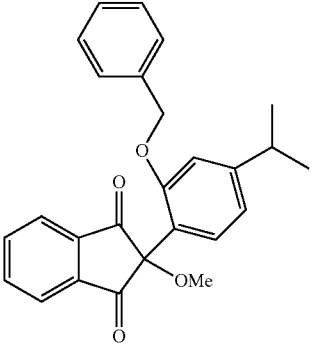 [SMILES: COC1(c2ccc(C(C)C)cc2OCc2ccccc2)C(=O)c2ccccc2C1=O] |
| 26 | 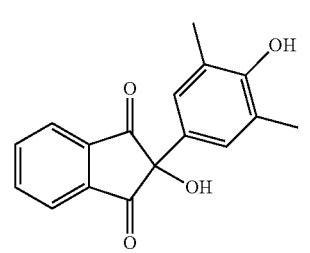 [SMILES: Cc1cc(C2(O)C(=O)c3ccccc3C2=O)cc(C)c1O] |
| 27 | 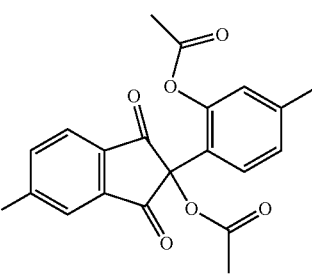 |
| 28 | 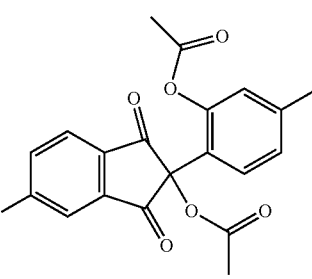 |
| 29 | 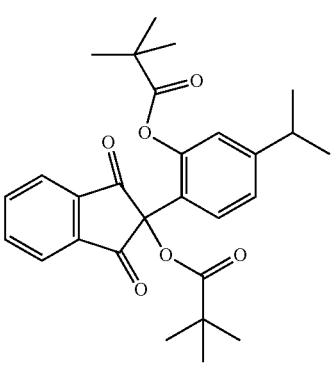 [SMILES: CC(C)c1ccc(C2(OC(=O)C(C)(C)C)C(=O)c3ccccc3C2=O)c(OC(=O)C(C)(C)C)c1] |
TABLE 1-continued
| Ex. | Chemical structure |
|---|---|
| 30 | 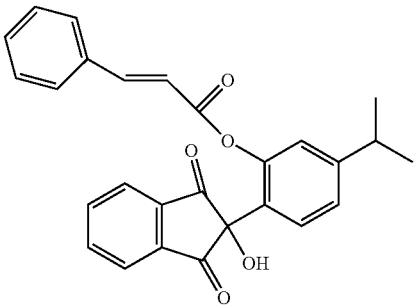 [SMILES: CC(C)c1ccc(C2(O)C(=O)c3ccccc3C2=O)c(OC(=O)/C=C/c2ccccc2)c1] |
| 31 | 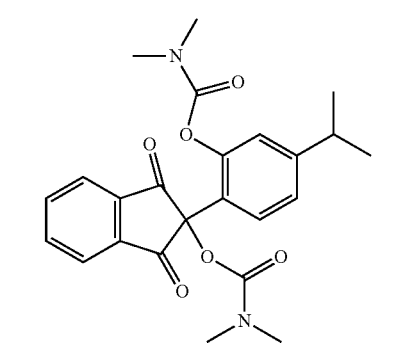 [SMILES: CC(C)c1ccc(C2(OC(=O)N(C)C)C(=O)c3ccccc3C2=O)c(OC(=O)N(C)C)c1] |
| 32 | 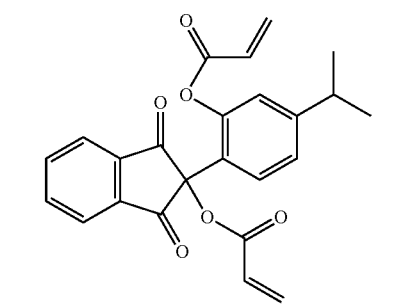 [SMILES: C=CC(=O)Oc1cc(C(C)C)ccc1C1(OC(=O)C=C)C(=O)c2ccccc2C1=O] |
| 33 | 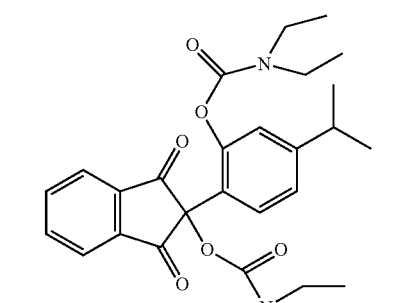 |
| 34 | 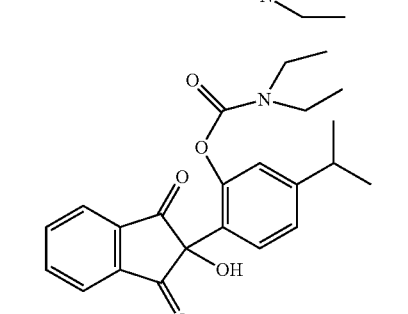 |

TABLE 1-continued

| Ex. | Chemical structure |
|---|---|
| 35 | 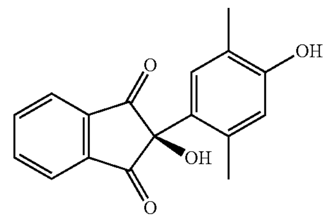 |
| 36 | 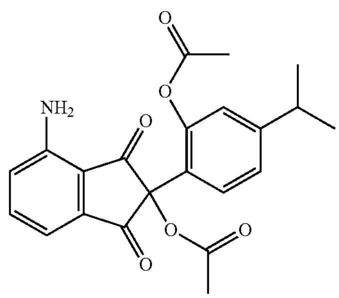 [SMILES: CC(=O)Oc1cc(C(C)C)ccc1C1(OC(C)=O)C(=O)c2cccc(N)c2C1=O] |
| 37 | 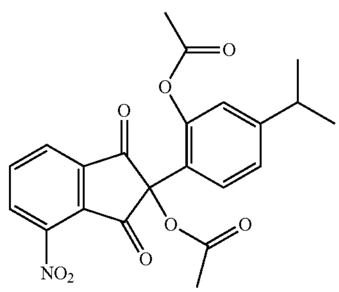 [SMILES: CC(=O)Oc1cc(C(C)C)ccc1C1(OC(C)=O)C(=O)c2cccc([N+](=O)[O-])c2C1=O] |
| 38 | 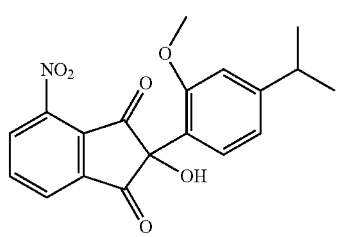 [SMILES: COc1cc(C(C)C)ccc1C1(O)C(=O)c2cccc([N+](=O)[O-])c2C1=O] |
| 39 | 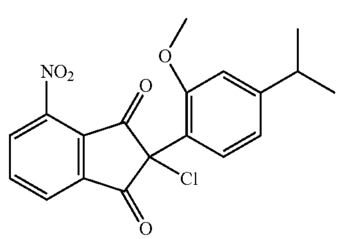 [SMILES: COc1cc(C(C)C)ccc1C1(Cl)C(=O)c2cccc([N+](=O)[O-])c2C1=O] |
| 40 | 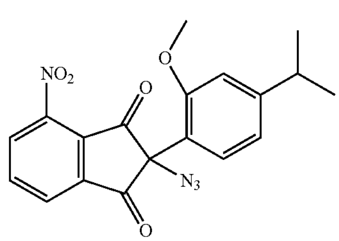 [SMILES: COc1cc(C(C)C)ccc1C1(N=[N+]=[N-])C(=O)c2cccc([N+](=O)[O-])c2C1=O] |
| 41 | |
| 42 | |
| 43 | |
| 44 | |
| 45 | |

TABLE 1-continued

| Ex. | Chemical structure |
|---|---|
| 46 | |
| 47 | |
| 48 | |
| 49 | |
| 50 | |
| 51 | 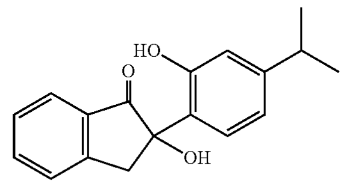 [SMILES: CC(C)c1ccc(C2(O)Cc3ccccc3C2=O)c(O)c1] |
| 52 | 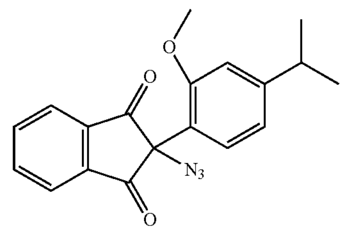 [SMILES: COc1cc(C(C)C)ccc1C1(N=[N+]=[N-])C(=O)c2ccccc2C1=O] |
| 53 | 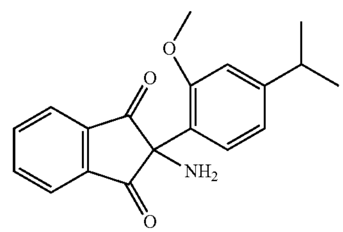 [SMILES: COc1cc(C(C)C)ccc1C1(N)C(=O)c2ccccc2C1=O] |
| 54 | 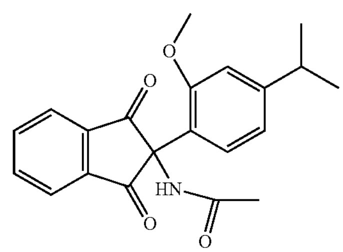 [SMILES: COc1cc(C(C)C)ccc1C1(NC(C)=O)C(=O)c2ccccc2C1=O] |
| 55 | 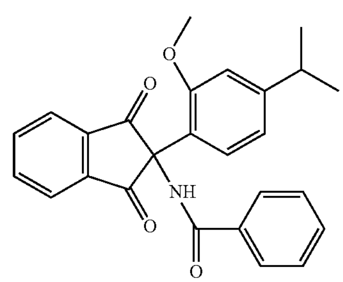 [SMILES: COc1cc(C(C)C)ccc1C1(NC(=O)c2ccccc2)C(=O)c2ccccc2C1=O] |
| 56 | 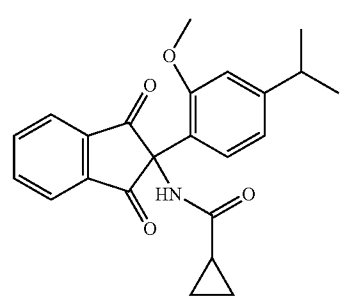 [SMILES: COc1cc(C(C)C)ccc1C1(NC(=O)C2CC2)C(=O)c2ccccc2C1=O] |

TABLE 1-continued

| Ex. | Chemical structure |
|---|---|
| 57 | 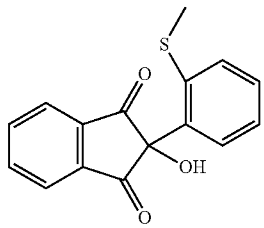 [SMILES: CSc1ccccc1C1(O)C(=O)c2ccccc2C1=O] |
| 58 | 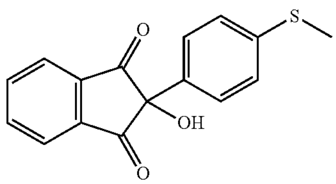 [SMILES: CSc1ccc(C2(O)C(=O)c3ccccc3C2=O)cc1] |
| 59 | 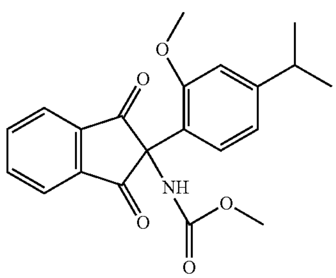 [SMILES: COC(=O)NC1(c2ccc(C(C)C)cc2OC)C(=O)c2ccccc2C1=O] |
| 60 | 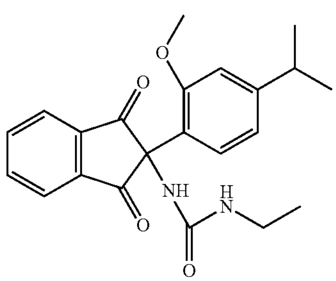 [SMILES: CCNC(=O)NC1(c2ccc(C(C)C)cc2OC)C(=O)c2ccccc2C1=O] |
| 61 | 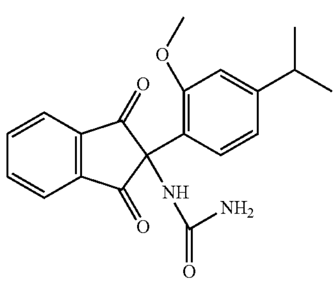 [SMILES: COc1cc(C(C)C)ccc1C1(NC(N)=O)C(=O)c2ccccc2C1=O] |
| 62 | 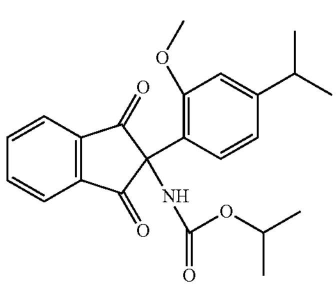 [SMILES: COc1cc(C(C)C)ccc1C1(NC(=O)OC(C)C)C(=O)c2ccccc2C1=O] |

TABLE 1-continued

| Ex. | Chemical structure |
|---|---|
| 63 | 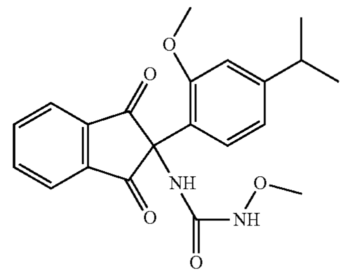 [SMILES: CONC(=O)NC1(c2ccc(C(C)C)cc2OC)C(=O)c2ccccc2C1=O] |
| 64 | 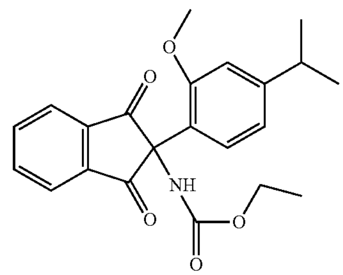 [SMILES: CCOC(=O)NC1(c2ccc(C(C)C)cc2OC)C(=O)c2ccccc2C1=O] |
| 65 | 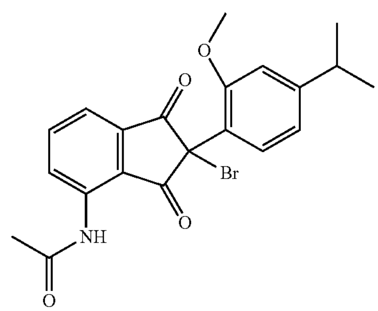 [SMILES: COc1cc(C(C)C)ccc1C1(Br)C(=O)c2cccc(NC(C)=O)c2C1=O] |
| 66 | 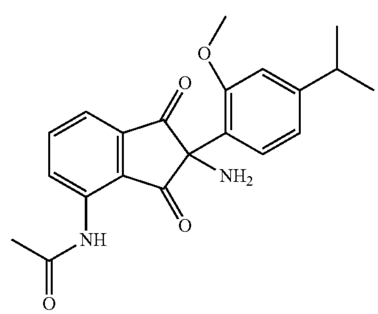 [SMILES: COc1cc(C(C)C)ccc1C1(N)C(=O)c2cccc(NC(C)=O)c2C1=O] |
| 67 | 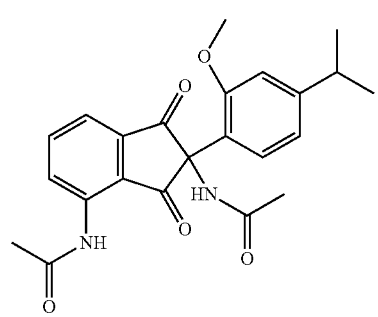 [SMILES: COc1cc(C(C)C)ccc1C1(NC(C)=O)C(=O)c2cccc(NC(C)=O)c2C1=O] |

TABLE 1-continued
| Ex. | Chemical structure |
|---|---|
| 68 | 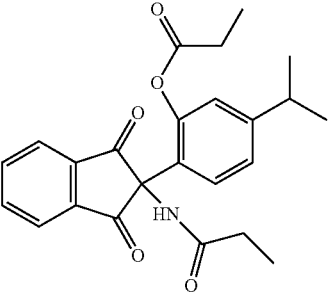 [SMILES: CCC(=O)NC1(c2ccc(C(C)C)cc2OC(=O)CC)C(=O)c2ccccc2C1=O] |
| 69 | 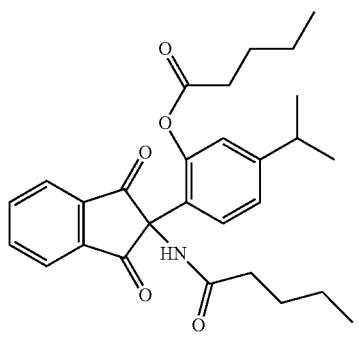 [SMILES: CCCCC(=O)NC1(c2ccc(C(C)C)cc2OC(=O)CCCC)C(=O)c2ccccc2C1=O] |
| 70 | 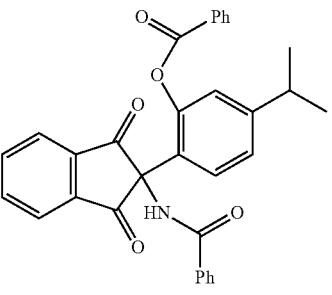 [SMILES: CC(C)c1ccc(C2(NC(=O)c3ccccc3)C(=O)c3ccccc3C2=O)c(OC(=O)c2ccccc2)c1] |
| 71 | 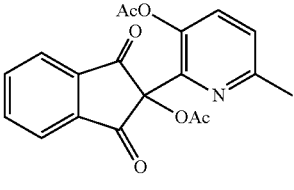 [SMILES: CC(=O)Oc1ccc(C)nc1C1(OC(C)=O)C(=O)c2ccccc2C1=O] |
| 72 | 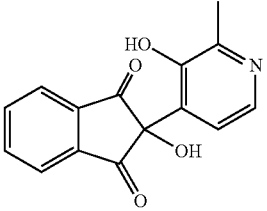 [SMILES: Cc1nccc(C2(O)C(=O)c3ccccc3C2=O)c1O] |
| 73 | 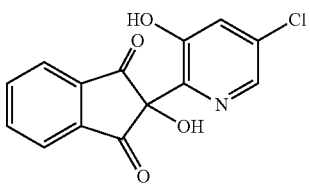 [SMILES: O=C1c2ccccc2C(=O)C1(O)c1ncc(Cl)cc1O] |
| 74 | 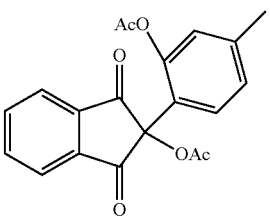 [SMILES: CC(=O)Oc1cc(C)ccc1C1(OC(C)=O)C(=O)c2ccccc2C1=O] |
| 75 | 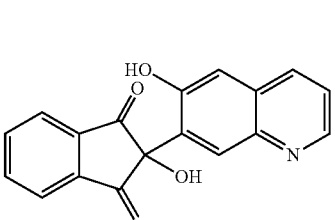 |
| 76 | 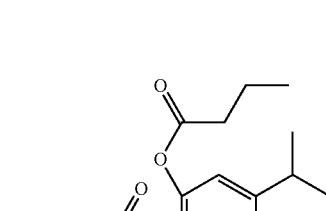 |
| 77 | 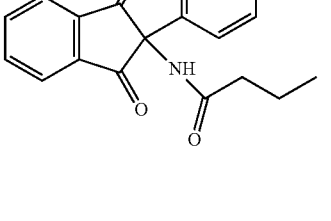 |
| 78 | 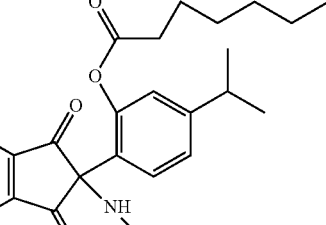 |

TABLE 1-continued
| Ex. | Chemical structure |
|---|---|
| 79 | 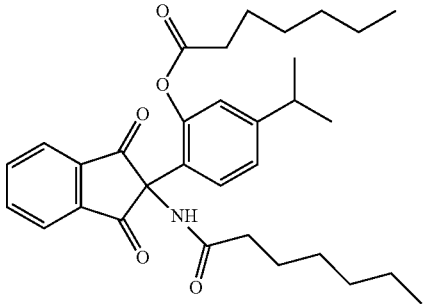 [SMILES: CCCCCCC(=O)NC1(c2ccc(C(C)C)cc2OC(=O)CCCCCC)C(=O)c2ccccc2C1=O] |
| 80 | 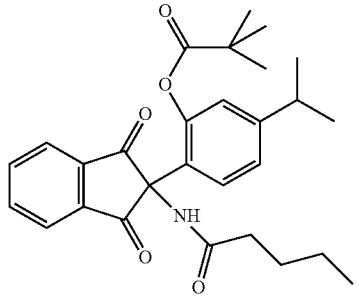 [SMILES: CCCCC(=O)NC1(c2ccc(C(C)C)cc2OC(=O)C(C)(C)C)C(=O)c2ccccc2C1=O] |
| 81 | 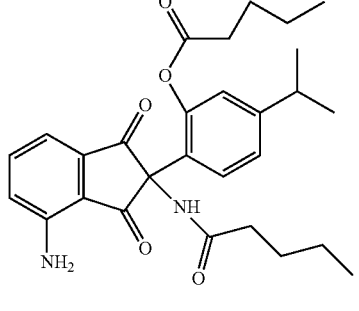 |
| 82 | 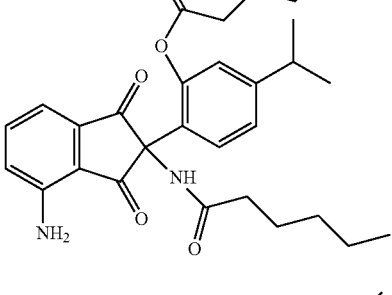 |
| 83 | 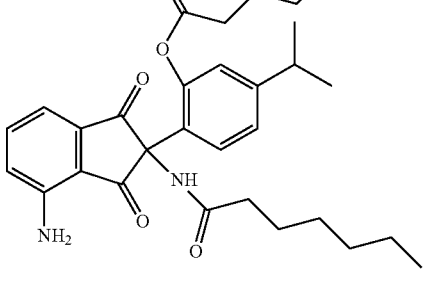 |
TABLE 1-continued
| Ex. | Chemical structure |
|---|---|
| 84 | 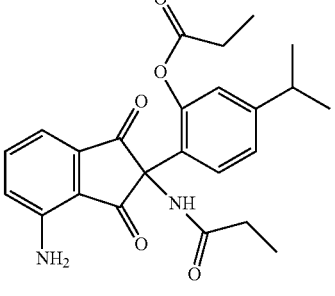 |
| 85 | 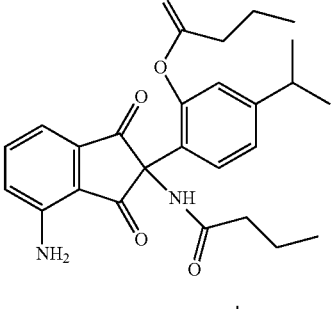 |
| 86 | 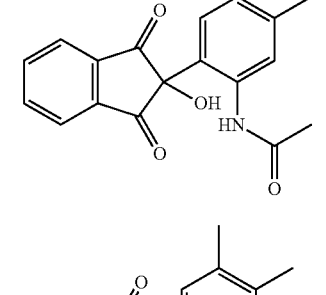 |
| 87 | 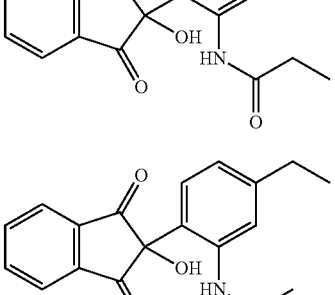 |
| 88 | 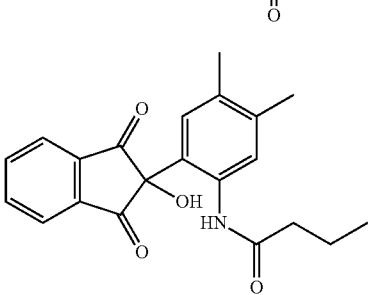 |
| 89 | 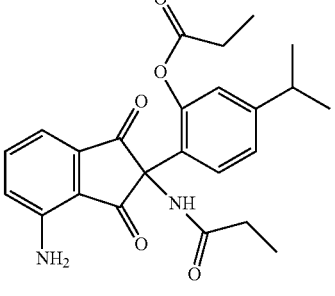 |

TABLE 1-continued

| Ex. | Chemical structure |
|---|---|
| 90 | 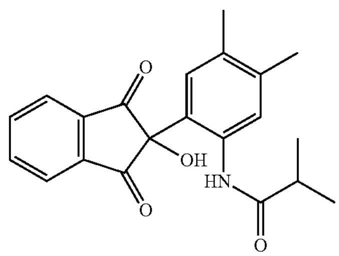 [SMILES: Cc1cc(NC(=O)C(C)C)c(C2(O)C(=O)c3ccccc3C2=O)cc1C] |
| 91 | 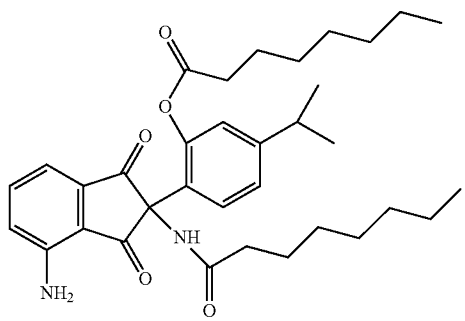 [SMILES: CCCCCCCC(=O)NC1(c2ccc(C(C)C)cc2OC(=O)CCCCCCC)C(=O)c2cccc(N)c2C1=O] |
| 92 | 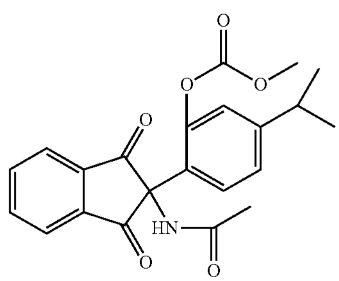 [SMILES: COC(=O)Oc1cc(C(C)C)ccc1C1(NC(C)=O)C(=O)c2ccccc2C1=O] |
| 93 | 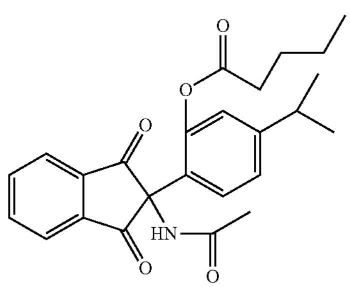 [SMILES: CCCCC(=O)Oc1cc(C(C)C)ccc1C1(NC(C)=O)C(=O)c2ccccc2C1=O] |
| 94 | 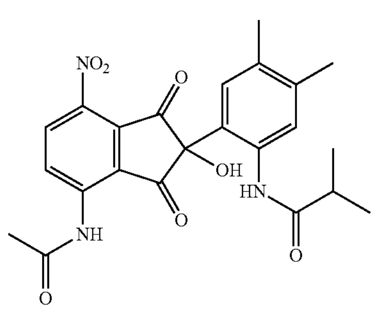 [SMILES: CC(=O)Nc1ccc([N+](=O)[O-])c2c1C(=O)C(O)(c1cc(C)c(C)cc1NC(=O)C(C)C)C2=O] |

TABLE 1-continued

| Ex. | Chemical structure |
|---|---|
| 95 | 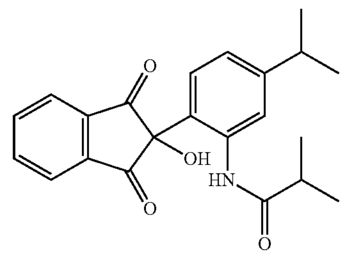 [SMILES: CC(C)C(=O)Nc1cc(C(C)C)ccc1C1(O)C(=O)c2ccccc2C1=O] |
| 96 | 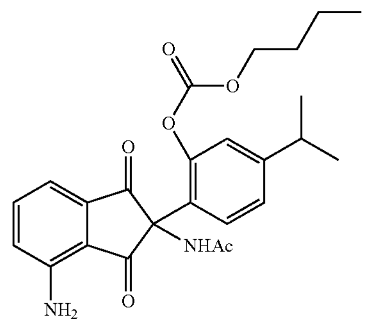 [SMILES: CCCCOC(=O)Oc1cc(C(C)C)ccc1C1(NC(C)=O)C(=O)c2cccc(N)c2C1=O] |
| 97 | 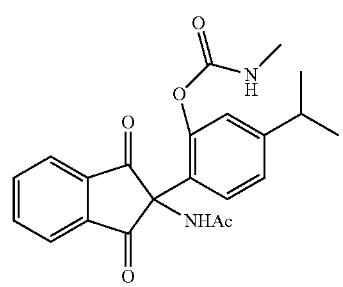 [SMILES: CNC(=O)Oc1cc(C(C)C)ccc1C1(NC(C)=O)C(=O)c2ccccc2C1=O] |
| 98 | 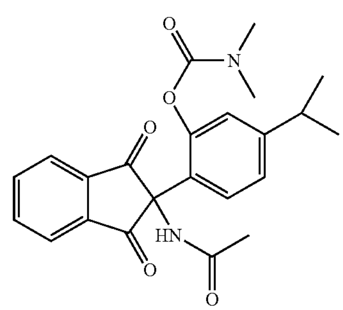 [SMILES: CC(=O)NC1(c2ccc(C(C)C)cc2OC(=O)N(C)C)C(=O)c2ccccc2C1=O] |
| 99 | 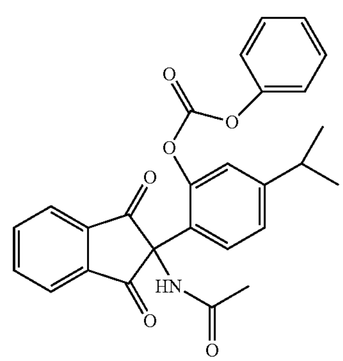 [SMILES: CC(=O)NC1(c2ccc(C(C)C)cc2OC(=O)Oc2ccccc2)C(=O)c2ccccc2C1=O] |

TABLE 1-continued

| Ex. | Chemical structure |
|---|---|
| 100 | (structure) |
| 101 | (structure) |
| 102 | (structure) |
| 103 | (structure) |
| 104 | (structure) |
| 105 | (structure) |
| 106 | (structure) |
| 107 | (structure) |
| 108 | (structure) |

Experimental Example 1

Cytopathic Effect (CPE) Inhibition Assay for Antiviral Activity Against Picornaviruses In the assay, HeLa (human cervical cancer cells), MRC-5 (human fetal lung fibroblast cells), and RD cells (derived from human rhabdomyosarcoma) were employed. For comparison, ribavirin (Riv), pleconaril (pleco), and BTA-798 (BTA) were used as controls. Reagents were dissolved at a concentration of 10-40 mg/ml in 100% dimethylsulfoxide (DMSO). Water-soluble reagents were dissolved in PBS (−) solution and stored at −20° C. On the day of the experiment, they were used in 3× to 5× concentrations in such a manner that the concentration of dimethylsulfoxide in each well was between 0.5% and 1%.

Pharmaceutical effects were determined using a virus-induced cytopathic effect (CPE) inhibition assay. In this regard, after cells suitable for viruses were grown in 96-well plates, dilutions of viruses in DME supplemented with 2% FBS (DME/2% FBS) or MEM supplemented with 2% FBS (MEM/2% FBS) were inoculated in an amount of 100 µl with a concentration corresponding to 100 $CCID_{50}$ (50% cell culture infective dose) into each well of the plates, and incubated for 30 min~1 hrs at 33° C. or 37° C. to allow the viruses to adosorb to the cells. The culture medium was removed before aliquots of drug dilutions with various concentrations were added in an amount of 100 µl to each well. While HRV was grown at 33° C., the other viruses were incubated in a 37° C. $CO_2$ incubator for 2~3 days. Alternatively, the cells were cultured for 2~3 days without removal of the medium after they were added with 50 µl of each drug dilution having a 2-fold higher concentration and then with 50 µl of the virus dilution.

Test conditions for each virus are summarized in Table 2, below.

TABLE 2

| Virus | Note | Host cell | Incubation Temp. | Incubation Term | Medium |
|---|---|---|---|---|---|
| Coxsackie A9 | — | RD | 37° C. | 2 days | MEM/2% FBS |
| Coxsackie A24 | — | MRC-5 | 37° C. | 2 days | MEM/2% FBS |
| Coxsackie A24 | Isolated from patients | MRC-5 | 37° C. | 2 days | MEM/2% FBS |
| Coxsackie B1 | — | HeLa | 37° C. | 2 days | DME/2% FBS |
| Coxsackie B3 | — | HeLa | 37° C. | 2 days | DME/2% FBS |
| Coxsackie B4 | — | HeLa | 37° C. | 2 days | DME/2% FBS |
| Entero 70 | — | MRC-5 | 37° C. | 2 days | MEM/2% FBS |
| Poliovirus3 | — | HeLa | 37° C. | 2 days | DME/2% FBS |
| Rhinovirus | — | HeLa | 33° C. | 3 days | MEM/2% FBS |

For HeLa cells, the drugs were measured for $EC_{50}$ (50% maximal effective concentration), which is the concentration of a drug inducing a response halfway between the baseline and maximun, using an MTT assay. With regard to RD and MRC-5 cells, CPE was determined using FDA (Fluorescein diacetate). In order for the evaluation results of drug potency to reflect the toxic effect of the drug, mock-infected cells which were prepared by adding a virus-free medium to a cell culture were treated in the same manner. That is, the medium was removed after one hour of incubation, and dilutions of drugs in the medium were added once more. Following incubation for 2~3 days, the cells were observed under a microscope and the drugs were determined for $CC_{50}$ (50% cytotoxic concentration), using an MTT assay in which counts of viable cells in mock-infected wells containing drugs were compared to those of viable cells in control wells containing no drugs. In an FDA hydrolysis assay, FDA was added to each well after removal of the medium, and incubated for 20~30 min before fluorescence intensity was measured using a spectrofluorometer to determine CPE in the same manner as in MTT.

Survival rate (% survival) of mock-infected cells was calculated using the following Mathmatic Formula 1:

$$\text{Cell Survival by Drug} = \frac{A(\text{Drug}) - A(\text{Background } Sol'n)}{A(\text{Cell Control}) - A(Bakground\ Sol'n)} \times 100\%$$  [Mathmatic Formula 1]

While 100% cell survival means no cytotoxicity of the drug, the highest cytotoxicity is reflected by 0% cell survival. The 50% cytotoxic concentration ($CC_{50}$) was defined as the concentration required to reduce the cell number by 50% compared to that for the untreated controls. Higher $CC_{50}$ values mean lower cytotoxicity.

In addition, antiviral effects can be calculated using the following Mathmatic Formula 2:

$$\text{Antiviral Effect} = \frac{A(\text{Drug/Virus}) - A(\text{Virus Control})}{A(\text{Cell Control}) - A(\text{Virus Control})} \times 100\%$$  [Mathmatic Formula 2]

A survaival rate of 100% means a perfect antiviral effect (100%) whereas the drugs are regarded to be devoid of antiviral effects at a survival rate of 0%. The viral cytopathic effect (CPE) was recorded, and the 50% effective concentration ($EC_{50}$) was defined as the compound concentration required to reduce the viral CPE by 50% compared to that for the untreated control. Lower $EC_{50}$ values mean higher antiviral activities.

$CC_{50}$ and $EC_{50}$ values of the compounds which accout cytotoxicity and antivival activity against picornaviruses, respectively, are given in Tables 3 and 4.

TABLE 3

| | | $EC_{50}$ (µg/mL) | | | | | | | |
|---|---|---|---|---|---|---|---|---|---|
| Ex. No. | $CC_{50}$ (µg/mL) | Coxsackie-virus B1 | Coxsackie-virus B3 | Coxsackie-virus B4 | Coxsackie-virus A24(DN) | Coxsackie-virus A24(HG) | Polio-virus 3 | Polio-virus 2 | Entero-virus 70 |
| 1 | >100 | — | — | — | — | — | — | — | — |
| 2 | >100 | — | — | — | — | — | — | — | <1.0 |
| 3 | 50.7 | — | — | — | — | — | — | — | 0.013 |
| 4 | 50.4 | — | — | — | — | — | — | — | — |
| 5 | 26 | — | — | — | — | — | — | — | — |
| 6 | 23.5 | <0.01 | 0.035 | — | — | — | — | — | <0.01 |
| 7 | >100 | — | — | — | — | — | — | — | — |
| 8 | 7.91 | — | — | — | — | — | — | — | — |
| 9 | >100 | — | — | — | — | — | — | — | — |
| 10 | 7.85 | — | — | — | — | — | — | — | — |

TABLE 3-continued

| | | EC$_{50}$ (µg/mL) | | | | | | | |
|---|---|---|---|---|---|---|---|---|---|
| Ex. No. | CC$_{50}$ (µg/mL) | Coxsackie-virus B1 | Coxsackie-virus B3 | Coxsackie-virus B4 | Coxsackie-virus A24(DN) | Coxsackie-virus A24(HG) | Polio-virus 3 | Polio-virus 2 | Entero-virus 70 |
| 11 | 8.42 | — | — | — | — | — | — | — | — |
| 12 | 74.12 | — | — | — | — | — | — | — | — |
| 13 | 7.93 | — | — | — | — | — | — | — | — |
| 14 | 8.26 | — | — | — | — | — | — | — | — |
| 15 | 8.26 | 0.015 | — | — | — | — | — | — | — |
| 16 | 8.87 | — | — | — | — | — | — | — | — |
| 17 | 9.3 | — | — | — | — | — | — | — | — |
| 18 | >100 | — | — | — | — | — | — | — | — |
| 19 | 17.7 | <0.01 | <0.01 | — | — | <1.0 | <1.0 | — | <0.01 |
| 20 | >100 | — | — | — | — | — | — | — | — |
| 21 | 16 | <0.01 | — | — | — | — | — | — | — |
| 22 | 33.8 | <0.01 | — | — | — | — | — | — | — |
| 23 | 44.3 | <0.01 | — | — | — | — | — | — | — |
| 24 | >100 | — | — | — | — | — | — | — | — |
| 25 | >100 | — | — | — | — | — | — | — | — |
| 26 | >100 | — | — | — | — | — | — | — | — |
| 27 | 9.5 | — | — | — | — | — | — | — | — |
| 28 | 9.2 | — | — | — | — | — | — | — | — |
| 29 | >100 | — | — | — | — | — | — | — | — |
| 30 | >100 | <0.01 | — | — | — | — | — | — | — |
| 31 | >100 | — | — | — | — | — | — | — | — |
| 32 | 28.69 | <0.01 | — | — | — | — | — | — | — |
| 33 | >100 | — | — | — | — | — | — | — | — |
| 34 | 46.25 | — | — | — | — | — | — | — | — |
| 35 | 59.8 | — | — | — | — | — | — | — | — |
| 36 | 9.42 | <0.01 | <0.01 | — | <0.1 | <0.01 | <0.01 | — | — |
| 37 | 62.72 | — | — | — | — | — | — | — | — |
| 38 | >100 | — | — | — | — | — | — | — | — |
| 39 | 6.67 | — | — | — | — | — | — | — | — |
| 40 | 53.25 | — | — | — | — | — | — | — | — |
| 41 | — | — | — | — | — | — | — | — | — |
| 42 | 71.06 | — | — | — | — | — | — | — | — |
| 43 | 61.7 | — | — | — | — | — | — | — | — |
| 44 | >117 | — | — | — | — | — | — | — | — |
| 45 | >117 | — | — | — | — | — | — | — | — |
| 46 | 63.98 | — | — | — | — | — | — | — | — |
| 47 | 50.92 | — | — | — | — | — | — | — | — |
| 48 | 46.74 | <0.01 | <0.01 | — | — | — | — | — | — |
| 49 | >100 | <0.01 | <0.01 | <0.01 | <1.0 | <1.0 | <1.0 | <1.0 | — |
| 50 | 44.32 | 0.0112 | — | — | — | — | — | — | — |
| 51 | 9.34 | — | — | — | — | — | — | — | — |
| 52 | 27.67 | — | — | — | — | — | — | — | — |
| 53 | 10.2 | — | — | — | — | — | — | — | — |
| 54 | >117 | 0.0198 | — | — | — | — | — | — | — |
| 55 | >117 | — | — | — | — | — | — | — | — |
| 56 | 87.77 | — | — | — | — | — | — | — | — |
| 57 | 48.21 | — | — | — | — | — | — | — | — |
| 58 | 47.79 | — | — | — | — | — | — | — | — |
| 59 | 53.67 | — | — | — | — | — | — | — | — |
| 60 | 68.93 | — | — | — | — | — | — | — | — |
| 61 | >117 | — | — | — | — | — | — | — | — |
| 62 | 11.26 | — | — | — | — | — | — | — | — |
| 63 | >117 | — | — | — | — | — | — | — | — |
| 64 | 87.77 | — | — | — | — | — | — | — | — |
| 65 | 11.16 | — | — | — | — | — | — | — | — |
| 66 | 26.69 | — | — | — | — | — | — | — | — |
| 67 | 54.59 | — | — | — | — | — | — | — | — |
| 68 | 65.95 | <0.01 | <0.01 | — | — | <1.0 | — | — | — |
| 69 | >117 | <0.01 | <0.01 | — | <1.0 | <1.0 | <1.0 | — | — |
| 70 | >117 | <0.01 | <0.01 | — | — | <1.0 | — | — | — |
| 71 | >100 | — | — | — | — | — | — | — | — |
| 72 | >100 | — | — | — | — | — | — | — | — |
| 73 | >100 | — | — | — | — | — | — | — | — |
| 74 | — | — | — | — | — | — | — | — | — |
| 75 | >100 | — | — | — | — | — | — | — | — |

TABLE 4

| Ex. No. | Picorna-virus $CC_{50}$ (μg/mL) | Coxsackie-virus B1 $EC_{50}$ (μg/mL) | Coxsackie-virus B3 $EC_{50}$ (μg/mL) | Polio-virus 3 $EC_{50}$ (μg/mL) |
|---|---|---|---|---|
| 76 | 45.11 | <0.01 | <0.04 | — |
| 77 | 77.77 | 0.014 | 0.018 | — |
| 78 | 68.17 | <0.01 | <0.01 | — |
| 79 | 8.94 | <0.01 | <0.01 | — |
| 80 | >100 | <0.01 | <0.01 | — |
| 81 | 41.26 | <0.01 | <0.01 | 0.012 |
| 82 | >100 | <0.01 | <0.02 | 0.015 |
| 83 | >100 | <0.01 | <0.01 | — |
| 84 | >100 | <0.01 | <0.01 | — |
| 85 | 45.85 | <0.01 | <0.03 | 0.015 |
| 86 | 4.63 | — | — | — |
| 87 | 8.31 | 0.019 | — | — |
| 88 | 4.49 | — | — | — |
| 89 | 10.7 | — | — | — |
| 90 | 38.26 | — | — | — |
| 91 | 40.02 | 0.015 | — | — |
| 92 | 43.58 | <0.01 | <0.01 | — |
| 93 | 35.21 | <0.01 | <0.01 | — |
| 94 | 39.17 | <0.01 | <0.01 | — |
| 95 | 27.45 | <0.01 | <0.01 | — |
| 96 | 48.85 | <0.01 | <0.01 | 0.03 |
| 97 | 45.09 | <0.01 | <0.01 | — |
| 98 | >100 | 0.013 | — | — |
| 99 | 38.07 | <0.01 | <0.01 | — |
| 100 | >100 | <0.01 | <0.01 | — |
| 101 | 45.95 | <0.01 | <0.01 | — |
| 102 | 42.5 | <0.01 | <0.01 | — |
| 103 | 26.27 | <0.01 | <0.01 | 0.013 |
| 104 | >100 | — | — | — |
| 105 | >100 | — | — | — |
| 106 | >100 | — | — | — |
| 107 | >100 | — | — | — |
| 108 | >100 | — | — | — |

As is understood from data of Tables 3 and 4, most of the 1,3-Dioxoindene derivatives of the present invention exhibited low cytotoxicity because they had high $CC_{50}$ values. In addition, most of the 1,3-Dioxoindene derivatives of the present invention were found to be highly inhibitory of coxsackie-, polio-, rhino-, and entero-viruses because their $EC_{50}$ values were 0.01 μg/mL or less.

Accordingly, the 1,3-Dioxoindene derivatives represented by Chemcial Formula 1 in accordance with the present invention exhibit low cytotoxicity and high inhibitory activity against a broad spectrum of picornaviruses, and thus may be usefully applied to a pharmaceutical composition for preventing or treating picornavirus-caused diseases.

Experimental Example 2

Multicycle Cytopathic Effect (CPE) Reduction Assay for Antiviral Effect Against Picornaviruses The test compounds were evaluated for anti-picornavirus activity by a multicycle cytopathic effect (CPE) reduction assay. The antiviral activity was initially determined using an MTS [3-(4,5-dimethylthiazol-2-yl)-5-(3-carboxymethoxyphenyl)-2-(4-sulfophenyl)-2H-tetrazolium]-based CPE reduction assay.

In this regard, cells grown to confluence in 96-well plates were infected with 100 50% cell culture infective doses ($CCID_{50}$) of virus. After an adsorption period of 2 hrs at 37° C., virus was removed and serial dilutions of the compounds were added. The cultures were further incubated at 37° C. for 3 days, until complete CPE was observed in the infected and untreated virus control (VC). After removal of the medium, 90 μl of a culture medium and 10 μl of MTS-phenazine methosulfate (Promega, Leiden, The Netherlands) were added to each well. After an incubation period of 2 hrs at 37° C., the optical density (OD) of each well was read at 498 nm in a microplate reader.

CPE values for evaluating antiviral activity were calculated using the following Mathmatic Formula 3:

$$\% \ CPE = 100 \times \frac{OD_{CC} - OD_{virus+compound}}{OD_{CC} - OD_{VC}} \quad \text{[Mathmatic Formula 3]}$$

CPE values for evaluating cytotoxicity were calculated using the following Mathmatic Formula 4:

$$\% \ CPE = 100 \times \frac{OD_{CC} - OD_{compound}}{OD_{CC} - OD_{Blank}} \quad \text{[Mathmatic Formula 4]}$$

In Formulas 3 and 4, $OD_{CC}$ corresponds to the OD of the uninfected and untreated, background cell cultures, $OD_{VC}$ represents the OD of the infected and untreated control cell cultures, $OD_{virus+Compound}$ represents the OD of the virus-infected cell cultures treated with a given concentration of compound, and ODBlank represents the OD of the well added with the cell culture medium alone.

The 50% effective concentration ($EC_{50}$) and the 50% cytotoxic concentration ($CC_{50}$) were defined as the concentrations of compound that offered 50% protection against virus-induced CPE and that killed cells by 50%, respectively, and were calculated using logarithmic interpolation.

$CC_{50}$ and $EC_{50}$ against various viruses of some compounds are given in Table 3, below.

TABLE 5

|  | Ex. 19 | Ex. 36 | Ex. 74 |
|---|---|---|---|
| $CC_{50}$ [μM] | >100 | >50 | >100 |
| Coxsackie B3[c] $EC_{50}$ [μM] | <0.01 | <0.01 | — |
| Coxsackie A16[d] $EC_{50}$ [μM] | 0.064 ± 0.010 | — | 13 ± 0.32 |
| Coxsackie A9[f] $EC_{50}$ [μM] | — | 0.0070 ± 0.00018 | — |
| Coxsackie A21[d] $EC_{50}$ [μM] | 0.67 ± 0.13 | — | 26 ± 0.34 |
| Entero 71[e] $EC_{50}$ [μM] | 0.10 ± 0.0018 | 0.0067 ± 0.00078 | 3.3 ± 1.6 |
| Echo 9[d] $EC_{50}$ [μM] | 0.017 ± 0.0067 | 0.011 ± 0.0032 | 0.61 ± 0.038 |
| Echo 11[f] $EC_{50}$ [μM] | 0.017 ± 0.0078 | 0.0082 ± 0.0019 | 0.70 ± 0.24 |
| Polio 1[f] $EC_{50}$ [μM] | 0.79 ± 0.36 | 0.22 ± 0.050 | 20 ± 14 |
| Polio 2[f] $EC_{50}$ [μM] | — | — | — |
| Polio 3[f] $EC_{50}$ [μM] | <1.0 | <0.01 | — |
| Rhino 2[g] $EC_{50}$ [μM] | >50 | 7.8 ± 0.57 | >50 |
| Rhino 9[g] $EC_{50}$ [μM] | >50 | 1.2 ± 0.12 | >50 |
| Rhino 15[g] $EC_{50}$ [μM] | >50 | 1.5 ± 0.24 | >50 |
| Rhino 29[g] $EC_{50}$ [μM] | >50 | 5.5 ± 0.72 | >50 |
| Rhino 39[g] $EC_{50}$ [μM] | >50 | 1.4 ± 0.20 | >50 |

TABLE 5-continued

|  | Ex. 19 | Ex. 36 | Ex. 74 |
|---|---|---|---|
| Rhino 41$^g$ EC$_{50}$ [μM] | >50 | 0.54 ± 0.0030 | >50 |
| Rhino 45$^g$ EC$_{50}$ [μM] | 4.6 ± 0.0083 | <0.078$^i$ | >50 |
| Rhino 59$^g$ EC$_{50}$ [μM] | — | — | >50 |
| Rhino 63$^g$ EC$_{50}$ [μM] | >50 | >10 | >50 |
| Rhino 85$^g$ EC$_{50}$ [μM] | >50 | 7.5 ± 1.2 | >50 |
| Rhino 89$^g$ EC$_{50}$ [μM] | >50 | 0.49 ± 0.038 | >50 |
| Rhino 14$^g$ EC$_{50}$ [μM] | 0.45 ± 0.41 | 0.35 ± 0.32 | >50 |
| Rhino 42$^g$ EC$_{50}$ [μM] | >50 | — | >50 |
| Rhino 70$^g$ EC$_{50}$ [μM] | 2.0 ± 0.12 | >0.078$^i$ | >50 |
| Rhino 72$^g$ EC$_{50}$ [μM] | 4.6 ± 0.092 | — | >50 |
| Rhino 86$^g$ EC$_{50}$ [μM] | 26 ± 18 | — | 26 ± 18 |

In Table 5, the superscript c represents incubation at 37° C. in Vero cells, the superscript d represents incubation at 37° C. in MRC-5 cells, the superscript e represents incubation at 37° C. in RD cells, the superscrip f represents incubation at 37° C. in BGM cells, the superscript g represents incubation at 37° C. in HeLa cells, and the superscript i represents 100% inhibition of viral replication with compounds of 0.078 μM or higher.

As can be seen in Table 5, the 1,3-Dioxoindene derivatives according to the present invention are low in cytotoxicity because their CC$_{50}$ was measured at 50 μM or higher, especially the compound of EXAMPLE 19 and EXAMPLE 74 are low in cytotoxicity because their CC$_{50}$ was measured at 100 μM or higher. In addition, the 1,3-Dioxoindene derivatives were observed to have an EC$_{50}$ of 26 μM or less against coxsackieviruses B3, A16, A9, and A21. Particularly high antiviral activity was detected in the compound of EXAMPLE 19 and EXAMPLE 36 with an EC$_{50}$ of as low as 0.01 μM.

With regard to enterovirus 71, the 1,3-Dioxoindene derivatives according to the present invention showed an EC$_{50}$ of 3.3 μM or less. Particularly high antiviral activity was detected in the compound of EXAMPLE 36 with an EC$_{50}$ of as low as 0.0067 μM.

The 1,3-Dioxoindene derivatives according to the invention showed an EC$_{50}$ of 0.70 μM or less against echovirus 9 and echovirus 11, while the higest antiviral activity was dected in the compound of EXAMPLE 36 as demonstrated by the EC$_{50}$ of 0.0082 μM.

In the case of polioviruses 1, 2 and 3, EC$_{50}$ values of the 1,3-Dioxoindene derivatives according to present invention were measured to be 20 μM or less. Particularly high antiviral activity was detected in the compound of EXAMPLE 36 with an EC$_{50}$ of as low as 0.01 μM.

Also, the 1,3-Dioxoindene derivatives according to the invention were highly inhibitory of rhinoviruses. For example, EC$_{50}$ of 50 μM or more was detected against rhinoviruses 2, 9, 15, 29, 39, 41, 45, 59, 63, 85, 89, 14, 42, 70, 72, and 86. Particularly high antiviral activity was detected in the compound of EXAMPLE 36 with an EC$_{50}$ of 0.078 μM or less against rhinoviruses 45 and 70.

Consequently, the 1,3-Dioxoindene derivatives of the present invention are of low cytotoxicity and exhibit excellent antiviral activity against picornaviruses including coxsackie-, entero-, echo-, polio- and rhinoviruses, so that they can be usefully applied to the prevention or treatment of picornavirus-caused respiratory, cardiocirculatory, and nerveous system diseases, including poliomyelitis, paralysis, acute hemorrhagic conjunctivitis, viral meningitis, hand-foot-and-mouth disease, vesicular disease, hepaitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis and otitis media.

Formulation Example 1

Preparation of Pharmaceutical Formulations

<1-1> Preparation of Powder
1,3-Dioxoindene derivative: 2 g
Lactose: 1 g
The above ingredients were mixed and loaded into an airtight sac to produce a powder agent.

<1-2> Preparation of Tablet
1,3-Dioxoindene derivative: 100 mg
Corn starch: 100 mg
Lactose: 100 mg
Mg stearate: 2 mg
These ingredients were mixed and prepared into tablets using a typical tabletting method.

<1-3> Preparation of Capsule
1,3-Dioxoindene derivative: 100 mg
Corn starch: 100 mg
Lactose: 100 mg
Mg stearate: 2 mg
These ingredients were mixed and loaded into gelatin capsules according to a typical method to produce capsules.

<1-4> Preparation of Injection
1,3-Dioxoindene derivative: 10 μg/ml
Diluted Hydrochloric acid BP: to be pH 3.5
Sodium chloride BP for injection: maximum 1 ml
The 1,3-Dioxoindene derivative of the present invention was dissolved in a appropriate volume of sodium chloride BP for injection. The pH of the resultant solution was regulated to be pH 3.5 with dil.HCl BP, and then its volume was regulated with sodium chloride BP for Injection and the solution was mixed completely. The solution was then filled in 5-ml type 1 ample that is made of transparent glass. The air was sealed in upper lattice by melting the glass. The solution contained in ample was autoclaved at 120° C. for 15 min or more to be sterilized and thereby to obtain an injection.

INDUSTRIAL APPLICABILITY

Having excellent inhibitory activity against picornaviruses including coxsackie-, entero-, echo-, Polio-, and rhinoviruses, as well as exhibiting low cytotoxicity, as described hitherto, the 1,3-Dioxoindene derivative of Chemical Formula 1 can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hapatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media.

The invention claimed is:
1. A compound of Formula 1, or a pharmaceutically-acceptable salt or optical isomer thereof:

[Formula 1]

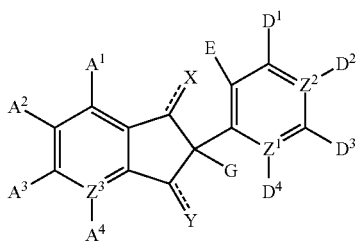

where, $A^1$, $A^2$, $A^3$ and $A^4$ are independently selected from a group consisting of —H, halogen, —OH, —CN, —$N_3$, $C_1$~$C_{10}$ alkoxy, $C_1$~$C_{10}$ straight- or branched-chain alkyl, —O(C=O)$R^1$, —(C=O)$R^1$, —(C=O)O$R^1$, —O(C=O)O$R^1$, —O(C=O)N$R^1R^2$, —$NO_2$, —N$R^1R^2$, —N$R^1$(C=O)$R^2$, —N$R^1$(C=S)$R^2$, —N$R^1$(C=O)O$R^2$, —N$R^1$(C=O)—N$R^2R^3$ and —N$R^1$(C=S)—N$R^2R^3$, or two or more neighboring substituents $A^1$, $A^2$, $A^3$ and $A^4$ may form a ring together, wherein a ring formed by two or more neighboring substituents $A^1$, $A^2$, $A^3$ and $A^4$ may include one or more hetero atom, and the hetero atom is N, O or S, provided that at least one of $A^1$-$A^4$ is not hydrogen;

G is —OH, —CN, —$N_3$, $C_1$~$C_{10}$ alkoxy, —O(C=O)$R^1$, —(C=O)$R^1$, —(C=O)O$R^1$, —O(C=O)O$R^1$, —O(C=O)N$R^1R^2$, —$NO_2$, —N$R^1R^2$, —N$R^1$(C=O)$R^2$, —N$R^1$(C=S)$R^2$, —N$R^1$(C=O)O$R^2$, —N$R^1$(C=O)—N$R^2R^3$, —N$R^1$(C=S)—N$R^2R^3$ or

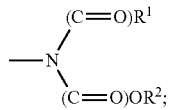

$D^1$, $D^2$, $D^3$ and $D^4$ are independently selected from a group consisting of —H, halogen, —OH, —CN, $C_1$~$C_{10}$ alkoxy, $C_1$~$C_{10}$ straight- or branched-chain alkyl, $C_6$~$C_{12}$ aryl, —($CH_2$)$_n$—(C=O)O$R^1$, —O(C=O)$R^1$, —(C=O)$R^1$, —(C=O)O$R^1$, —O(C=O)O$R^1$, —O(C=O)N$R^1R^2$, —$NO_2$, —N$R^1R^2$, —N$R^1$(C=O)$R^2$, —N$R^1$(C=S)$R^2$, —N$R^1$(C=O)O$R^2$, —N$R^1$(C=O)—N$R^2R^3$, —S$R^1$ and —N$R^1$(C=S)—N$R^2R^3$, or two or more neighboring substituents of $D^1$, $D^2$, $D^3$ and $D^4$ may form a ring together, a ring formed by two or more neighboring substituent of $D^1$, $D^2$, $D^3$ and $D^4$ may include one or more hetero atom, and the hetero atom is N, O or S;

E is —H, —OH, —O(C=O)$R^1$, —(C=O)$R^1$, —(C=O)O$R^1$, —O(C=O)O$R^1$, —O(C=O)N$R^1R^2$, —$NO_2$, —N$R^1R^2$, —N$R^1$(C=O)$R^2$, —S$R^1$, —N$R^1$(C=S)$R^2$, —N$R^1$(C=O)O$R^2$, —N$R^1$(C=O)—N$R^2R^3$ or —N$R^1$(C=S)—N$R^2R^3$;

$R^1$, $R^2$ and $R^3$ are, each independently, hydrogen, nonsubstituted or phenyl-substituted $C_1$~$C_{10}$ straight- or branched-chain alkyl, $C_1$~$C_{10}$ alkoxy, nonsubstituted or phenyl-substituted $C_1$~$C_{10}$ straight- or branched-chain alkenyl, $C_3$~$C_7$ cycloalkyl or nonsubstituted or phenyl-substituted $C_6$~$C_{12}$ aryl;

X and Y are, each independently, hydrogen, oxygen, hydroxy or sulfur;

$Z^1$, $Z^2$ and $Z^3$ are carbon or nitrogen;

n is integer between 1~10; and

═══ denotes single or double bond.

2. The compound of claim 1, or a pharmaceutically-acceptable salt or optical isomer thereof, wherein, $A^1$, $A^2$, $A^3$ and $A^4$ are independently selected from a group consisting of —H, halogen, $C_1$~$C_{10}$ straight- or branched-chain alkyl, —N$R^1R^2$, —N$R^1$(c=O)$R^2$, or two or more neighboring substituents $A^1$, $A^2$, $A^3$ and $A^4$ may form a ring together, wherein a ring formed by two or more neighboring substituents $A^1$, $A^2$, $A^3$ and $A^4$ may include one or more hetero atom, and the hetero atom is N, O or S;

G is —OH, —O(C=O)$R^1$, —O(C=O)O$R^1$, —N$R^1$(C=O)$R^2$, —N$R^1$(C=O)O$R^2$ or

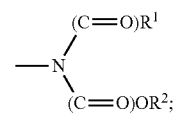

$D^1$, $D^2$, $D^3$ and $D^4$ are independently selected from a group consisting of halogen, $C_1$~$C_{10}$ straight- or branched-chain alkyl, —N$R^1$(C=O)$R^2$, —N$R^1$(C=O)O$R^2$ and —N$R^1$(C=O)—N$R^2R^3$, or two or more neighboring substituents $D^1$, $D^2$, $D^3$ and $D^4$ may form a ring together, wherein a ring formed by two or more neighboring substituents $D^1$, $D^2$, $D^3$ and $D^4$ may include one or more hetero atom, and the hetero atom is N, O or S;

E is —H, —OH, —O$R^1$, —O(C=O)$R^1$, —O(C=O)O$R^1$, —O(C=O)N$R^1R^2$, —N$R^1$(C=O)$R^2$ or —N$R^1$(C=O)O$R^2$;

$R^1$, $R^2$ and $R^3$ are, each independently, hydrogen, nonsubstituted or phenyl-substituted $C_1$~$C_9$ straight- or branched-chain alkyl, nonsubstituted or phenyl-substituted $C_1$~$C_5$ straight- or branched-chain alkenyl or $C_6$~$C_{10}$ aryl;

X and Y are, each independently, oxygen or hydroxy;

$Z^1$, $Z^2$ and $Z^3$ are carbon;

n is integer between 1~5; and

═══ denotes single or double bond.

3. The compound of claim 1, or a pharmaceutically-acceptable salt or optical isomer thereof, wherein, $A^1$, $A^2$, $A^3$ and $A^4$ are independently selected from a group consisting of —H, halogen and —N$R^1R^2$;

G is —OH, —N$R^1$(C=O)$R^2$ or —N$R^1$(C=O)O$R^2$;

$D^1$, $D^2$, $D^3$ and $D^4$ are independently selected from a group consisting of halogen, $C_1$~$C_{10}$ straight- or branched-chain alkyl and —N$R^1$(C=O)$R^2$;

E is —H, —OH, —O$R^1$, —O(C=O)$R^1$, —O(C=O)O$R^1$ or —O(C=O)N$R^1R^2$;

$R^1$, $R^2$ and $R^3$ are, each independently, hydrogen, nonsubstituted or phenyl-substituted $C_1$~$C_8$ straight- or branched-chain alkyl, nonsubstituted or phenyl-substituted $C_1$~$C_4$ straight- or branched-chain alkenyl or $C_6$~$C_{10}$ aryl;

X and Y are oxygen;

$Z^1$, $Z^2$ and $Z^3$ are carbon;

n is integer between 1~3; and

═══ denotes double bond.

4. The compound of claim 1, or a pharmaceutically-acceptable salt or optical isomer thereof, wherein, $A^1$, $A^2$, $A^3$ and $A^4$ are independently selected from a group consisting of —H and —N$R^1R^2$;

G is —N$R^1$(C=O)$R^2$;

$D^1$, $D^2$, $D^3$ and $D^4$ are $C_1$~$C_{10}$ straight- or branched-chain alkyl;

E is —O(C=O)$R^1$;

R¹, R² and R³ are, each independently, hydrogen or $C_1$~$C_7$ straight- or branched-chain alkyl;

X and Y are oxygen;

$Z^1$, $Z^2$ and $Z^3$ are carbon;

n is integer between 1~3; and

=== denotes double bond.

5. The compound, pharmaceutically acceptable salt, or optical isomer of claim 1, wherein the compound is selected from the group consisting of:
- 27) 2-(2-Acetoxy-4-isopropylphenyl)-5-methoxy-1,3-dioxo-2,3-dihydro-1H-inden-2-yl acetate;
- 28) 2-(2-Hydroxy-4-isopropylphenyl)-2-methoxy-1H-inden-1,3(2H)-dione;
- 36) Acetic acid 2-(2-acetoxy-4-isopropyl-phenyl)-4-amino-1,3-dioxo-indan-2-yl ester;
- 37) Acetic acid 2-(2-acetoxy-4-isopropyl-phenyl)-4-nitro-1,3-dioxo-indan-2-yl ester;
- 38) 2-Hydroxy-2-(4-isopropyl-2-methoxyphenyl)-4-nitro-2H-inden-1,3-dione;
- 40) 2-Azido-2-(4-isopropyl-2-methoxyphenyl)-4-nitro-2H-inden-1,3-dione;
- 41) 4-Amino-2-hydroxy-2-(4-isopropyl-2-methoxyphenyl)-2H-inden-1,3-dione;
- 42) N-(2-Hydroxy-2-(4-isopropyl-2-methoxyphenyl)-7-nitro-1,3-dioxo-2,3-dihydro-1H-inden-4-yl)acetamide;
- 43) N-(2-Hydroxy-2-(4-isopropyl-2-methoxyphenyl)-5-nitro-1,3-dioxo-2,3-dihydro-1H-inden-4-yl)acetamide;
- 44) N-(7-Amino-2-hydroxy-2-(4-isopropyl-2-methoxyphenyl)-1,3-dioxo-2,3-dihydro-1H-inden-4-yl)acetamide;
- 45) N-(5-Amino-2-hydroxy-2-(4-isopropyl-2-methoxyphenyl)-1,3-dioxo-2,3-dihydro-1H-inden-4-yl)acetamide;
- 46) 4,7-Diamino-2-hydroxy-2-(4-isopropyl-2-methoxyphenyl)-2H-inden-1,3-dione;
- 47) 4,5-Diamino-2-hydroxy-2-(4-isopropyl-2-methoxyphenyl)-2H-inden-1,3-dione;
- 66) N-(2-Amino-2-(4-isopropyl-2-methoxyphenyl)-1,3-dioxo-2,3-dihydro-1H-inden-4-yl)acetamide;
- 67) N,N'-(2-(4-Isopropyl-2-methoxyphenyl)-1,3-dioxo-2,3-dihydro-1H-inden-2,4-diyl)diacetamide;
- 81) 2-(4-Amino-1,3-dioxo-2-pentanamido-2,3-dihydro-1H-inden-2-yl)-5-isopropylphenyl pentanoate;
- 82) 2-(4-Amino-2-hexanamido-1,3-dioxo-2,3-dihydro-1H-inden-2-yl)-5-isopropylphenyl hexanoate;
- 83) 2-(4-Amino-2-heptanamido-1,3-dioxo-2,3-dihydro-1H-inden-2-yl)-5-isopropylphenyl heptanoate;
- 84) 2-(4-Amino-1,3-dioxo-2-propionamido-2,3-dihydro-1H-inden-2-yl)-5-isopropylphenyl propionate;
- 85) 2-(4-Amino-2-butyramido-1,3-dioxo-2,3-dihydro-1H-inden-2-yl)-5-isopropylphenyl butyrate;
- 91) 2-(4-Amino-2-octanamido-1,3-dioxo-2,3-dihydro-1H-inden-2-yl)-5-isopropylphenyl octanoate;
- 94) N-(2-(4-Acetamido-2-hydroxy-7-nitro-1,3-dioxo-2,3-dihydro-1H-inden-2-yl)-4,5-dimethylphenyl)isobutyramide;
- 96) 2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate;
- 100) 2-(2-Acetamido-4-amino-1,3-dioxo-2,3-dihydro-1H-inden-2-yl)-5-isopropylphenyl dimethylcarbamate;
- 103) 2-(2-Acetamido-4-amino-1,3-dioxo-2,3-dihydro-1H-inden-2-yl)-5-isopropylphenyl ethylcarbamate;
- 107) N-[2-(4-Amino-2-hydroxy-1,3-dioxo-indan-2-yl)-4,5-dimethoxy-phenyl]-isobutyramide; and
- 108) N-[2-(2-Hydroxy-5,6-dimethoxy-1,3-dioxo-indan-2-yl)-4,5-dimethoxy-phenyl]-sobutyramide.

6. The compound, pharmaceutically acceptable salt, or optical isomer of claim 1, wherein the compound is selected from the group consisting of:
- 27) 2-(2-Acetoxy-4-isopropylphenyl)-5-methoxy-1,3-dioxo-2,3-dihydro-1H-inden-2-yl acetate;
- 36) Acetic acid 2-(2-acetoxy-4-isopropyl-phenyl)-4-amino-1,3-dioxo-indan-2-yl ester;
- 37) Acetic acid 2-(2-acetoxy-4-isopropyl-phenyl)-4-nitro-1,3-dioxo-indan-2-yl ester;
- 38) 2-Hydroxy-2-(4-isopropyl-2-methoxyphenyl)-4-nitro-2H-inden-1,3-dione;
- 40) 2-Azido-2-(4-isopropyl-2-methoxyphenyl)-4-nitro-2H-inden-1,3-dione;
- 41) 4-Amino-2-hydroxy-2-(4-isopropyl-2-methoxyphenyl)-2H-inden-1,3-dione;
- 42) N-(2-Hydroxy-2-(4-isopropyl-2-methoxyphenyl)-7-nitro-1,3-dioxo-2,3-dihydro-1H-inden-4-yl)acetamide;
- 43) N-(2-Hydroxy-2-(4-isopropyl-2-methoxyphenyl)-5-nitro-1,3-dioxo-2,3-dihydro-1H-inden-4-yl)acetamide;
- 44) N-(7-Amino-2-hydroxy-2-(4-isopropyl-2-methoxyphenyl)-1,3-dioxo-2,3-dihydro-1H-inden-4-yl)acetamide;
- 45) N-(5-Amino-2-hydroxy-2-(4-isopropyl-2-methoxyphenyl)-1,3-dioxo-2,3-dihydro-1H-inden-4-yl)acetamide;
- 46) 4,7-Diamino-2-hydroxy-2-(4-isopropyl-2-methoxyphenyl)-2H-inden-1,3-dione;
- 47) 4,5-Diamino-2-hydroxy-2-(4-isopropyl-2-methoxyphenyl)-2H-inden-1,3-dione;
- 66) N-(2-Amino-2-(4-isopropyl-2-methoxyphenyl)-1,3-dioxo-2,3-dihydro-1H-inden-4-yl)acetamide;
- 67) N,N'-(2-(4-Isopropyl-2-methoxyphenyl)-1,3-dioxo-2,3-dihydro-1H-inden-2,4-diyl)diacetamide;
- 81) 2-(4-Amino-1,3-dioxo-2-pentanamido-2,3-dihydro-1H-inden-2-yl)-5-isopropylphenyl pentanoate;
- 82) 2-(4-Amino-2-hexanamido-1,3-dioxo-2,3-dihydro-1H-inden-2-yl)-5-isopropylphenyl hexanoate;
- 83) 2-(4-Amino-2-heptanamido-1,3-dioxo-2,3-dihydro-1H-inden-2-yl)-5-isopropylphenyl heptanoate;
- 84) 2-(4-Amino-1,3-dioxo-2-propionamido-2,3-dihydro-1H-inden-2-yl)-5-isopropylphenyl propionate;
- 85) 2-(4-Amino-2-butyramido-1,3-dioxo-2,3-dihydro-1H-inden-2-yl)-5-isopropylphenyl butyrate;
- 91) 2-(4-Amino-2-octanamido-1,3-dioxo-2,3-dihydro-1H-inden-2-yl)-5-isopropylphenyl octanoate;
- 94) N-(2-(4-Acetamido-2-hydroxy-7-nitro-1,3-dioxo-2,3-dihydro-1H-inden-2-yl)-4,5-dimethylphenyl)isobutyramide;
- 96) 2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate;
- 100) 2-(2-Acetamido-4-amino-1,3-dioxo-2,3-dihydro-1H-inden-2-yl)-5-isopropylphenyl dimethylcarbamate;
- 103) 2-(2-Acetamido-4-amino-1,3-dioxo-2,3-dihydro-1H-inden-2-yl)-5-isopropylphenyl ethylcarbamate;
- 107) N-[2-(4-Amino-2-hydroxy-1,3-dioxo-indan-2-yl)-4,5-dimethoxy-phenyl]-isobutyramide; and
- 108) N-[2-(2-Hydroxy-5,6-dimethoxy-1,3-dioxo-indan-2-yl)-4,5-dimethoxy-phenyl]-sobutyramide.

7. The compound, pharmaceutically acceptable salt, or optical isomer of claim 1, wherein the compound is selected from the group consisting of:
- 36) Acetic acid 2-(2-acetoxy-4-isopropyl-phenyl)-4-amino-1,3-dioxo-indan-2-yl ester;
- 81) 2-(4-Amino-1,3-dioxo-2-pentanam ido-2,3-dihydro-1H-inden-2-yl)-5-isopropylphenyl pentanoate;
- 82) 2-(4-Amino-2-hexanamido-1,3-dioxo-2,3-dihydro-1H-inden-2-yl)-5-isopropylphenyl hexanoate;
- 83) 2-(4-Amino-2-heptanamido-1,3-dioxo-2,3-dihydro-1H-inden-2-yl)-5-isopropylphenyl heptanoate;
- 84) 2-(4-Amino-1,3-dioxo-2-propionamido-2,3-dihydro-1H-inden-2-yl)-5-isopropylphenyl propionate;
- 85) 2-(4-Amino-2-butyramido-1,3-dioxo-2,3-dihydro-1H-inden-2-yl)-5-isopropylphenyl butyrate;
- 94) N-(2-(4-Acetamido-2-hydroxy-7-nitro-1,3-dioxo-2,3-dihydro-1H-inden-2-yl)-4,5-dimethylphenyl)isobutyramide;
- 96) 2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate;
- 100) 2-(2-Acetamido-4-amino-1,3-dioxo-2,3-dihydro-1H-inden-2-yl)-5-isopropylphenyl dimethylcarbamate; and
- 103) 2-(2-Acetamido-4-amino-1,3-dioxo-2,3-dihydro-1H-inden-2-yl)-5-isopropylphenyl ethylcarbamate.

8. A method for preparing a compound of formula 1a:

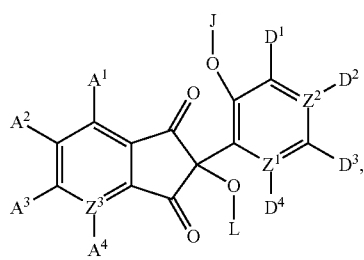

1a or a pharmaceutically acceptable salt or optical isomer thereof, wherein $A^1$, $A^2$, $A^3$, $A^4$, $D^1$, $D^2$, $D^3$, $D^4$, $Z^1$, $Z^2$ and $Z^3$ are as defined in claim 1, and J and L are, independently, identical to $A^1$, $A^2$, $A^3$, $A^4$, $D^1$, $D^2$, $D^3$ or $D^4$; comprising acylating or alkylating a compound of Formula 2:

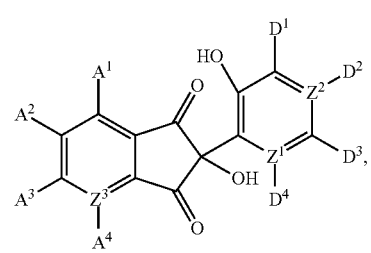

2 in the presence of a base and a solvent to afford the compound of formula 1a.

9. A method for preparing a compound of formula 1b:

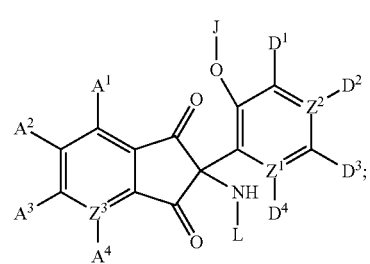

1b or a pharmaceutically acceptable salt or optical isomer thereof, wherein $A^1$, $A^2$, $A^3$, $A^4$, $D^1$, $D^2$, $D^3$, $D^4$, $Z^1$, $Z^2$ and $Z^3$ are as defined in claim 1, and J and L are, independently, identical to $A^1$, $A^2$, $A^3$, $A^4$, $D^1$, $D^2$, $D^3$ or $D^4$; comprising:
treating a compound of Formula 2:

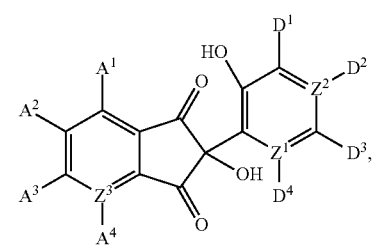

2 with thionyl chloride or oxalic chloride in the presence of a reacting base and a solvent, and then treating the resulting mixture with ammonia to afford a compound of formula 3:

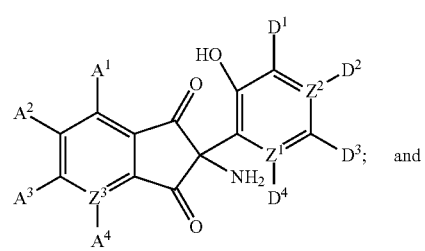

3 and acylating or alkylating the compound of formula 3 in the presence of a base and a solvent to afford the compound of formula 1b.

10. A method for treating a viral disease in a patient, comprising administering a therapeutically effective amount of the compound, pharmaceutically acceptable salt, or optical isomer of claim 1 to the patient.

11. The method of claim 10, wherein the viral disease is caused by a Coxsackie virus.

12. The method of claim 10, wherein the viral disease is caused by a polio virus.

13. The method of claim 10, wherein the viral disease is caused by an echo virus.

14. The method of claim 10, wherein the viral disease is caused by an entero virus.

15. The method of claim 10, wherein the viral disease is caused by a rhino virus.

16. The method of claim 10, wherein the viral disease is caused by a picorna virus.

17. The method of claim 10, wherein the viral disease comprises: polio, paralysis, acute hemorrhagic conjunctivitis, viral meningitis, hand-foot and mouth disease, swine vesicular disease (SVD), hepatitis A, myositis, myocarditis, pancreatitis, diabetes, muscle aches influenza, encephalitis, flu, herpangina, or foot and mouth disease.

18. A pharmaceutical composition comprising the compound, pharmaceutically acceptable salt, or optical isomer of claim 1 and a pharmaceutically acceptable diluent or excipient.

19. A compound selected from the group consisting of:
1) Ethyl 2-(4-acetoxy-3-(2-acetoxy-1,3-dioxo-2,3-dihydro-1H-inden-2-yl)-5-m ethoxyphenyl)acetate;
2) 2-(2-Acetoxy-1,3-dioxo-2,3-dihydro-1H-inden-2-yl)-4,5-dimethylphenyl acetate;
3) 2-(2-Acetoxy-1,3-dioxo-2,3-dihydro-1H-inden-2-yl)-5-chlorophenyl acetate;
4) 6-(2-Acetoxy-1,3-dioxo-2,3-dihydro-1H-inden-2-yl)-2,3-dichlorophenyl acetate;
5) 2-(2-Acetoxy-1,3-dioxo-2,3-dihydro-1H-inden-2-yl)-4,6-dichlorophenyl acetate;
6) 2-(2-Acetoxy-1,3-dioxo-2,3-dihydro-1H-inden-2-yl)-5-ethylphenyl acetate;
7) 2-(2-Acetoxy-1,3-dioxo-2,3-dihydro-1H-inden-2-yl)-4-methoxyphenyl acetate;
8) 4-(2-Acetoxy-1,3-dioxo-2,3-dihydro-1H-inden-2-yl) biphenyl-3-yl acetate;
9) 2-(2-Acetoxy-1,3-dioxo-2,3-dihydro-1H-inden-2-yl)-4-nitrophenyl acetate;
10) 3-(2-Acetoxy-1,3-dioxo-2,3-dihydro-1H-inden-2-yl) biphenyl-4-yl acetate;
11) 2-(2-Acetoxy-1,3-dioxo-2,3-dihydro-1H-inden-2-yl)-4-propylphenyl acetate;
12) 2-(2-Acetoxy-1,3-dioxo-2,3-dihydro-1H-inden-2-yl)-4-ethyl phenyl acetate;
13) 2-(2-Acetoxy-1,3-dioxo-2,3-dihydro-1H-inden-2-yl)-4-sec-butylphenyl acetate;
14) 2-(2-Acetoxy-1,3-dioxo-2,3-dihydro-1H-inden-2-yl)-4-tert-butylphenyl acetate;
15) 2-(2-Acetoxy-1,3-dioxo-2,3-dihydro-1H-inden-2-yl)-5-tert-butylphenyl acetate;
16) 2-(2-Acetoxy-1,3-dioxo-2,3-dihydro-1H-inden-2-yl)-3,4,5-trimethylphenyl acetate;
17) 2-(2-Acetoxy-1,3-dioxo-2,3-dihydro-1H-inden-2-yl)-4-tert-pentylphenyl acetate;
18) Acetic acid 2-(2,3-diacetoxy-5-methyl-phenyl)-1,3-dioxo-indan-2-yl ester;
19) Acetic acid 2-(2-acetoxy-4-isopropyl-phenyl)-1,3-dioxo-indan-2-yl ester;
20) 2-(4-Acetyl-2-hydroxy-phenyl)-2-hydroxy-indan-1,3-dione;
21) 2-(1,3-Dioxo-2-(propionyloxy)-2,3-dihydro-1H-inden-2-yl)-5-isopropylphenyl propionate;
22) 2-(2-(Butyryloxy)-1,3-dioxo-2,3-dihydro-1H-inden-2-yl)-5-isopropylphenyl butyrate;
23) 2-(2-Hydroxy-4-isopropylphenyl)-1,3-dioxo-2,3-dihydro-1H-inden-2-yl benzoate;
24) 2-(2-Benzyloxy-4-isopropyl-phenyl)-2-hydroxy-indan-1,3-dione;
25) 2-(2-Benzyloxy-4-isopropyl-phenyl)-2-methoxy-indan-1,3-dione;
27) 2-(2-Acetoxy-4-isopropylphenyl)-5-methoxy-1,3-dioxo-2,3-dihydro-1H-inden-2-yl acetate;
28) 2-(2-Hydroxy-4-isopropylphenyl)-2-methoxy-1H-inden-1,3(2H)-dione;
29) 2-(1,3-Dioxo-2-(pivaloyloxy)-2,3-dihydro-1H-inden-2-yl)-5-isopropylphenyl pivalate;
30) 2-(2-Hydroxy-1,3-dioxo-2,3-dihydro-1H-inden-2-yl)-5-isopropylphenyl cinnamate;
31) Dimethyl-carbamic acid 2-(2-dimethylcarbamoyloxy-1,3-dioxo-indan-2-yl)-5-isopropyl-phenyl ester;
32) 2-(2-(Acryloyloxy)-1,3-dioxo-2,3-dihydro-1H-inden-2-yl)-5-isopropylphenyl acrylate;
33) Diethyl-carbamic acid 2-(2-diethylcarbamoyloxy-1,3-dioxo-indan-2-yl)-5-isopropyl-phenyl ester;
34) 2-(2-Hydroxy-1,3-dioxo-2,3-dihydro-1H-inden-2-yl)-5-isopropylphenyl diethylcarbamate;
35) 2-Hydroxy-2-(4-hydroxy-2,5-dimethylphenyl)-1H-inden-1,3(2H)-dione;
36) Acetic acid 2-(2-acetoxy-4-isopropyl-phenyl)-4-amino-1,3-dioxo-indan-2-yl ester;
37) Acetic acid 2-(2-acetoxy-4-isopropyl-phenyl)-4-nitro-1,3-dioxo-indan-2-yl ester;
38) 2-Hydroxy-2-(4-isopropyl-2-methoxyphenyl)-4-nitro-2H-inden-1,3-dione;
39) 2-Chloro-2-(4-isopropyl-2-methoxyphenyl)-4-nitro-2H-inden-1,3-dione;
40) 2-Azido-2-(4-isopropyl-2-methoxyphenyl)-4-nitro-2H-inden-1,3-dione;
41) 4-Amino-2-hydroxy-2-(4-isopropyl-2-methoxyphenyl)-2H-inden-1,3-dione;
42) N-(2-Hydroxy-2-(4-isopropyl-2-methoxyphenyl)-7-nitro-1,3-dioxo-2,3-dihydro-1H-inden-4-yl)acetamide;
43) N-(2-Hydroxy-2-(4-isopropyl-2-methoxyphenyl)-5-nitro-1,3-dioxo-2,3-dihydro-1H-inden-4-yl)acetamide;
44) N-(7-Amino-2-hydroxy-2-(4-isopropyl-2-methoxyphenyl)-1,3-dioxo-2,3-dihydro-1H-inden-4-yl)acetamide;
45) N-(5-Amino-2-hydroxy-2-(4-isopropyl-2-methoxyphenyl)-1,3-dioxo-2,3-dihydro-1H-inden-4-yl)acetamide;
46) 4,7-Diam ino-2-hydroxy-2-(4-isopropyl-2-methoxyphenyl)-2H-inden-1,3-dione;
47) 4,5-Diam ino-2-hydroxy-2-(4-isopropyl-2-methoxyphenyl)-2H-inden-1,3-dione;
48) Methyl 2-(4-isopropyl-2(methoxycarbonyloxy)phenyl)-1,3-dioxo-2,3-dihydro-1H-inden-2-yl carbamate;
49) 2-(1,3-Dioxo-2-pentanamido-2,3-dihydro-1H-inden-2-yl)-5-isopropylphenyl pentanoate;
50) 2-(2-Isobutylamido-1,3-dioxo-2,3-dihydro-1H-inden-2-yl)-5-isopropylphenyl isobutyrate;
51) 2-Hydroxy-2-(2-hydroxy-4-isopropylphenyl)-2,3-dihydro-1H-inden-1-one;
52) 2-Azido-2-(4-isopropyl-2-methoxyphenyl)-2H-inden-1,3-dione;
53) 2-Amino-2-(4-isopropyl-2-methoxyphenyl)-2H-inden-1,3-dione;
54) N-(2-(4-Isopropyl-2-methoxyphenyl)-1,3-dioxo-2,3-dihydro-1H-inden-2-yl)acetamide;
55) N-(2-(4-Isopropyl-2-methoxyphenyl)-1,3-dioxo-2,3-dihydro-1H-inden-2-yl)benzamide;
56) N-(2-(4-Isopropyl-2-methoxyphenyl)-1,3-dioxo-2,3-dihydro-1H-inden-2-yl)cyclopropancarboxamide;
57) 2-(2-(Methylthio)phenyl)-2H-inden-1,3-dione;
58) 2-(4-(Methylthio)phenyl)-2H-inden-1,3-dione;
59) Methyl 2-(4-isopropyl-2-methoxyphenyl)-1,3-dioxo-2,3-dihydro-1H-inden-2-ylcarbamate;
60) 1-Ethyl-3-(2,3-dihydro-2-(4-isopropyl-2-methoxyphenyl)-1,3-dioxo-1H-inden-2-yl)urea;

61) 1-(2,3-Dihydro-2-(4-isopropyl-2-methoxyphenyl)-1,3-dioxo-1H-inden-2-yl)urea;
62) Isopropyl 2-(4-isopropyl-2-methoxyphenyl)-1,3-dioxo-2,3-dihydro-1H-inden-2-ylcarbamate;
63) 1-(2-(4-Isopropyl-2-methoxyphenyl)-1,3-dioxo-2,3-dihydro-1H-inden-2-yl)-3-methoxy urea;
64) Ethyl 2-(4-isopropyl-2-methoxyphenyl)-1,3-dioxo-2,3-dihydro-1H-inden-2-ylcarbamate;
65) N-(2-Bromo-2-(4-isopropyl-2-methoxyphenyl)-1,3-dioxo-2,3-dihydro-1H-inden-4-yl)acetamide;
66) N-(2-Amino-2-(4-isopropyl-2-methoxyphenyl)-1,3-dioxo-2,3-dihydro-1H-inden-4-yl)acetamide;
67) N,N'-(2-(4-Isopropyl-2-methoxyphenyl)-1,3-dioxo-2,3-dihydro-1H-inden-2,4-diyl)diacetamide;
68) 2-(1,3-Dioxo-2-propionam ido-2,3-dihydro-1H-inden-2-yl)-5-isopropylphenyl propionate;
69) 2-(1,3-Dioxo-2-pentanamido-2,3-dihydro-1H-inden-2-yl)-5-isopropylphenyl pentanoate;
70) 2-(2-Benzam ido-1,3-dioxo-2,3-dihydro-1H-inden-2-yl)-5-isopropylphenyl benzoate;
71) 2-(2-Acetoxy-1,3-dioxo-2,3-dihydro-1H-inden-2-yl)-6-methylpyridin-3-yl acetate;
72) 2-Hydroxy-2-(4-hydroxy-5-methylpyridin-3-yl)-1H-inden-1,3(2H)-dione;
73) 2-(5-Chloro-3-hydroxypyridin-2-yl)-2-hydroxy-1H-inden-1,3(2H)-dione;
75) 2-Hydroxy-2-(6-hydroxyquinolin-7-yl)-1H-inden-1,3(2H)-dione;
76) Butyric acid 2-(2-butyrylamino-1,3-dioxo-indan-2-yl)-5-isopropyl-phenyl ester;
77) Octanoic acid 7-isopropyl-9b-octanoylamino-10-oxo-9b,10-dihydro-5-oxa-indeno[2,1-a]inden-4b-yl ester;
78) Hexanoic acid 2-(2-hexanoylamino-1,3-dioxo-indan-2-yl)-5-isopropyl-phenyl ester;
79) Heptanoic acid 2-(2-heptanoylamino-1,3-dioxo-indan-2-yl)-5-isopropyl-phenyl ester;
80) 2,2-Dimethyl-propionic acid 2-(1,3-dioxo-2-pentanoylam ino-indan-2-yl)-5-isopropyl-phenyl ester;
81) 2-(4-Amino-1,3-dioxo-2-pentanam ido-2,3-dihydro-1H-inden-2-yl)-5-isopropylphenyl pentanoate;
82) 2-(4-Amino-2-hexanam ido-1,3-dioxo-2,3-dihydro-1H-inden-2-yl)-5-isopropylphenyl hexanoate;
83) 2-(4-Amino-2-heptanam ido-1,3-dioxo-2,3-dihydro-1H-inden-2-yl)-5-isopropylphenyl heptanoate;
84) 2-(4-Amino-1,3-dioxo-2-propionamido-2,3-dihydro-1H-inden-2-yl)-5-isopropylphenyl propionate;
85) 2-(4-Amino-2-butyramido-1,3-dioxo-2,3-dihydro-1H-inden-2-yl)-5-isopropylphenyl butyrate;
86) N-(2-(2-Hydroxy-1,3-dioxo-2,3-dihydro-1H-inden-2-yl)-4,5-dimethylphenyl)acetamide;
87) N-(2-(2-Hydroxy-1,3-dioxo-2,3-dihydro-1H-inden-2-yl)-4,5-dimethylphenyl)propionamide;
88) N-(5-Ethyl-2-(2-hydroxy-1,3-dioxo-2,3-dihydro-1H-inden-2-yl)phenyl)acetamide;
89) N-(2-(2-Hydroxy-1,3-dioxo-2,3-dihydro-1H-inden-2-yl)-4,5-dimethylphenyl)butyramide;
90) N-(2-(2-Hydroxy-1,3-dioxo-2,3-dihydro-1H-inden-2-yl)-4,5-dimethylphenyl)isobutyramide;
91) 2-(4-Amino-2-octanamido-1,3-dioxo-2,3-dihydro-1H-inden-2-yl)-5-isopropylphenyl octanoate;
92) 2-(2-Acetamido-1,3-dioxo-2,3-dihydro-1H-inden-2-yl)-5-isopropylphenyl methyl carbonate;
93) 2-(2-Acetamido-1,3-dioxo-2,3-dihydro-1H-inden-2-yl)-5-isopropylphenyl pentanoate;
94) N-(2-(4-Acetamido-2-hydroxy-7-nitro-1,3-dioxo-2,3-dihydro-1H-inden-2-yl)-4,5-dimethylphenyl)isobutyramide;
95) N-(2-(2-Hydroxy-1,3-dioxo-2,3-dihydro-1H-inden-2-yl)-5-isopropylphenyl)isobutyramide;
96) 2-(2-Acetamido-4-amino-1,3-dioxo-2,3-dihydro-1H-inden-2-yl)-5-isopropylphenyl butyl carbonate2-(2-acetamido-4-amino-1,3-dioxo-2,3-dihydro-1H-inden-2-yl)-5-isopropylphenyl butyl carbonate;
97) 2-(2-Acetamido-1,3-dioxo-2,3-dihydro-1H-inden-2-yl)-5-isopropylphenyl methylcarbamate;
98) Dimethyl-carbamic acid 2-(2-acetylamino-1,3-dioxo-indan-2-yl)-5-isopropyl-phenyl ester;
99) Carbonic acid 2-(2-acetylamino-1,3-dioxo-indan-2-yl)-5-isopropyl-phenyl ester phenyl ester;
100) 2-(2-Acetamido-4-amino-1,3-dioxo-2,3-dihydro-1H-inden-2-yl)-5-isopropylphenyl dimethylcarbamate;
101) 2-(2-Acetamido-1,3-dioxo-2,3-dihydro-1H-inden-2-yl)-5-isopropylphenyl ethyl carbonate;
102) Ethyl acetyl(2-(2-hydroxy-4-isopropylphenyl)-1,3-dioxo-2,3-dihydro-1H-inden-2-yl)carbamate;
103) 2-(2-Acetamido-4-amino-1,3-dioxo-2,3-dihydro-1H-inden-2-yl)-5-isopropylphenyl ethylcarbamate;
105) Ethyl (6-(2-((ethoxycarbonyl)oxy)-4-isopropylphenyl)-5,7-dioxo-6,7-dihydro-5H-cyclopenta[b]pyridin-6-yl)carbonate;
106) N-(2-(2-Hydroxy-1,3-dioxo-2,3-dihydro-1H-inden-2-yl)-4,5-dimethoxyphenyl)isobutyramide;
107) N-[2-(4-Amino-2-hydroxy-1,3-dioxo-indan-2-yl)-4,5-dimethoxy-phenyl]-isobutyramide; and
108) N-[2-(2-Hydroxy-5,6-dimethoxy-1,3-dioxo-indan-2-yl)-4,5-dimethoxy-phenyl]-isobutyramide;

or a pharmaceutically acceptable salt or optical isomer thereof.

20. A method for treating a viral disease in a patient, comprising administering a therapeutically effective amount of the compound, pharmaceutically acceptable salt, or optical isomer of claim 19 to the patient.

* * * * *